US005654443A

United States Patent [19]
Wollowitz et al.

[11] Patent Number: 5,654,443
[45] Date of Patent: Aug. 5, 1997

[54] COMPOUNDS FOR THE PHOTO DECONTAMINATION OF PATHOGENS IN BLOOD

[75] Inventors: Susan Wollowitz, Walnut Creek; Stephen T. Isaacs, Orinda; Henry Rapoport; Hans Peter Spielmann, both of Berkeley, all of Calif.

[73] Assignee: Cerus Corporation, Concord, Calif.

[21] Appl. No.: 455,955

[22] Filed: May 31, 1995

Related U.S. Application Data

[62] Division of Ser. No. 342,366, Nov. 18, 1994, which is a division of Ser. No. 83,459, Jun. 28, 1993, Pat. No. 5,399,719.

[51] Int. Cl.$^6$ .................................................. C07D 493/04
[52] U.S. Cl. ................................................................ 549/282
[58] Field of Search ............................................ 549/282

[56] References Cited

U.S. PATENT DOCUMENTS

| | | | |
|---|---|---|---|
| 4,124,598 | 11/1978 | Hearst et al. | 260/343.21 |
| 4,157,723 | 6/1979 | Granzow et al. | 141/1 |
| 4,169,204 | 9/1979 | Hearst et al. | 546/270 |
| 4,196,281 | 4/1980 | Hearst et al. | 536/28 |
| 4,216,154 | 8/1980 | Kaufman | 260/343.21 |
| 4,235,781 | 11/1980 | Kaufman | 260/343 |
| 4,265,280 | 5/1981 | Ammann et al. | 141/98 |
| 4,269,851 | 5/1981 | Kaufman | 424/279 |
| 4,269,852 | 5/1981 | Kaufman | 424/279 |
| 4,279,922 | 7/1981 | Kaufman | 424/279 |
| 4,294,822 | 10/1981 | Kaufman | 424/59 |
| 4,294,847 | 10/1981 | Kaufman | 424/279 |
| 4,298,614 | 11/1981 | Kaufman | 424/279 |
| 4,328,239 | 5/1982 | Kaufman | 424/279 |
| 4,370,344 | 1/1983 | Kaufman | 424/279 |
| 4,412,835 | 11/1983 | Spencer | 604/29 |
| 4,683,195 | 7/1987 | Mullis et al. | 435/6 |
| 4,683,202 | 7/1987 | Mullis | 435/91 |
| 4,727,027 | 2/1988 | Wiesehahn et al. | 435/173 |
| 4,748,120 | 5/1988 | Wiesehahn et al. | 435/173 |
| 5,399,719 | 3/1995 | Wollowitz et al. | 549/282 |

OTHER PUBLICATIONS

Melnick, J.L., "Viral Hepatitis: One Disease but Multiple Viruses," Abstracts of Virological Safety Aspects of Plasma Derivatives, Cannes (France), Nov. 3–6 (1992) p. 9.

International Forum: "How Frequent is Posttransfusion Hepatitis after the Introduction of 3rd Generation Donor Screening for Hepatitis B? What is its Probable Nature?" Vox Sang 32:346 (1977).

Ward, J.W., et al., "Transmission of Human Immunodeficiency Virus (HIV) by Blood Transfusions Screened as Negative for HIV Antibody," N. Engl. J. Med., 318:473 (1988).

Schmunis, G.A., "*Trypanosoma cruzi*, the etiologic agent of Chagas' disease: status in the blood supply in endemic and nonedemic countries," Transfusion 31:547–557 (1992).

Hilfenhaus, J., et al., "A strategy for testing established human plasma protein manufacturing procedures for their ability to inactivate or eliminate human immunodeficiency virus," J. Biol. Std. 70:589 (1987).

Horowitz, B., et al., "Inactivation of viruses in labile blood derivatives," Transfusion 25:516 (1985).

Moroff, G., et al., "The influence of irradiation on stored platelets," Transfusion 26:453 (1986).

Prince, A.M., et al., "β–Propiolactone/Ultraviolet Irradiation: A review of Its Effectiveness for Inactivation of Viruses in Blood Derivatives," Reviews of Infect. Diseases 5:92–107 (1983).

Matthews, J.L., et al., "Photodynamic therapy of viral contaminants with potential for blood banking applications," Transfusion 28:81–83 (1988).

North, J., et al., "Photodynamic inactivation of retrovirus by benzoporphyrin derivative: a feline leukemia virus model," Transfusion 32:121–128 (1992).

Sieber, F., et al., "Invitation of Friend Erythroleukemia Virus and Friend Virus—Transformed Cells by Merocyanine 540–Mediated Photosensitization," Blood 73:345–350 (1989).

Rywkin, S., et al., "In Vivo Circulatory Survival of Photochemically Treated Rabbit Red Blood Cells with Aluminum Phthalocyanine Derivatives," Blood 78 (Suppl 1): 352A (Abstract) (1991).

Proudouz, K.N., et al., "Use of Laser U–V for Inactivation of Virus in Blood Platelets," Blood 70:589, (1987).

G.D. Cimino, et al., "Psoralens as Photoactive Probes of Nucleic Acid Structure and Function: Organic Chemistry, Photochemistry, and Biochemistry," Ann. Rev. Biochem. 54:1151 (1985).

Hearst, et al., "The Reaction of the Psoralens with Deoxyribonucleic Acid," Quart. Rev. Biophys. 17:1 (1984).

S.T. Isaacs, et al., "Synthesis and Characterization of New Psoralen Derivatives with Superior Photoreactivity with DNA and RNA," Biochemistry 16:1058 (1977).

S.T. Isaacs, et al., "A Photochemical Characterization of Reactions of Psoralen Derivatives with DNA," Trends in Photobiology (Plenum) pp. 279–294 (1982).

J. Tessman, et al., "Photochemistry of the Furan–Side 8–Methoxypsoralen–Thymide Monoadduct Inside the DNA Helix. conversion to Diadduct and to Pyrone–Side Monoadduct," Biochem. 24:1669 (1985).

(List continued on next page.)

*Primary Examiner*—Ba K. Trinh
*Attorney, Agent, or Firm*—Peter G. Carroll; Kathryn P. Wilke

[57] ABSTRACT

Psoralen compound compositions are synthesized which have substitutions on the 4, 4', 5', and 8 positions of the psoralen, which yet permit their binding to nucleic acid of pathogens. Reaction conditions that photoactivate these bound psoralens result in covalent crosslinking to nucleic acid, thereby inactivating the pathogen. Higher psoralen binding levels and lower mutagenicity results in safer, more efficient, and reliable inactivation of pathogens. In addition to the psoralen compositions, the invention contemplates inactivating methods using the new psoralens.

2 Claims, 27 Drawing Sheets

OTHER PUBLICATIONS

H.J. Alter, et al., "Photochemical Decontamination of Blood Components Containing Hepatitis B and Non–A, Non–B Virus," The Lancet (ii:1446) (1988).

L. Lin, et al., "Use of 8–Methoxypsoralen and Long–Wavelength Ultraviolet Radiation for Decontamination of Platelet Concentrates," Blood 74:517 (1989).

P. Morel, et al., "Photochemical Inactivation of Viruses and Bacteriophage in Plasma and Plasma Fractions," Blood Cells 18:27 (1992).

R.Y. Dodd, et al., "Inactivation of Viruses in Platelet Suspensions that Retain Their In Vitro Characteristics: Comparison of Psoralen–ultraviolet A and Merocyanine 540 Visible Light Methods," Transfusion 31:483–490 (1991).

H. Margolis–Nunno, et al., "Photochemical Virus Sterilization in Platelet Concentrates with Psoralen Derivatives," Thromb Haemostas 65:1162 (Abstract) (1991).

C.V. Hanson, "Photochemical Inactivation of Viruses with Psoralens: An Overview," Blood Cells: 18:7–25 (1992).

Hearst, J.E., and Thiry, L., "The photoinactivation of an RNA animal virus, vesicular stomatitis virus, with the aid of newly synthesized psoralen derivatives," Nucleic Acids Research, 4:1339 (1977).

Hyde and Hearst, "Binding of Psoralen Derivatives to DNA and Chromatin: Influence of the Ionic Environment on Dark Binding and Photoreactivity," Biochemistry, 17, 1251 (1978).

Thompson, et al., J. Mol. Biol., "Determination of the Secondary Structure of *Drosophila Melanogaster* 5 S RNA by Hydroxymethyltrimethylpsoralen Crosslinking," 147:417 (1981).

Thompson, et al., "Dependence of 4'–(Hydroxymethyl)–4, 5', 8–trimethylpsoralen Photoaddition on the Conformation of Ribonucleic Acid," Biochemistry 21:1363 (1982).

Isaacs, S.T., G. Wiesehahn and L.M. Hallick, "In Vitro Characterization of the Reaction of Four Psoralen Derivatives with DNA," NCI Monograph 66:21 (1984).

Adams, et al., "The Pechmann Reaction," Organic Reactions, vol. VII, Chapter 1, Wiley, NY (1953).

Bender, et al., "Psoralen Synthesis. Improvements in Furan Ring Formation. Application to the Synthesis of 4,5',8–Trimethylpsoralen," J. Org. Chem. 44:2176 (1979).

Olah and Kuhn, "Selective Friedel–Crafts Reactions. I. Boran Halide Catalyzed Haloalkylation of Benzene and Alkylbenzenes with Flurohaloalkanes," J. Org. Chem. 29, 2317 (1964).

Friedel–Crafts and Related Reactions, vol. II, Part 2, Olah, ed., Interscience, NY, p. 749 (1964).

Lee, B.L., et al., "Interaction of Psoralen–Derivatized Oligodeoxyrionucleoside Methylphosphonates with Single–Stranded DNA," Biochemistry, 27, 3197–3203 (1988).

Goldenberg, M., et al., "Synthesis and Properties of Novel Psoralen Derivatives," Biochemistry 27:6971 (1988).

Larock, "Alkanes and Arenes," Comprehensive Organic Transformations, Chapter 1, p. 5, VCH Publishers, NY (1989).

Isaacs, et al., "Synthesis of Deuterium and Tritium Labeled Psoralens," J. Labelled Cmpds. Radiopharm., 19, 345 (1982).

Durst, T., "Dimethylsulfoxide (DMSO) in Organic Synthesis," Adv. Org. Chem. 6:285 (1969).

Morrow, J.F., et al., "Septic Reactions to Platelet Transfusions," JAMA 266:555–558 (1991).

Bertolini, F., et al., "Platelet Quality After 15–day Storage of Platelet Concentrates Prepared from Buffy Coats and Stored in a Glucose–Free Crystalloid Medium," Transfusion 32:152–156 (1992).

D.M. Maron and B.N. Ames, "Revised methods for the Salmonella mutagenicity test," Mutation Research, 113:173 (1983).

Kaufman, et al., "Reactions of Furocoumarins. II(1). Synthetic Aminomethyl Psoralens via Chloromethylation of Benzylic Bromination," J. Heterocyclic Chem. 19:1051 (1982).

Hanson, C.V., et al., "Application of a Rapid Microplaque assay for Determination of Human Immunodeficiency Virus Neutralizing Antibody Titers," J. Clin. Micro 28:2030 (1990).

McLeod, et al., "Synthesis of Benzofuranoid Systems. I. Furocoumarins, Benzofurans and Dibenzofurans," Tetrahedron Letters 237 (1972).

German Patent No. P 39 28 900.1, Issued Mar. 7, 1991, Name: Weickmann, et al., For: "Neue Nucleotidderivate, ihre Herstellung und ihre Verwendung," Filed Aug. 31, 1989.

Metzelaar, M.J., "Studies on the Expression of Activation–Markers on Human Platelets," (Thesis) (1961).

Moroff, G., et al., "Factors Influencing Changes in pH during Storage of Platelet Concentrates at 20–24°C," Vox Sang 43:33–45 (1982).

Stack, G., "Storage of Platelet Concentrate,", Blood Separation and Platelet Fractionation, p. 99–125 (1991).

Goldman, M. and Blajchman, M.A., "Blood Product–Associated Bacterial Sepsis", Transfusion Medicine Reviews, V:73–83 (1991).

COMPOUNDS FOR THE PHOTO DECONTAMINATION OF PATHOGENS IN BLOOD

This application is a division of application Ser. No. 08/342,366, filed Nov. 18, 1994, which is a division of application Ser. No. 08/083,459, filed Jun. 28, 1993, Now issued as U.S. Pat. No. 5,399,719.

FIELD OF THE INVENTION

The present invention provides new psoralens and methods of synthesis of new psoralens having enhanced ability to inactivate pathogens in the presence of ultraviolet light. The present invention also provides methods of using new and known compounds to inactivate pathogens in health related products to be used in vivo and in vitro, and in particular, blood products.

BACKGROUND

Although improved testing methods for hepatitis B (HBV), hepatitis C (HCV), and human immunodeficiency virus (HIV) have markedly reduced the incidence of transfusion associated diseases, other viral, bacterial, and protozoal agents are not routinely tested for, and remain a potential threat to transfusion safety. Schmunis, G. A., Transfusion 31:547–557 (1992). In addition, testing will not insure the safety of the blood supply against future unknown pathogens that may enter the donor population resulting in transfusion associated transmission before sensitive tests can be implemented.

The recent introduction of a blood test for HCV will reduce transmission of this virus; however, it has a sensitivity of only 67% for detection of probable infectious blood units. HCV is responsible for 90% of transfusion associated hepatitis. Melniek, J. L., Abstracts of Virological Safety Aspects of Plasma, Cannes, November 3–6 (1992) page 9. It is estimated that, with the test in place, the risk of infection is 1 out of 3300 units transfused.

Further, while more sensitive serological assays are in place for HIV-1 and HBV, these agents can nonetheless be transmitted by seronegative blood donors. International Forum: Vox Sang 32:346 (1977). Ward, J. W., et al., N. Engl. J. Med., 318:473 (1988). Up to 10% of total transfusion-related hepatitis and 25% of severe icteric cases are due to the HBV transmitted by hepatitis B surface antigen (HBasAg) negative donors. Vox Sang 32:346 (1977). To date, fifteen cases of transfusion-associated HIV infections have been reported by the Center for Disease Control (CDC) among recipients of blood pretested negative for antibody to HIV-1.

Even if seroconversion tests were a sufficient screen, they may not be practical in application. For example, CMV (a herpes virus) and parvo B19 virus in humans are common. When they occur in healthy, immunocompetent adults, they nearly always result in asymptomatic seroconversion. Because such a large part of the population is seropositive, exclusion of positive units would result in substantial limitation of the blood supply.

An alternative approach to eliminate transmission of viral diseases through blood products is to develop a means to inactivate pathogens in transfusion products. Development of an effective technology to inactivate infectious pathogens in blood products offers the potential to improve the safety of the blood supply, and perhaps to slow the introduction of new tests, such as the HIV-2 test, for low frequency pathogens. Ultimately, decontamination technology could significantly reduce the cost of blood products and increase the availability of scarce blood products. Furthermore, decontamination may extend the storage life of platelet concentrates which, according to Goldman M. and M. A. Blajchman, Transfusion Medicine Reviews. V: 73–83 (1991), are currently limited by potential bacterial contamination.

Several methods have been reported for the inactivation or elimination of viral agents in erythrocyte-free blood products. Some of these techniques, such as heat (Hilfenhous, J., et al., J. Biol. Std. 70:589 (1987)), solvent/detergent treatment (Horowitz, B., et al, Transfusion 25:516 (1985)), gamma-irradiation (Moroff, G., et al., Transfusion 26:453 (1986)), UV radiation combined with beta propriolactone, (Prince A. M., et al., Reviews of Infect Diseases 5:92–107 (1983) Prince A. M., et al., Reviews of Infect Diseases 5:92–107 (1983)), visible laser light in combination with hematoporphyrins (Matthews J. L., et al., Transfusion 28:81–83 (1988); North J., et al., Transfusion 32:121–128 (1992)), use of the photoactive dyes aluminum phthalocyananine and merocyanine 540 (Sieber F., et al., Blood 73:345–350 (1989); Rywkin S., et al., Blood 78 (Suppl 1):352a (Abstract) (1991)) or UV alone (Proudouz, K. N., et al., Blood 70:589 (1987)) are completely incompatible with maintenance of platelet function.

Other methods inactivate viral agents by using known furocoumarins, such as psoralens, in the presence of ultraviolet light. Psoralens are tricyclic compounds formed by the linear fusion of a furan ring with a coumarin. Psoralens can intercalate between the base pairs of double-stranded nucleic acids, forming covalent adducts to pyrimidine bases upon absorption of long wave ultraviolet light (UVA). G. D. Cimino et al., Ann. Rev. Biochem. 54:1151 (1985); Hearst et al., Quart. Rev. Biophys. 17:1 (1984). If there is a second pyrimidine adjacent to a psoralen-pyrimidine monoadduct and on the opposite strand, absorption of a second photon can lead to formation of a diadduct which functions as an interstrand crosslink. S. T. Isaacs et al., Biochemistry 16:1058 (1977); S. T. Isaacs et al., Trends in Photobiology (Plenum) pp. 279–294 (1982); J. Tessman et al., Biochem. 24:1669 (1985); Hearst et al., U.S. Pat. Nos. 4,124,598, 4,169,204, and 4,196,281, hereby incorporated by reference.

The covalently bonded psoralens act as inhibitors of DNA replication and thus have the potential to stop the replication process. Due to this DNA binding capability, psoralens are of particular interest in relation to solving the problems of creating and maintaining a safe blood supply. Some known psoralens have been shown to inactivate viruses in some blood products. H. J. Alter et al., The Lancet (ii:1446) (1988); L. Lin et al., Blood 74:517 (1989) (decontaminating platelet concentrates); G. P. Wiesehahn et al., U.S. Pat. Nos. 4,727,027 and 4,748,120, hereby incorporated by reference, describe the use of a combination of 8-methoxypsoralen (8-MOP) and irradiation. P. Morel et al., Blood Cells 18:27 (1992) show that 300 ug/mL of 8-MOP together with ten hours of irradiation with ultraviolet light can effectively inactivate viruses in human serum. Similar studies using 8-MOP and aminomethyltrimethylpsoralen (AMT) have been reported by other investigators. Dodd RY, et al., Transfusion 31:483–490 (1991); Margolis-Nunno, H., et al., Thromb Haemostas 65:1162 (Abstract) (1991). Indeed, the photoinactivation of a broad spectrum of microorganisms has been established, including HBV, HCV, and HIV. [Hanson C. V., Blood Cells: 18:7–24 (1992); Alter, H. J., et al., The Lancet ii:1446 (1988); Margolis-Nunno H. et al., Thromb Haemostas 65:1162 (Abstract) (1991).]

Psoralen photoinactivation is only feasible if the ability of the psoralen to inactivate viruses is sufficient to ensure a safety margin in which complete inactivation will occur. On the other hand, the psoralen must not be such that it will cause damage to blood cells. Previous compounds and protocols have necessitated the removal of molecular oxygen from the reaction before exposure to light, to prevent damage to blood products from oxygen radicals produced during irradiation. See L. Lin et al., Blood 74:517 (1989); U.S. Pat. No. 4,727,027, to Wiesehahn. This is a costly and time consuming procedure.

Finally, some commonly known compounds used in PCD cause undesirable mutagenic effects which appears to increase with increased ability to kill virus. In other words, the more effective the known compounds are at inactivating viruses, the more mutagenic the compounds are, and thus, the less useful they at any point in an inactivation system of products for in vivo use. A new psoralen compound is needed which displays improved ability to inactivate pathogens and low mutagenicity, thereby ensuring safe and complete inactivation of pathogens in blood decontamination methods.

SUMMARY OF THE INVENTION

The present invention provides new psoralens and methods of synthesis of new psoralens having enhanced ability to inactivate pathogens in the presence of ultraviolet light which is not linked to mutagenicity. The present invention also provides methods of using new and known compounds to inactivate pathogens in health related products to be used in vivo and in vitro, and particularly, in blood products and blood products in synthetic media.

With respect to new compounds, the present invention contemplates psoralen compounds, comprising: a) a substituent $R_1$ on the 4' carbon atom, selected from the group comprising: $-(CH_2)_u-NH_2$, $-(CH_2)_w-R_2-(CH_2)_z-NH_2$, $-(CH_2)_w-R_2-(CH_2)_x-R_3-(CH_2)_z-NH_2$, and $-(CH_2)_w-R_2-(CH_2)_x-R_3-(CH_2)_y-R_4-(CH_2)_z-NH_2$; wherein $R_2$, $R_3$, and $R_4$ are independently selected from the group comprising O and NH, in which u is a whole number from 1 to 10, w is a whole number from 1 and 5, x is a whole number from 2 and 5, y is a whole number from 2 and 5, and z is a whole number from 2 and 6; and b) substituents $R_5$, $R_6$, and $R_7$ on the 4, 5', and 8 carbon atoms respectively, independently selected from the group comprising H and $(CH_2)_v CH_3$, where v is a whole number from 0 to 5; or a salt thereof. Where an element is "independently selected" from a group, it means that the element need not be the same as other elements chosen from the same group.

The invention contemplates specific compounds of the above structure, wherein $R_1$ is $-CH_2-O-(CH_2)_2-NH_2$, and wherein $R_5$, $R_6$, and $R_7$ are all $CH_3$, wherein $R_1$ is $-CH_2-O-(CH_2)_2-O-(CH_2)_2-NH_2$, and $R_5$, $R_6$, and $R_7$ are all $CH_3$, wherein $R_1$ is $-CH_2-O-(CH_2)_2-O-(CH_2)_2-NH-(CH_2)_4-NH_2$, and $R_5$, $R_6$, and $R_7$ are all $CH_3$, wherein $R_1$ is $CH_2-NH-(CH_2)_4-NH_2$, and $R_5$, $R_6$, and $R_7$ are all $CH_3$, and wherein $R_1$ is $CH_2-NH-(CH_2)_3-NH-(CH_2)_4-NH-(CH_2)_3-NH_2$, and $R_5$, $R_6$, and $R_7$ are all $CH_3$.

The present invention also contemplates psoralen compounds, comprising: a) a substituent $R_1$ on the 5' carbon atom, selected from the group comprising: $-(CH_2)_u-NH_2$, $-(CH_2)_w-R_2-(CH_2)_z-NH_2$, $-(CH_2)_w-R_2-(CH_2)_x-R_3-(CH_2)_z-NH_2$, and $-(CH_2)_w-R_2-(CH_2)_x-R_3-(CH_2)_y-R_4-(CH_2)_z-NH_2$; wherein $R_2$, $R_3$, and $R_4$ are independently selected from the group comprising O and NH, and in which u is a whole number from 1 to 10, w is a whole number from 1 to 5, x is a whole number from 2 to 5, y is a whole number from 2 to 5, and z is a whole number from 2 to 6; and, b) substituents $R_5$, $R_6$, and $R_7$ on the 4, 4', and 8 carbon atoms respectively, independently selected from the group comprising H and $(CH_2)_v CH_3$, where v is a whole number from 0 to 5, and where when $R_1$ is $-(CH_2)_u-NH_2$, $R_6$ is H; or a salt thereof. The present invention contemplate a specific compound having the above structure, wherein $R_1$ is $-CH_2-NH-(CH_2)_4-NH_2$, and $R_5$, $R_6$, and $R_7$ are all $CH_3$.

The present invention also contemplates psoralen compounds, comprising: a) a substituent $R_1$ on the 5' carbon atom, selected from the group comprising: $-(CH_2)_u-NH_2$, $-(CH_2)_w-R_2-(CH_2)_z-NH_2$, $-(CH_2)_w-R_2-(CH_2)_x-R_3-(CH_2)_z-NH_2$, and $-(CH_2)_w-R_2-(CH_2)_x-R_3-(CH_2)_y-R_4-(CH_2)_z-NH_2$; wherein $R_2$, $R_3$, and $R_4$ are independently selected from the group comprising O and NH, and in which u is a whole number from 3 to 10, w is a whole number from 1 to 5, x is a whole number from 2 to 5, y is a whole number from 2 to 5, and z is a whole number from 2 to 6; and, b) substituents $R_5$, $R_6$, and $R_7$ on the 4, 4', and 8 carbon atoms respectively, independently selected from the group comprising H and $(CH_2)_v CH_3$, where v is a whole number from 0 to 5; or a salt thereof. The present invention contemplates a specific compound having the above structure, wherein $R_1$ is $-CH_2-NH-(CH_2)_4-NH_2$, and $R_5$, $R_6$, and $R_7$ are all $CH_3$.

With respect to methods for synthesizing new compounds substituted at the 4' position of the psoralen, the present invention contemplates a method of synthesizing 4'-(w-amino-2-oxa)alkyl-4,5',8-trimethylpsoralen, comprising the steps: a) providing 4'-(w-hydroxy-2-oxa)alkyl-4,5',8-trimethylpsoralen; b) treating 4'-(w-hydroxy-2-oxa)alkyl-4,5',8-trimethylpsoralen with a base and methanesulfonyl chloride so that 4'-(w-methanesulfonyloxy-2-oxa)alkyl-4,5',8-trimethylpsoralen is produced; c) treating 4'-(w-methanesulfonyloxy-2-oxa)alkyl-4,5',8-trimethylpsoralen with sodium azide, so that 4'-(w-azido-2-oxa)alkyl-4,5',8-trimethylpsoralen is produced, and d) reducing 4'-[(w-azido-2-oxa)alkyl-4,5',8-trimethylpsoralen so that 4'-[(w-amino-2-oxa)alkyl-4,5',8-trimethylpsoralen is produced.

The present invention further contemplates a method of synthesizing a compound of the structure which has a substituent $R_1$ on the 4' position of the psoralen, described above, where $R_1$ comprises $-(CH_2)-O-(CH_2)_x-O-(CH_2)_z NH_2$, where x=z, comprising the steps: a) providing a 4'-halomethyl-4,5',8-trimethylpsoralen selected from the group comprising 4'-chloromethyl-4,5',8-trimethylpsoralen, 4'-bromomethyl-4,5',8-trimethylpsoralen, and 4'-iodomethyl-4,5',8-trimethylpsoralen; b) treating said 4'-halomethyl-4,5',8-trimethylpsoralen with $HO(CH_2)_x O$ $(CH_2)_z OH$ so that 4'-(w-hydroxy-2,n-dioxa)alkyl-4,5',8-trimethylpsoralen is produced, where n=x+3; c) treating said 4'-(w-hydroxy-2,n-dioxa)alkyl-4,5',8-trimethylpsoralen with a base and methanesulfonyl chloride so that 4'-(w-methanesulfonyloxy-2,n-dioxa)alkyl-4,5',8-trimethylpsoralen is produced; d) treating 4'-(w-methanesulfonyloxy-2,n-dioxa)alkyl-4,5',8-trimethylpsoralen with sodium azide so that 4'-(w-azido-2,n-dioxa)alkyl-4,5',8-trimethylpsoralen is produced; and e) reducing 4'-(w-azido-2,n-dioxa)alkyl-4,5',8-trimethylpsoralen so that 4'-(w-amino-2,n-dioxa)alkyl-4,5',8-trimethylpsoralen is produced.

The present invention also contemplates a method of synthesizing 4'-(12-amino-8-aza-2,5-dioxa)dodecyl-4,5',8-trimethylpsoralen, comprising the steps: a) providing a 4'-halomethyl-4,5',8-trimethylpsoralen, selected from the group comprising 4'-chloromethyl-4,5',8-trimethylpsoralen, 4'-bromomethyl-4,5',8-trimethylpsoralen, and 4'-iodomethyl-4,5',8-trimethylpsoralen; b) treating said 4'-halomethyl-4,5',8-trimethylpsoralen with diethylene glycol so that 4'-(7-hydroxy-2,5-dioxa)heptyl-4,5',8-trimethylpsoralen is produced; c) treating 4'-(7-hydroxy-2,5-dioxa)heptyl-4,5',8-trimethylpsoralen with a base and methanesulfonyl chloride so that 4'-(7-methanesulfonyloxy-2,5-dioxa)heptyl-4,5',8-trimethylpsoralen is produced; d) treating 4'-(7-methanesulfonyloxy-2,5-dioxa)heptyl-4,5',8-trimethylpsoralen with 1, 4-diaminobutane so that 4'-(12-amino-8-aza-2,5-dioxa)dodecyl-4,5',8-trimethylpsoralen is produced.

The present invention contemplates a method of synthesizing 4'-(w-amino-2-aza)alkyl-4,5',8-trimethylpsoralen, comprising: a) providing 4'-halomethyl-4,5',8-trimethylpsoralen, selected from the group comprising 4'-chloromethyl-4,5',8-trimethylpsoralen, 4'-bromomethyl-4,5',8-trimethylpsoralen, and 4'-iodomethyl-4,5',8-trimethylpsoralen; b) treating said 4'-halomethyl-4,5',8-trimethylpsoralen with 1,w-aminoalkane to produce 4'-(w-diamino-2-aza)alkyl-4,5',8-trimethylpsoralen.

The present invention additionally contemplates a method of synthesizing 4'-(14-amino-2,6,11-triaza)tetradecyl-4,5',8-trimethylpsoralen, comprising: a) providing 4,5',8-trimethylpsoralen-4'-carboxaldehyde; b) treating 4,5',8-trimethylpsoralen-4'-carboxaldehyde with spermine and a reducing agent to produce 4'-(14-amino-2,6,11-triaza) tetradecane-4,5',8-trimethylpsoralen.

Finally, the present invention contemplates the following method of synthesizing 5'-(w-amino-2-aza)alkyl-4,4',8-trimethylpsoralen, comprising: a) providing a 5'-halomethyl-4,4',8-trimethylpsoralen, selected from the group comprising 5'-chloromethyl-4,4',8-trimethylpsoralen, 5'-bromomethyl-4,4',8-trimethylpsoralen, and 5'-iodomethyl-4,4',8-trimethylpsoralen; b) treating said 5'-halomethyl-4,4',8-trimethylpsoralen with a 1,w-diaminoalkane to produce 5'-(w-amino-2-aza)alkyl-4,4',8-trimethylpsoralen.

The present invention contemplates methods of inactivating microorganisms in blood preparations, comprising, in the following order: a) providing, in any order, i) a compound from the group comprising 4'-primaryamino-substituted psoralens and 5'-primaryamino-substituted psoralens; ii) photoactivating means for photoactivating said compounds; and iii) a blood preparation suspected of being contaminated with a pathogen having nucleic acid; b) adding said compound to said blood preparation; and c) photoactivating said compound, so as to inactivate said pathogen.

The pathogen can be single cell or multicellular organisms, such as bacteria, fungi, mycoplasma and protozoa, or viruses. The pathogen can comprise either DNA or RNA, and this nucleic acid can be single stranded or double stranded. In one embodiment, the blood preparation is either platelets or plasma.

The present invention contemplates that the photoactivating means comprises a photoactivation device capable of emitting a given intensity of a spectrum of electromagnetic radiation comprising wavelengths between 180 nm and 400 nm, and in particular, between 320 nm and 380 nm. It is preferred that the intensity is between 1 and 30 mW/cm$^2$ (e.g., between 10 and 20 mW/cm$^2$) and that the mixture is exposed to this intensity for between one second and thirty minutes (e.g., ten minutes).

The present invention contemplates embodiments wherein said blood preparation is in a synthetic media. In one embodiment, the concentration of compound is between 0.1 and 250 μM. In a preferred embodiment, the compound is added to said blood preparation at a concentration of between 10 and 150 μM.

The present invention contemplates embodiments of the methods where inactivation is performed without limiting the concentration of molecular oxygen. Furthermore, there is no need for the use of cosolvents (e.g., dimethyl sulphoxide (DMSO)) to increase compound solubility.

In one embodiment, the present invention contemplates methods of inactivating microorganisms in blood preparations, wherein the compound is a 4'-primaryamino-substituted psoralen, comprising: a) a substituent $R_1$ on the 4' carbon atom, selected from the group comprising: —$(CH_2)_u$—$NH_2$, —$(CH_2)_w$—$R_2$—$(CH_2)_z$—$NH_2$, —$(CH_2)_w$—$R_2$—$(CH_2)_x$—$R_3$—$(CH_2)_z$—$NH_2$, and —$(CH_2)_w$—$R_2$—$(CH_2)_x$—$R_3$—$(CH_2)_y$—$R_4$—$(CH_2)_z$—$NH_2$; wherein $R_2$, $R_3$, and $R_4$ are independently selected from the group comprising O and NH, in which u is a whole number from 1 to 10, w is a whole number from 1 to 5, x is a whole number from 2 to 5, y is a whole number from 2 to 5, and z is a whole number from 2 to 6; and b) substituents $R_5$, $R_6$, and $R_7$ on the 4, 5', and 8 carbon atoms respectively, independently selected from the group comprising H and $(CH_2)_vCH_3$, where v is a whole number from 0 to 5; or a salt thereof.

Alternatively, the present invention contemplates embodiments of the method of inactivation, wherein the compound is a 5'-primaryamino-substituted psoralen comprising: a) a substituent $R_1$ on the 5' carbon atom, selected from the group comprising: —$(CH_2)_u$—$NH_2$, —$(CH_2)_w$—$R_2$—$(CH_2)_z$—$NH_2$, —$(CH_2)_w$—$R_2$—$(CH_2)_x$—$R_3$—$(CH_2)_z$—$NH_2$, and —$(CH_2)_w$—$R_2$—$(CH_2)_x$—$R_3$—$(CH_2)_y$—$R_4$—$(CH_2)_z$—$NH_2$; wherein $R_2$, $R_3$, and $R_4$ are independently selected from the group comprising O and NH, and in which u is a whole number from 1 to 10, w is a whole number from 1 to 5, x is a whole number from 2 to 5, y is a whole number from 2 to 5, and z is a whole number from 2 to 6; and, b) substituents $R_5$, $R_6$, and $R_7$ on the 4, 4', and 8 carbon atoms respectively, independently selected from the group comprising H and $(CH_2)_vCH_3$, where v is a whole number from 0 to 5, and where when $R_1$ is selected from the group comprising —$(CH_2)_u$—$NH_2$, $R_6$ is H; or a salt thereof.

Alternatively, the present invention contemplates embodiments of the method of inactivation, wherein the compound is a 5'-primaryamino-substituted psoralen comprising: a) a substituent $R_1$ on the 5' carbon atom, selected from the group comprising: —$(CH_2)_u$—$NH_2$, —$(CH_2)_w$—$R_2$—$(CH_2)_z$—$NH_2$, —$(CH_2)_w$—$R_2$—$(CH_2)_x$—$R_3$—$(CH_2)_z$—$NH_2$, and —$(CH_2)_w$—$R_2$—$(CH_2)_x$—$R_3$—$(CH_2)_y$—$R_4$—$(CH_2)_z$—$NH_2$; wherein $R_2$, $R_3$, and $R_4$ are independently selected from the group comprising O and NH, and in which u is a whole number from 3 to 10, w is a whole number from 1 to 5, x is a whole number from 2 to 5, y is a whole number from 2 to 5, and z is a whole number from 2 to 6; and, b) substituents $R_5$, $R_6$, and $R_7$ on the 4, 4', and 8 carbon atoms respectively, independently selected from the group comprising H and $(CH_2)_vCH_3$, where v is a whole number from 0 to 5; or a salt thereof.

In one embodiment of the method of inactivation, at least two of the compounds are present. The present invention contemplates embodiments where the compound is introduced either in solution, such as water, saline, or a synthetic media, or in a dry formulation. The present invention also contemplates that the nucleic acid may be DNA or RNA, single stranded or double stranded.

DESCRIPTION OF THE INVENTION

Figure 1:
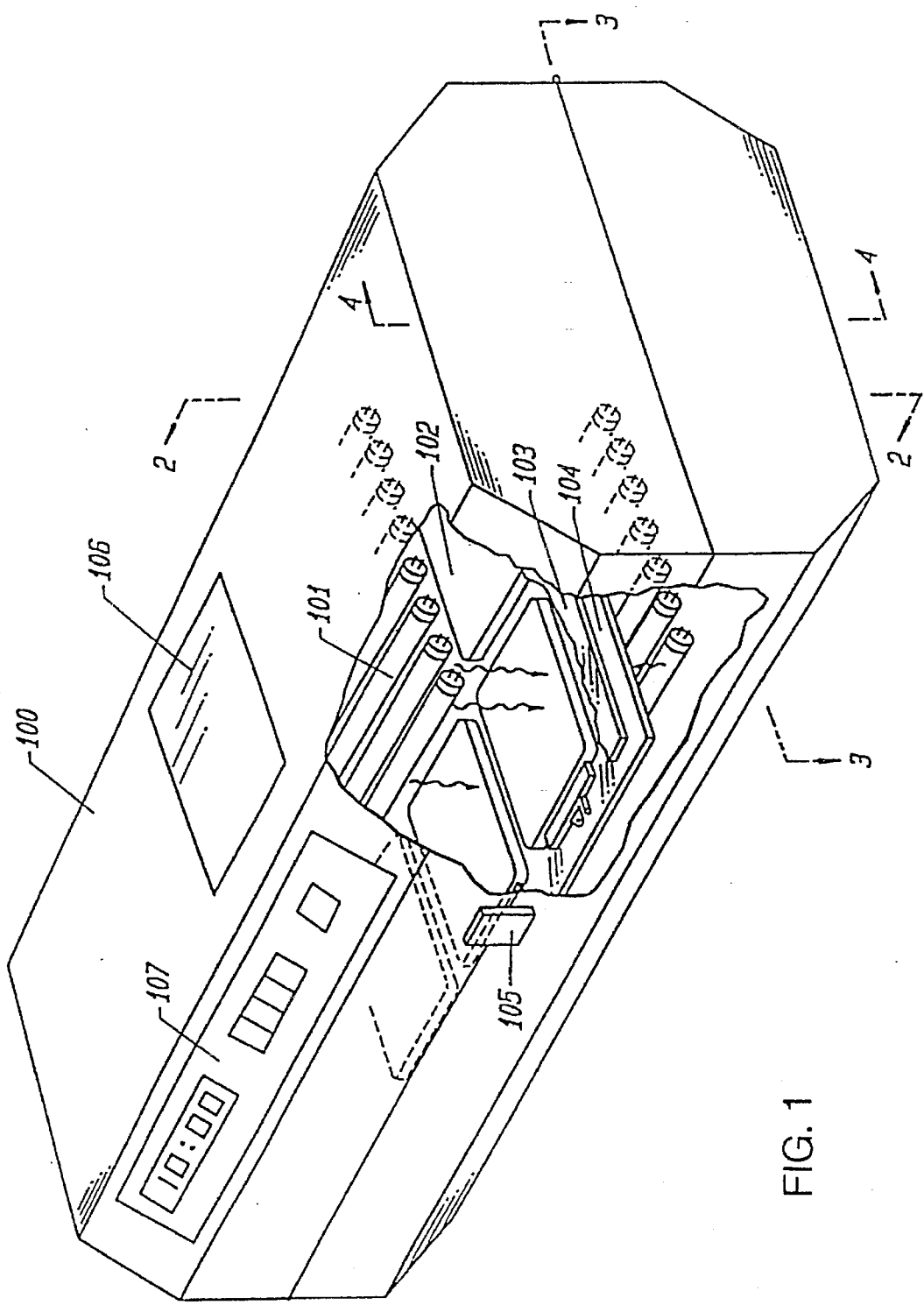
FIG. 1 is a perspective view of one embodiment of the device of the present invention.

The present invention provides new psoralens and methods of synthesis of new psoralens having enhanced ability to inactivate pathogens in the presence of ultraviolet light, which is not linked to mutagenicity. The new psoralens are effective against a wide variety of pathogens. The present invention also provides methods of using new and known compounds to inactivate pathogens in health related products to be used in vivo and in vitro, and in particular, blood products.

The inactivation methods of the present invention provide methods of inactivating pathogens, and in particular, viruses, in blood products prior to use in vitro or in vivo. In contrast with previous approaches, the method requires only short irradiation times and there is no need to limit the concentration of molecular oxygen.

The description of the invention is divided into the following sections: I) Photoactivation Devices, II) Compound Synthesis, III) Binding of Compounds to Nucleic Acid, IV) Inactivation of Contaminants, and V) Preservation of Biochemical Properties of Material Treated.

I. PHOTOACTIVATION DEVICES

The present invention contemplates devices and methods for photoactivation and specifically, for photoactivation of photoreactive nucleic acid binding compounds. The present invention contemplates devices having an inexpensive source of electromagnetic radiation that is integrated into a unit. In general, the present invention contemplates a photoactivation device for treating photoreactive compounds, comprising: a) means for providing appropriate wavelengths of electromagnetic radiation to cause photoactivation of at least one photoreactive compound; b) means for supporting a plurality of samples in a fixed relationship with the radiation providing means during photoactivation; and c) means for maintaining the temperature of the samples within a desired temperature range during photoactivation. The present invention also contemplates methods, comprising: a) supporting a plurality of sample containers, containing one or more photoreactive compounds, in a fixed relationship with a fluorescent source of electromagnetic radiation; b) irradiating the plurality of sample containers simultaneously with electromagnetic radiation to cause photoactivation of at least one photoreactive compound; and c) maintaining the temperature of the sample within a desired temperature range during photoactivation.

The major features of one embodiment of the device of the present invention involve: A) an inexpensive source of ultraviolet radiation in a fixed relationship with the means for supporting the sample containers, B) rapid photoactivation, C) large sample processing, D) temperature control of the irradiated samples, and E) inherent safety.

A. Electromagnetic Radiation Source

Many sources of ultraviolet radiation can be successfully used in decontamination protocols with psoralens. For example, some groups have irradiated sample from above and below by General Electric type F20T12-BLB fluorescent UVA bulbs with an electric fan blowing gently across the lights to cool the area. Alter, H. J., et al., The Lancet, 24:1446 (1988). Another group used Type A405-TLGW/05 long wavelength ultraviolet lamp manufactured by P. W. Allen Co., London placed above the virus samples in direct contact with the covers of petri dishes containing the samples, and was run at room temperature. The total intensity delivered to the samples under these conditions was $1.3 \times 10^{15}$ photons/sec cm$^2$ or 0.7 mW/cm$^2$ in the petri dish. Hearst, J. E., and Thiry, L., Nucleic Acids Research, 4:1339 (1977). However, without intending to be limited to any type of photoactivation device, the present invention contemplates several preferred arrangements for the photoactivation device, as follows.

A preferred photoactivation device of the present invention has an inexpensive source of ultraviolet radiation in a fixed relationship with the means for supporting the sample vessels. Ultraviolet radiation is a form of energy that occupies a portion of the electromagnetic radiation spectrum (the electromagnetic radiation spectrum ranges from cosmic rays to radio waves). Ultraviolet radiation can come from many natural and artificial sources. Depending on the source of ultraviolet radiation, it may be accompanied by other (non-ultraviolet) types of electromagnetic radiation (e.g., visible light).

Particular types of ultraviolet radiation are herein described in terms of wavelength. Wavelength is herein described in terms of nanometers ("nm"; 10$^{-9}$ meters). For purposes herein, ultraviolet radiation extends from approximately 180 nm to 400 nm. When a radiation source, by virtue of filters or other means, does not allow radiation below a particular wavelength (e.g., 320 nm), it is said to have a low end "cutoff" at that wavelength (e.g., "a wavelength cutoff at 300 nanometers"). Similarly, when a radiation source allows only radiation below a particular wavelength (e.g., 360 nm), it is said to have a high end "cutoff" at that wavelength (e.g., "a wavelength cutoff at 360 nanometers").

For any photochemical reaction it is desired to eliminate or least minimize any deleterious side reactions. Some of these side reactions can be caused by the excitation of endogenous chromophores that may be present during the photoactivation procedure. In a system where only nucleic acid and psoralen are present, the endogenous chromophores are the nucleic acid bases themselves. Restricting the photoactivation process to wavelengths greater than 320 nm minimizes direct nucleic acid damage since there is very little absorption by nucleic acids above 313 nm.

In human serum or plasma, for example, the nucleic acid is typically present together with additional biological constituents. If the biological fluid is just protein, the 320 nm cutoff will be adequate for minimizing side reactions (aromatic amino acids do not absorb above 320 nm). If the biological fluid includes other analytes, there may be constituents that are sensitive to particular wavelengths of light. In view of the presence of these endogenous constituents, it is intended that the device of the present invention be designed to allow for irradiation within a small range of specific and desirable wavelengths, and thus avoid damage blood components. The preferred range of desirable wavelengths is between 320 and 350 nm.

Some selectivity can be achieved by choice of commercial irradiation sources. For example, while typical fluorescent tubes emit wavelengths ranging from 300 nm to above 400 nm (with a broad peak centered around 360 nm), BLB type fluorescent lamps are designed to remove wavelengths above 400 nm. This, however, only provides an upper end cutoff.

In a preferred embodiment, the device of the present invention comprises an additional filtering means. In one embodiment, the filtering means comprises a glass cut-off filter, such as a piece of Cobalt glass. In another embodiment, the filtering means comprises a liquid filter solution that transmits only a specific region of the electromagnetic spectrum, such as an aqueous solution of Co(No3)2. This salt solution yields a transmission window of 320–400 nm. In a preferred embodiment, the aqueous solution of Co(No3)2 is used in combination with NiSO4 to remove the 365 nm component of the emission spectrum of the fluorescent or arc source employed. The Co—Ni solution preserves its initial transmission remarkably well even after tens of hours of exposure to the direct light of high energy sources.

It is not intended that the present invention be limited by the particular filter employed. Several inorganic salts and glasses satisfy the necessary requirements. For example, cupric sulfate is a most useful general filter for removing the infra-red, when only the ultraviolet is to be isolated. Its stability in intense sources is quite good. Other salts are known to one skilled in the art. Aperture or reflector lamps may also be used to achieve specific wavelengths and intensities.

When ultraviolet radiation is herein described in terms of irradiation, it is expressed in terms of intensity flux (milliwatts per square centimeter or "mW cm-2"). "Output" is herein defined to encompass both the emission of radiation (yes or no; on or off) as well as the level of irradiation. In a preferred embodiment, intensity is monitored at 4 locations: 2 for each side of the plane of irradiation.

A preferred source of ultraviolet radiation is a fluorescent source. Fluorescence is a special case of luminescence. Luminescence involves the absorption of electromagnetic radiation by a substance and the conversion of the energy into radiation of a different wavelength. With fluorescence, the substance that is excited by the electromagnetic radiation returns to its ground state by emitting a quantum of electromagnetic radiation. While fluorescent sources have heretofore been thought to be of too low intensity to be useful for photoactivation, in one embodiment the present invention employs fluorescent sources to achieve results thus far achievable on only expensive equipment.

As used here, fixed relationship is defined as comprising a fixed distance and geometry between the sample and the light source during the sample irradiation. Distance relates to the distance between the source and the sample as it is supported. It is known that light intensity from a point source is inversely related to the square of the distance from the point source. Thus, small changes in the distance from the source can have a drastic impact on intensity. Since changes in intensity can impact photoactivation results, changes in distance are avoided in the devices of the present invention. This provides reproducibility and repeatability.

Geometry relates to the positioning of the light source. For example, it can be imagined that light sources could be placed around the sample holder in many ways (on the sides, on the bottom, in a circle, etc.). The geometry used in a preferred embodiment of the present invention allows for uniform light exposure of appropriate intensity for rapid photoactivation. The geometry of a preferred device of the present invention involves multiple sources of linear lamps as opposed to single point sources. In addition, there are several reflective surfaces and several absorptive surfaces. Because of this complicated geometry, changes in the location or number of the lamps relative to the position of the samples to be irradiated are to be avoided in that such changes will result in intensity changes.

B. Rapid Photoactivation

The light source of the preferred embodiment of the present invention allows for rapid photoactivation. The intensity characteristics of the irradiation device have been selected to be convenient with the anticipation that many sets of multiple samples may need to be processed. With this anticipation, a fifteen minute exposure time or less is a practical goal.

In designing the devices of the present invention, relative position of the elements of the preferred device have been optimized to allow for fifteen minutes of irradiation time, so that, when measured for the wavelengths between 320 and 350 nanometers, an intensity flux greater than approximately 1 mW cm-2 is provided to the sample vessels.

C. Processing of Large Numbers of Samples

As noted, another important feature of the photoactivation devices of the present invention is that they provide for the processing of large numbers of samples. In this regard, one element of the devices of the present invention is a means for supporting a plurality of sample containers. In the preferred embodiment of the present invention the supporting means comprises a tube rack placed between two banks of lights. By accepting commonly used commercially available tubes, the device of the present invention allows for convenient processing of large numbers of samples.

D. Temperature Control

As noted, one of the important features of the photoactivation devices of the present invention is temperature control. Temperature control is important because the temperature of the sample in the sample at the time of exposure to light can dramatically impact the results. For example, conditions that promote secondary structure in nucleic acids also enhance the affinity constants of many psoralen derivatives for nucleic acids. Hyde and Hearst, Biochemistry, 17, 1251 (1978). These conditions are a mix of both solvent composition and temperature. With single stranded 5 S ribosomal RNA, irradiation at low temperatures enhances the covalent addition of HMT to 5 S rRNA by two fold at 4° C. compared to 20° C. Thompson et al., J. Mol. Biol. 147:417 (1981). Even further temperature induced enhancements of psoralen binding have been reported with synthetic polynucleotides. Thompson et al., Biochemistry 21:1363 (1982).

E. Inherent Safety

Ultraviolet radiation can cause severe burns. Depending on the nature of the exposure, it may also be carcinogenic. The light source of a preferred embodiment of the present invention is shielded from the user. This is in contrast to the commercial hand-held ultraviolet sources as well as the large, high intensity sources. In a preferred embodiment, the irradiation source is contained within a housing made of material that obstructs the transmission of radiant energy (i.e., an opaque housing). No irradiation is allowed to pass to the user. This allows for inherent safety for the user.

II. COMPOUND SYNTHESIS

A. Photoactivation Compounds In General

"Photoactivation compounds" (or "photoreactive compounds") defines a family of compounds that undergo chemical change in response to electromagnetic radiation. Table 1 is a partial list of photoactivation compounds.

TABLE I

| Photoactivation Compounds |
| --- |
| Actinomycins |
| Anthracyclinones |
| Anthramycin |
| Benzodipyrones |
| Fluorenes And Fluorenones |

TABLE I-continued

| Photoactivation Compounds |
| --- |
| Furocoumarins |
| Mitomycin |
| Monosteal Fast Blue |
| Norphillin A |
| Many Organic Dyes Not Specifically Listed |
| Phenanthridines |
| Phenazathionium Salts |
| Phenazines |
| Phenothiazines |
| Phenylazides |
| Quinolines |
| Thiaxanthenones |

The species of photoreactive compounds described herein is commonly referred to as the furocoumarins. In particular, the present invention contemplates those compounds described as psoralens: [7H-furo(3,2-g)-(1)-benzopyran-7-one, or b-lactone of 6-hydroxy-5-benzofuranacrylic acid], which are linear:

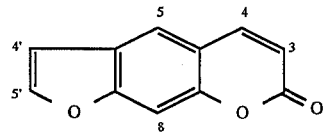

and in which the two oxygen residues appended to the central aromatic moiety have a 1, 3 orientation, and further in which the furan ring moiety is linked to the 6 position of the two ring coumarin system. Psoralen derivatives are derived from substitution of the linear furocoumarin at the 3, 4, 5, 8, 4', or 5' positions.

8-Methoxypsoralen (known in the literature under various named, e.g., xanthotoxin, methoxsalen, 8-MOP) is a naturally occurring psoralen with relatively low photoactivated binding to nucleic acids and low mutagenicity in the Ames assay, described in the following experimental section. 4'-Aminomethyl-4,5',8-trimethylpsoralen (AMT) is one of most reactive nucleic acid binding psoralen derivatives, providing up to 1 AMT adduct per 3.5 DNA base pairs. S. T. Isaacs, G. Wiesehahn and L. M. Hallick, NCI Monograph 66:21 (1984). However, AMT also exhibits significant levels of mutagenicity. A new group of psoralens was desired which would have the best characteristics of both 8-MOP and AMT: low mutagenicity and high nucleic acid binding affinity, to ensure safe and thorough inactivation of pathogens. The compounds of the present invention were designed to be such compounds.

"4'-primaryamino-substituted psoralens" are defined as psoralen compounds which have an $NH_2$ group linked to the 4'-position of the psoralen by a hydrocarbon chain having a total length of 2 to 20 carbons, where 0 to 6 of those carbons are independently replaced by NH or O, and each point of replacement is separated from each other point of replacement by at least two carbons, and is separated from the psoralen by at least one carbon.

"5'-primaryamino-substituted psoralens" are defined as psoralen compounds which have an $NH_2$ group linked to the 5'-position of the psoralen by a hydrocarbon chain having a total length of 1 to 20 carbons, where 0 to 6 of those carbons are independently replaced by NH or O, and each point of replacement is separated from each other point of replacement by at least two carbons, and is separated from the psoralen by at least one carbon.

B. Synthesis of the Psoralens

The present invention contemplates synthesis methods for the novel compounds of the present invention. Several specific examples of the schemes discussed in this section are shown in FIGS. 5A–5F. For ease of reference, the compounds in these figures have been numbered from Compound 1 to Compound 17. For the subclass of the linear psoralens, 4,5',8-trialkylpsoralens can be made as follows. The 4,8-dialkylcoumarins are prepared from 2-alkylresorcinols and a 3-oxoalkanoate ester by the Pechmann reaction (Organic Reactions Vol VII, Chap 1, ed. Adams et al., Wiley, NY, 1953)). The hydroxy group is treated with an allylating reagent, $CH_2=CHX-CH(R_8)-Y$, where X is a halide or hydrogen, Y is a halide or sulfonate, and $R_8$ is H or $(CH_2)_vCH_3$, where v is a whole number from 0 to 4. Claisen rearrangement of the resultant allyl ether gives 4,8-dialkyl-6-allyl-7-hydroxycoumarin. The coumarins are converted to the 4,5',8-trialkylpsoralens using one of the procedures previously described (i.e., see, Bender et al., J. Org. Chem. 44:2176 (1979); Kaufman, U.S. Pat. Nos. 4,235,781 and 4,216,154, hereby incorporated by reference). 4,5',8-Trimethylpsoralen is a natural product and is commercially available (Aldrich Chemical Co., Milwaukee, Wis.).

Halomethylation of the 4,5',8-trialkylpsoralens with chloromethyl methyl ether or bromomethyl methyl ether is described in U.S. Pat. No. 4,124,598, to Hearst. Longer chain 4'-(w-haloalkyl)psoralens (herein referred to as 4'-HATP) where alkyl is $(CH_2)_2$ to $(CH_2)_{10}$ can be prepared under Freidel-Crafts conditions as discussed elsewhere (Olah and Kuhn, J. Org. Chem., 1964, 29, 2317; Friedel-Crafts and Related Reactions, Vol. II, Part 2, Olah, ed., Interscience, NY, 1964, p 749). While reactions of these halomethyl- intermediates with amines (Hearst et al., U.S. Pat. No. 4,124,598, and alcohols (Kaufman, U.S. Pat. No. 4,269,852) have been described, there are no literature reports on the formation of extended chain primary amines, especially those in which the terminal amine is linked to the psoralen by a bridge containing one or more oxygen or nitrogen atoms. Further, the properties of the latter materials, such as decreased mutagenicity are unexpected based on what is known about previously prepared compounds, such as AMT.

Starting from the 4'-HATP, reaction with an excess of a bis-hydroxy compound, HO—(B)—OH, where B is either an alkyl chain (e.g., HO—(B)—OH is 1,3-propanediol) or a monoether (e.g., diethylene glycol) or a polyether (e.g., tetraethylene glycol), either neat or with a solvent such as acetone at 20°–80° C., and a base for the carbon chains longer than halomethyl, gives compound I.

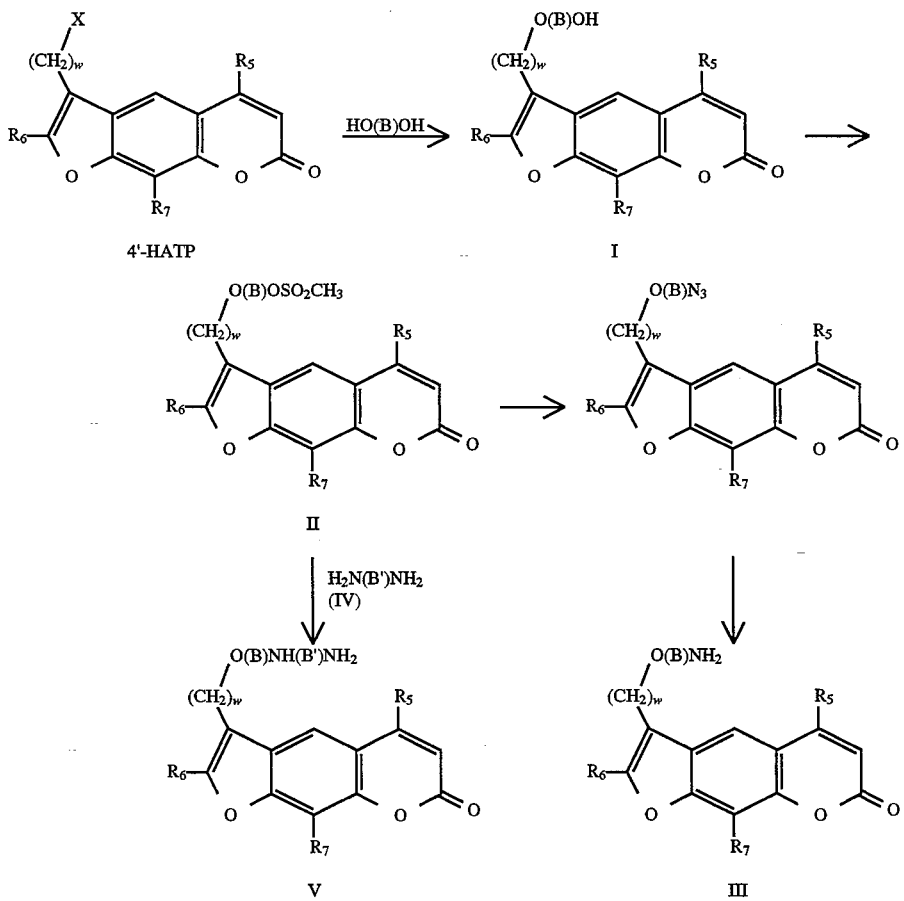

w = 1–5
B,B' = alkyl chain, monoether or polyether; ≦18 atoms long
$R_5, R_6, R_7 =$ H, $(CH_2)vCH_3$;
v = 0–5
X = Br, Cl, I The terminal hydroxy group of compound I can be transformed to an amino group under a variety of conditions (for example see Larock, "Comprehensive Organic Transformations", VCH Publishers, NY, 1989). Particularly, the hydroxy group can be converted to the ester of methanesulfonic acid (structure II). This can subsequently be converted to the azide in refluxing ethanol and the azide reduced to the final amine, structural III. The method described herein utilizes triphenylphosphine and water in THF for the reduction but other methods are contemplated.

Conversely, compound II can be reacted with diamines, H2N—(B')—NH2 (IV) where B' is an alkyl chain (e.g., 1,4,-butanediamine), a monoether (e.g., 3-oxo-1,5-pentanediamine) or a polyether (e.g., 3,6-dioxa-1,8-octanediamine) to give the final product, compound V. This reaction is carried out with an excess of diamine in acetonitrile at reflux, but other solvents and temperatures are equally possible.

It is recognized that alternate preparations for structures III and V are possible, for example where a linear primary alcohol is prepared which already contains the amines in a protected form and subsequently reacted with 4'-HATP in the presence of a suitable base.

Some final compounds are desired which contain an NH group in the carbon chain between the primary amino group and the psoralen ring. When the linkage between this nitrogen and the terminating nitrogen contains only $CH_2$ subunits and oxygen but no other nitrogens (structure VI), the product can conveniently be prepared from the (haloalkyl)psoralen and the appropriate diamine of structure IV. This method is also applicable to final products that contain more than two nitrogens in the chain (structure IX) starting from polyamines of structure VIII (e.g., norspermidine or spermine [commercially available from Aldrich, Milwaukee, Wis.]), however, in this case isomeric structures are also formed in considerable amounts. The more preferred method for the preparation of structure IX is reductive amination of the psoralen-4'-alkanal (VII) with a polyamine of structure VIII and a reducing agent such as sodium cyanoborohydride. This reductive amination is applicable to the synthesis of compounds VI as well. The carboxaldehydes (structure VII, n=0) are known (Isaacs et al., J. Labelled Cmpds. Radiopharm., 1982, 19, 345) and other members of this group can be prepared from the 4'-HATP compounds by conversion of the terminal halo group to an aldehyde functionality (for example, Durst, Adv. Org. Chem. 6:285 (1969)).

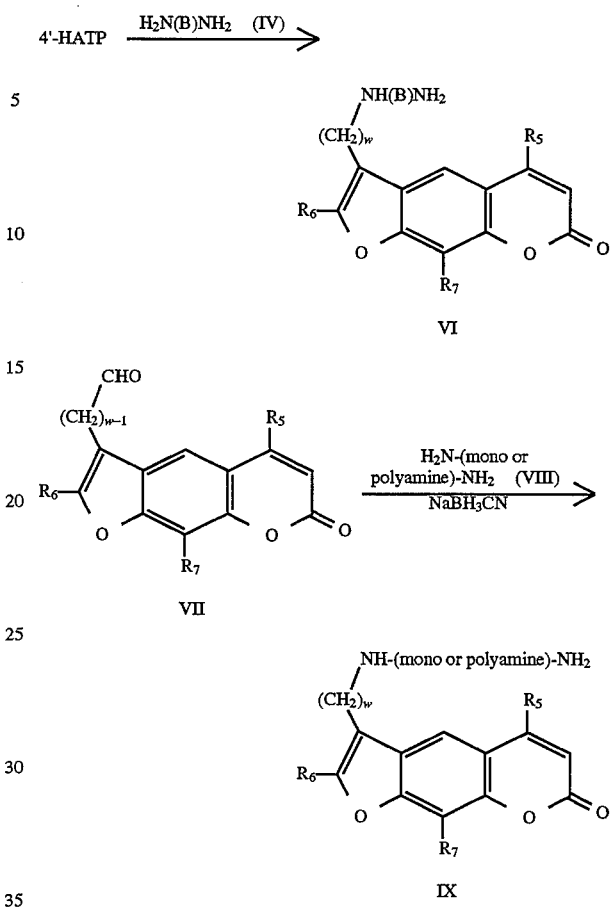

Other final products have a terminal amine linked to the psoralen by an alkyl chain. These are prepared either by reaction of the 4'-HATP with potassium phthalimide and subsequent liberation of the desired amine with hydrazine, or conversion of the 4'-HATP to the cyanide compound, followed by reduction, for example with $NaBH_4$—$CF_3CO_2H$.

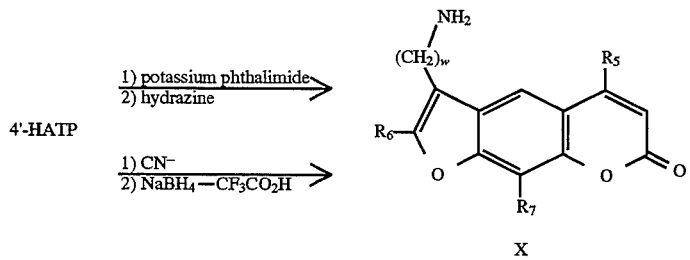

The discussion of the conversion of 4,5',8-trialkylpsoralens to 4'-aminofunctionalized-4,5',8-trialkylpsoralens applies equally well when the 4- and/or 8-position is substituted with only a hydrogen, thus providing 4'-primaryamino-substituted-5', (4 or 8)- dialkylpsoralens and 4'-primaryamino-substituted-5'-alkylpsoralens.

The 4,4',8-trialkylpsoralens can be prepared in two steps starting from the 4,8-dialkyl-7-hydroxycoumarins discussed above. The coumarin is treated with an a-chloro ketone under basic conditions to give the 4,8-dialkyl-7-(2-oxoalkoxy)coumarin. Cyclization of this intermediate to the 4,4',8-trialkylcoumarin occurs by heating in aqueous base. Under identical conditions to those described above for introducing a primaryamino-substituted side chain, the 4,4', 8-trialkylpsoralens can be converted to the 5'-(w-haloalkyl)-4,4',8'trialkylpsoralens, (herein called 5'-HATP), (Kaufman, U.S. Pat. Nos. 4,294,822 and 4,298,614). Again, this formation of extended-chain primary amines in which the terminal amine is linked to the psoralen by a bridge containing one or more oxygen or nitrogen atoms is a novel approach.

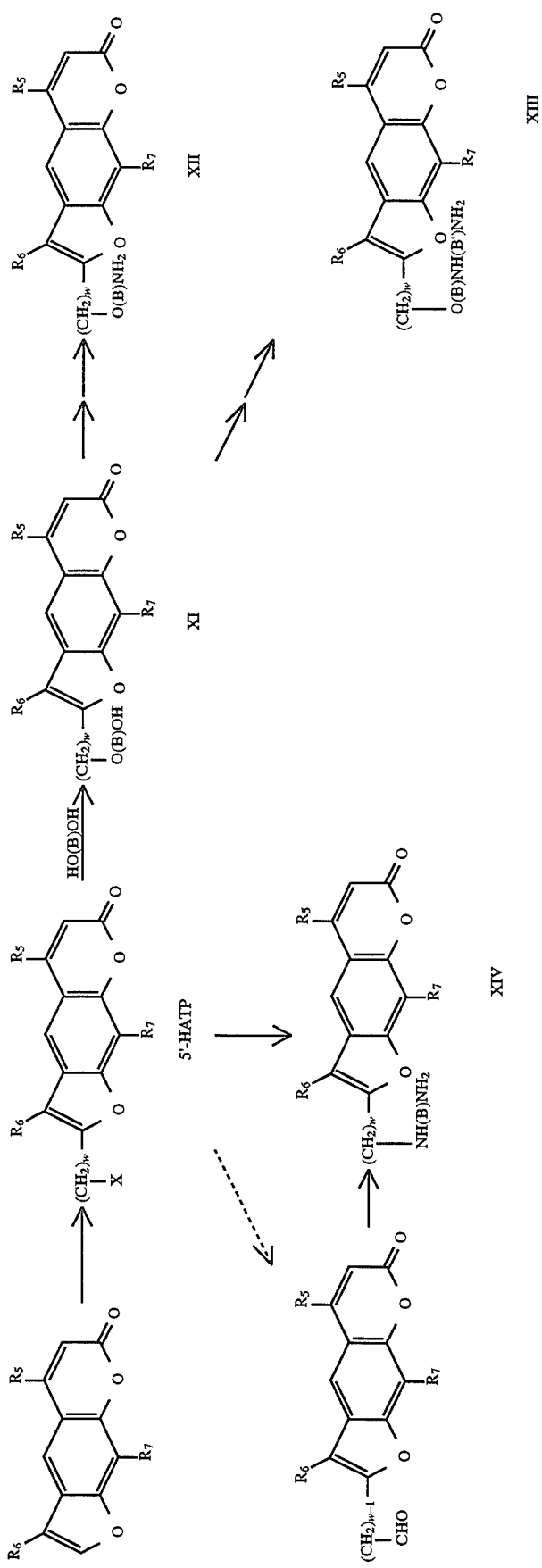

The discussion of the conversion of 4,4',8-trialkylpsoralens to 5'-primaryamino-substituted-4,4',8-trialkylpsoralens applies equally well when the 4- and/or 8-position is just substituted with a hydrogen, thus providing 5'-primaryamino-substituted-4', (4 or 8)- dialkylpsoralens and 5'-primaryamino-substituted-4'-alkylpsoralens.

Referring back to the synthesis of 4' (or 5')-halomethyl-4, 5' (or 4'),8-trialkyl psoralens, the preparation of these critical intermediates in the synthesis of several compounds presents difficult challenges. The known method of preparation involves treatment of the starting psoralen with 50–200 equivalents of highly toxic, and volatile chloromethyl methyl ether or bromomethyl methyl ether. Yields of only 30–60% of the desired intermediate are obtained. Described herein, is a much improved procedure which allows for the synthesis of either isomer of the bromomethyl-trialkylpsoralens by careful control of reaction conditions.

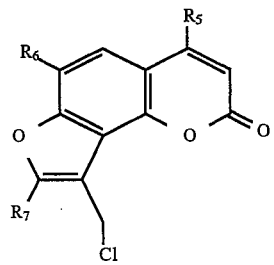

IXX

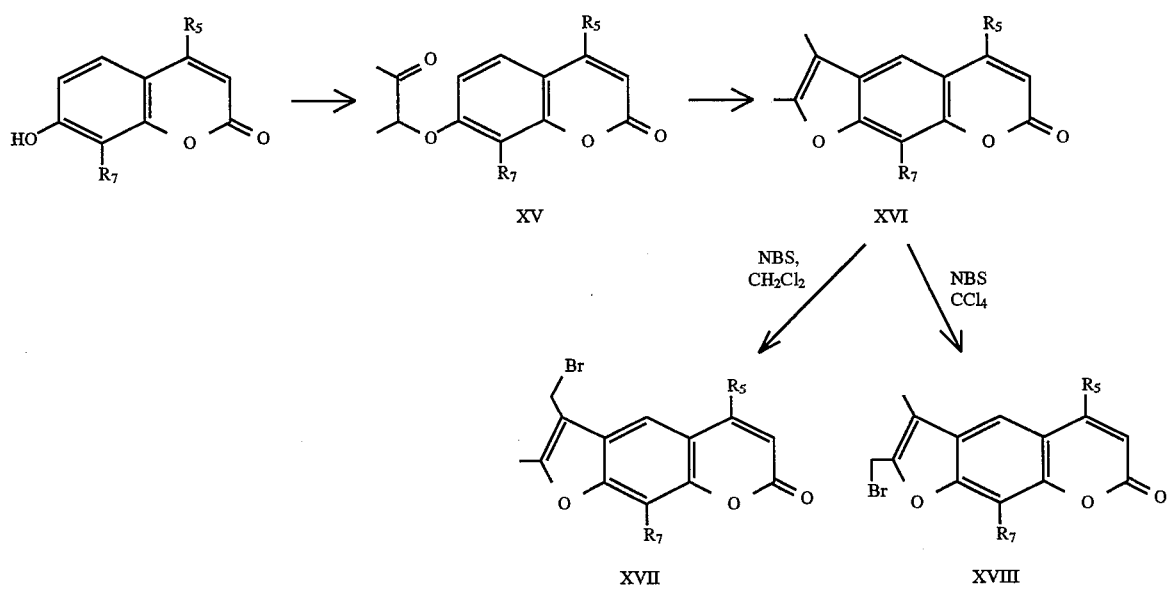

Reaction of the 4,8-dialkyl-7-hydroxycoumarin with 2-chloro-3-butanone under typical basic conditions, provides 4,8-dialkyl-7-(1-methyl-2-oxopropyloxy)coumarin (XV). This material is heated in aqueous NaOH to provide 4,8-dialkyl-4',5'-dimethylpsoralen (XVI). The tetrasubstitued psoralen and N-bromosuccinimide are then refluxed in a solvent, preferably with a catalyst such as benzoyl peroxide. If the solvent used is carbon tetrachloride, 4,8-dialkyl-5'-bromomethyl-4'-methylpsoralen (XVIII) is obtained in greater than 66% yield. If methylene chloride is used, only 4,8-dialkyl-4'-bromomethyl-5'-methylpsoralen (XVII) is obtained in ≥80% yield. Benzylic bromination in other solvents can also be done, generating one of the isomeric products alone or in a mixture. These solvents include, but are not limited to, chloroform, bromotrichloromethane and benzene.

The discussion above of the syntheses of 4'-primaryamino- and 5'-primaryamino-psoralens can be extended to the non-linear coumarins, specifically the isopsoralens or angelicins. Thus, the 4'-chloromethylangelicins (IXX) and the 5'-chloromethylangelicins (XX) can be prepared in a similar manner to their linear counterparts. By analogy with the synthetic pathways presented above one can envision the synthesis of 4'-(w-amino)alkylangelicins and 5'-(w-amino)alkylan gelicins where the alkyl linkage can contain one or more oxygen or nitrogen atoms.

-continued

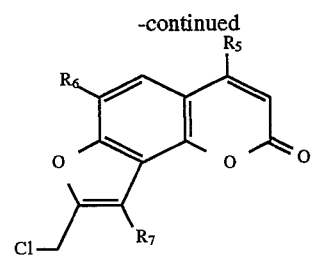

XX

III. BINDING OF COMPOUNDS TO NUCLEIC ACID

The present invention contemplates binding new and known compounds to nucleic acid, including (but not limited to) viral nucleic acid and bacterial nucleic acid. One approach of the present invention to binding photoactivation compounds to nucleic acid is photobinding. Photobinding is defined as the binding of photobinding compounds in the presence of photoactivating wavelengths of light. Photobinding compounds are compounds that bind to nucleic acid in the presence of photoactivating wavelengths of light. The present invention contemplates methods of photobinding with photobinding compounds of the present invention.

One embodiment of the method of the present invention for photobinding involves the steps: a) providing a photobinding compound of the present invention; and b) mixing the photobinding compound with nucleic acid in the presence of photoactivation wavelengths of electromagnetic radiation.

The invention further contemplates a method for modifying nucleic acid, comprising the steps: a) providing photobinding compound of the present invention and nucleic acid; and b) photobinding the photobinding compound to the nucleic acid, so that a compound:nucleic acid complex is formed.

IV. INACTIVATION OF PATHOGENS

The present invention contemplates treating a blood product with a photoactivation compound and irradiating to inactivate contaminating pathogen nucleic acid sequences before using the blood product.

A. Inactivation in General

The term "inactivation" is here defined as the altering of the nucleic acid of a unit of pathogen so as to render the unit of pathogen incapable of replication. This is distinct from "total inactivation", where all pathogen units present in a given sample are rendered incapable of replication, or "substantial inactivation," where most of the pathogen units present are rendered incapable of replication. "Inactivation efficiency" of a compound is defined as the level of inactivation the compound can achieve at a given concentration of compound or dose of irradiation. For example, if 100 µM of a hypothetical compound X inactivated 5 logs of HIV virus whereas under the same experimental conditions, the same concentration of compound Y inactivated only 1 log of virus, then compound X would have a better "inactivation efficiency" than compound Y.

To appreciate that an "inactivation" method may or may not achieve "total inactivation," it is useful to consider a specific example. A bacterial culture is said to be inactivated if an aliquot of the culture, when transferred to a fresh culture plate and permitted to grow, is undetectable after a certain time period. A minimal number of viable bacteria must be applied to the plate for a signal to be detectable. With the optimum detection method, this minimal number is 1 bacterial cell. With a suboptimal detection method, the minimal number of bacterial cells applied so that a signal is observed may be much greater than 1. The detection method determines a "threshold" below which the "inactivation method" appears to be completely effective (and above which "inactivation" is, in fact, only partially effective).

B. Inactivation of Potential Pathogens

The same considerations of detection method and threshold are present when determining the sensitivity limit of an inactivation method for nucleic acid. Again, by "inactivation" it is meant that a unit of pathogen is rendered incapable of replication.

In the case of inactivation methods for material to be used by humans, whether in vivo or in vitro, the detection method can theoretically be taken to be the measurement of the level of infection with a disease as a result of exposure to the material. The threshold below which the inactivation method is complete is then taken to be the level of inactivation which is sufficient to prevent disease from occurring due to contact with the material. It is recognized that in this practical scenario, it is not essential that the methods of the present invention result in "total inactivation". That is to say, "substantial inactivation" will be adequate as long as the viable portion is insufficient to cause disease. The inactivation method of the present invention renders nucleic acid in pathogens substantially inactivated. In one embodiment, the inactivation method renders pathogen nucleic acid in blood preparations substantially inactivated.

Without intending to be limited to any method by which the compounds of the present invention inactivate pathogens, it is believed that inactivation results from light induced binding of psoralens to pathogen nucleic acid. Further, while it is not intended that the inactivation method of the present invention be limited by the nature of the nucleic acid; it is contemplated that the inactivation method render all forms of nucleic acid (whether DNA, mRNA, etc.) substantially inactivated.

In the case of photoactivation compounds modifying nucleic acid, it is preferred that interaction of the pathogen nucleic acid (whether DNA, mRNA, etc.) with the photoactivation compound causes the pathogen to be unable to replicate, such that, should a human be exposed to the treated pathogen, infection will not result.

"Synthetic media" is herein defined as an aqueous synthetic blood or blood product storage media. In one embodiment, the present invention contemplates inactivating blood products in synthetic media. This method reduces harm to blood products and permits the use of much lower concentrations of photoactivation compounds.

The psoralen photoinactivation method inactivates nucleic acid based pathogens present in blood through a single procedure. Thus, it has the potential to eliminate bacteria, protozoa, and viruses as well. Had an effective decontamination method been available prior to the advent of the AIDS pandemic, no transfusion associated HIV transmission would have occurred. Psoralen-based decontamination has the potential to eliminate all infectious agents from the blood supply, regardless of the pathogen involved. Additionally, psoralen-based decontamination has the ability to sterilize blood products after collection and processing, which in the case of platelet concentrates could solve the problem of low level bacterial contamination and result in extended storage life. Morrow J. F., et al., JAMA 266:555–558 (1991); Bertolini F., et al., Transfusion 32:152–156 (1992).

TABLE 2

| Viruses Photochemically Inactivated by Psoralens | |
|---|---|
| Family | Virus |
| Adeno | Adenovirus 2 |
| | Canine Hepatitis |
| Arena | Pichinde |
| | Lassa |
| Bunya | Turlock |
| | California Encephalitis |
| | Herpes Simplex 1 |
| Herpes | Herpes Simplex 2 |
| | Cytomegalovirus |
| | Pseudorabies |
| Orothomyxo | Influenza |
| Papova | SV-40 |
| Paramyxo | Measles |
| | Mumps |
| | Parainfluenza 2 and 3 |
| Picorna[1] | Poliovirus 1 and 2 |
| | Coxsackie A-9 |
| | Echo 11 |
| Pox | Vaccinia |
| | Fowl Pox |
| Reo | Reovirus 3 |
| | Blue Tongue |
| | Colorado Tick Fever |
| Retro | HIV |
| | Avian Sarcoma |
| | Murine Sarcoma |
| | Murine Leukemia |
| Rhabdo | Vesticular Stomatitis Virus |

TABLE 2-continued

Viruses Photochemically Inactivated by Psoralens

| Family | Virus |
| --- | --- |
| Toga | Western Equine Encephalitis |
|  | Dengue 2 |
|  | Dengue 4 |
|  | St. Louis Encephalitis |
| Hepadna | Hepatitis B |
| Bacteriophage | Lambda |
|  | T2 |
| (Rickettsia) | R. Akari (Rickettsialpox) |

[1] In the article, it was pointed out that Piconaviruses were photoinactivated only if psoralens were present during virus growth.

A list of viruses which have been photochemically inactivated by one or more psoralen derivatives appears in Table 2. (From Table 1 of Hanson, C. V., Blood Cells 18:7 (1992)). This list is not exhaustive, and is merely representative of the great variety of pathogens psoralens can inactivate. The present invention contemplates the inactivation of these and other viruses by the compounds described herein. The compounds of the present invention are particularly well suited for inactivating envelope viruses, such as the HIV virus.

C. Selecting Photoctivation Compounds for Inactivation of Pathogens

In order to evaluate a compound to decide if it would be useful in the methods of the present invention, two important properties should be considered: the compound's ability to inactivate pathogens and its mutagenicity. The ability of a compound to inactivate pathogens may be determined by several methods. One technique is to perform a bacteriophage screen; an assay which determines nucleic acid binding of test compounds. A screen of this type, an R17 screen, is described in detail in EXAMPLE 9, below. Another technique is to perform a viral screen, as shown in detail in EXAMPLE 10 for HIV, and EXAMPLE 11 for Duck Hepatitis B Virus.

The R17 bacteriophage screen is believed to be predictive of HIV inactivation efficiency, as well as the efficiency of compounds against many other viruses. R17 was chosen because it was expected to be a very difficult pathogen to inactivate. It is a small, single stranded RNA phage. Without intending to be limited to any means by which the present invention operates, it is expected that shorter pieces of nucleic acid are harder to inactivate because they require a higher frequency of formation of psoralen adducts than do longer pieces of nucleic acid. Further, single stranded RNA pathogens are more difficult to inactivate because psoralens can neither intercalate between base pairs, as with double-stranded nucleic acids, nor form diadducts which function as interstrand crosslinks. Thus it is expected that when inactivation of R17 is achieved, these same conditions will cause the inactivation of many viruses and bacteria.

The second property that is important in testing a compound for use in methods of the present invention is mutagenicity. The most widely used mutagen/carcinogen screening assay is the Ames test. This assay is described by D. M. Maron and B. N. Ames in Mutation Research 113:173 (1983). The Ames test utilizes several unique strains of *Salmonella typhimurium* that are histidine- dependent for growth and that lack the usual DNA repair enzymes. The frequency of normal mutations that render the bacteria independent of histidine (i.e., the frequency of spontaneous revertants) is low. Thus, the test can evaluate the impact of a compound on this revertant frequency.

Because some substances are not mutagenic by themselves, but are converted to a mutagen by metabolic action, the compound to be tested is mixed with the bacteria on agar plates along with the liver extract. The liver extract serves to mimic metabolic action in an animal. Control plates have only the bacteria and the extract.

The mixtures are allowed to incubate. Growth of bacteria (if any) is checked by counting colonies. A positive Ames test is one where the number of colonies on the plates with mixtures containing the compound significantly exceeds the number on the corresponding control plates.

When known carcinogens are screened in this manner with the Ames test, approximately ninety percent are positive. When known noncarcinogens are similarly tested, approximately ninety percent are negative. By performing these screens, a person skilled in the art can quickly determine which compounds would be appropriate for use in methods of the present invention.

D. Delivery of Compounds for Photoinactivation

The present invention contemplates several different formulations and routes by which the compounds described herein can be delivered in an inactivation method. This section is merely illustrative, and not intended to limit the invention to any form or method of introducing the compound.

The compounds of the present invention may be introduced in an inactivation method in several forms. The compounds may be introduced as an aqueous solution in water, saline, a synthetic media such as "Sterilyte™", or a variety of other solvents. The compounds can further be provided as dry formulations, with or without adjuvants.

The new compounds may also be provided by many different routes. For example, the compound may be introduced to the reaction vessel, such as a blood bag, at the point of manufacture. Alternatively, the compound may be added to the material to be sterilized after the material has been placed in the reaction vessel. Further, the compounds may be introduced alone, or in a "cocktail" or mixture of several different compounds.

V. PRESERVATION OF BIOCHEMICAL PROPERTIES OF MATERIAL TREATED

Psoralens are useful in inactivation procedures, because the reaction can be carried out at temperatures compatible with retaining biochemical properties of blood and blood products. Hanson, C. V., Blood Cells 18:7 (1992). The inactivation compounds and methods of the present invention are especially useful because they display the unlinking of pathogen inactivation efficiency from mutagenicity. The compounds exhibit powerful pathogenic inactivation without a concomitant rise in mutagenicity. The commonly known compounds tested in photoinactivation protocols, such as AMT, appear to exhibit a link between pathogen inactivation efficiency and mutagenetic action that until now seemed indivisible.

While it is not intended that the present invention be limited to any theory by which pathogen inactivation efficiency is unlinked from mutagenicity, it is postulated that unlinking occurs as a result of the length of the groups substituted on the psoralen, and the location of charges on the compounds. It is postulated that positive charges on one or both ends of mutagenic compounds have non-covalent interactions with the phosphate backbone of DNA. These interactions are presumed to occur independent of the presence of light (called "dark binding"). In theory, the psoralen thereby sterically blocks polymerase from opening up the DNA, causing mutagenicity. In contrast, compounds of the present invention carry a positive or neutral charge on a long substitute group. These substituted groups form a steric barrier during dark binding that is much easier to free from the DNA, permitting polymerase to pass. Thus no mutagenicity results.

EXPERIMENTAL

The following examples serve to illustrate certain preferred embodiments and aspects of the present invention and are not to be construed as limiting the scope thereof.

In the experimental disclosure which follows, the following abbreviations apply: eq (equivalents); M (Molar); µM (micromolar); N (Normal); mol (moles); mmol (millimoles); µmol (micromoles); nmol (nanomoles); g (grams); mg (milligrams); µg (micrograms); Kg (kilograms); L (liters); mL (milliliters); µL (microliters); cm (centimeters); mm (millimeters); µm (micrometers); nm (nanometers); J (Joules, note that in FIGS. 6, 8–17, Joules or J refers to Joules/cm$^2$); °C. (degrees Centigrade); TLC (Thin Layer Chromatography); EAA (ethylacetoacetate); EtOH (ethanol); HOAc (acetic acid); W (watts); mW (milliwatts); NMR (Nuclear Magnetic Resonance; spectra obtained at room temperature on a Varian Gemini 200 MHz Fourier Transform Spectrometer); m.p. (melting point); UV (ultraviolet light); THF (tetrahydrofuran); DMEM (Dulbecco's Modified Eagles Medium); FBS (fetal bovine serum); LB (Luria Broth); EDTA (ethelene diamine tetracidic acid).

For ease of reference, some compounds of the present invention have been assigned a number from 1–17. The reference numbers are assigned in FIGS. 5A–5F and appear below the structure of each compound. These reference numbers are used throughout the experimental section.

When isolating compounds of the present invention in the form of an acid addition salt, the acid is preferably selected so as to contain an anion which is non-toxic and pharmacologically acceptable, at least in usual therapeutic doses. Representative salts which are included in this preferred group are the hydrochlorides, hydrobromides, sulphates, acetates, phosphates, nitrates, methanesulphonates, ethanesulphonates, lactates, citrates, tartrates or bitartrates, and maleates. Other acids are likewise suitable and may be employed as desired. For example, fumaric, benzoic, ascorbic, succinic, salicylic, bismethylenesalicylic, propionic, gluconic, malic, malonic, mandelic, cinnamic, citraconic, stearic, palmitic, itaconic, glycolic, benzenesulphonic, and sulphamic acids may also be employed as acid addition salt-forming acids.

In one of the examples below, phosphate buffered synthetic media is formulated for platelet treatment. This can be formulated in one step, resulting in a pH balanced solution (e.g., pH 7.2), by combining the following reagents in 2 liters of distilled water:

Preparation of Sterilyte ™ 3.0

| | Formula W. | mMolarity | Grams/2 Liters |
|---|---|---|---|
| NaAcetate*3H$_2$O | 136.08 | 20 | 5.443 |
| Glucose | 180.16 | 2 | 0.721 |
| D-mannitol | 182.17 | 20 | 7.287 |
| KCl | 74.56 | 4 | 0.596 |
| NaCl | 58.44 | 100 | 11.688 |
| Na$_3$ Citrate | 294.10 | 10 | 5.882 |
| Na$_2$HPO$_4$*7H$_2$O | 268.07 | 14.46 | 7.752 |
| NaH$_2$PO$_4$*H$_2$O | 137.99 | 5.54 | 1.529 |
| MgCl$_2$*6H$_2$O | 203.3 | 2 | 0.813 |

The solution is then mixed, sterile filtered (0.2 micron filter) and refrigerated.

The Polymerase Chain Reaction (PCR) is used in one of the examples to measure whether viral inactivation by some compounds was complete. PCR is a method for increasing the concentration of a segment of a target sequence in a mixture of genomic DNA without cloning or purification. See K. B. Mullis et al., U.S. Pat. Nos. 4,683,195 and 4,683,202, hereby incorporated by reference. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then to annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to by the inventors as the "Polymerase Chain Reaction". Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P labeled deoxynucleotide triphosphates, e.g., dCTP or dATP, into the amplified segment). In addition to genomic DNA, any oligonucleotide sequence can be amplified with the appropriate set of primer molecules.

The PCR amplification process is known to reach a plateau concentration of specific target sequences of approximately $10^{-8}$M. A typical reaction volume is 100 µl, which corresponds to a yield of $6 \times 10^{11}$ double stranded product molecules.

PCR is a polynucleotide amplification protocol. The amplification factor that is observed is related to the number (n) of cycles of PCR that have occurred and the efficiency of replication at each cycle (E), which in turn is a function of the priming and extension efficiencies during each cycle. Amplification has been observed to follow the form $E^n$, until high concentrations of PCR product are made. At these high concentrations (approximately $10^{-8}$M/l) the efficiency of replication falls off drastically. This is probably due to the displacement of the short oligonucleotide primers by the longer complementary strands of PCR product. At concentrations in excess of $10^{-8}$M, the rate of the two complementary PCR amplified product strands finding each other during the priming reactions become sufficiently fast that this occurs before or concomitant with the extension step of the PCR procedure. This ultimately leads to a reduced priming efficiency, and therefore, a reduced cycle efficiency. Continued cycles of PCR lead to declining increases of PCR product molecules. PCR product eventually reaches a plateau concentration.

The sequences of the polynucleotide primers used in this experimental section are as follows:

DCD03: 5' ACT AGA AAA CCT CGT GGA CT 3'

DCD05: 5' GGG AGA GGG GAG CCC GCA CG 3'
DCD06: 5' CAA TTT CGG GAA GGG CAC TC 3'
DCD07: 5' GCT ACT ATT CCC CCG AAG GT 3'

With DCD03 as a common forward primer, the pairs generate amplicons of length 127, 327, and 1072 bp. These oligos were selected from regions that are absolutely conserved between 5 different dHBV isolates (DHBV1, DHBV3, DHBV16, DHBV22, and DHBV26) as well as from heron HBV (HHBV4).

The following examples serve to illustrate certain preferred embodiments and aspects of the present invention and are not to be construed as limiting the scope thereof.

EXAMPLE 1

As noted above, the present invention contemplates devices and methods for the photoactivation of photoreactive nucleic acid binding compounds. In this example, a photoactivation device is described for decontaminating blood products according to the method of the present invention. This device comprises: a) means for providing appropriate wavelengths of electromagnetic radiation to cause photoactivation of at least one photoreactive compound; b) means for supporting a plurality of blood products in a fixed relationship with the radiation providing means during photoactivation; and c) means for maintaining the temperature of the blood products within a desired temperature range during photoactivation.

FIG. 1 is a perspective view of one embodiment of the device integrating the above-named features. The figure shows an opaque housing (100) with a portion of it removed, containing an array of bulbs (101) above and below a plurality of representative blood product containing means (102) placed between plate assemblies (103, 104). The plate assemblies (103, 104) are described more fully, subsequently.

The bulbs (101), which are connectable to a power source (not shown), serve as a source of electromagnetic radiation. While not limited to the particular bulb type, the embodiment is configured to accept an industry standard, dual bipin lamp.

The housing (100) can be opened via a latch (105) so that the blood product can be placed appropriately. As shown in FIG. 1, the housing (100), when closed, completely contains the irradiation from the bulbs (101). During irradiation, the user can confirm that the device is operating by looking through a safety viewport (106) which does not allow transmission of ultraviolet light to the user.

The housing (100) also serves as a mount for several electronic components on a control board (107), including, by way of example, a main power switch, a count down timer, and an hour meter. For convenience, the power switch can be wired to the count down timer which in turn is wired in parallel to an hour meter and to the source of the electromagnetic radiation. The count down timer permits a user to preset the irradiation time to a desired level of exposure. The hour meter maintains a record of the total number of radiation hours that are provided by the source of electromagnetic radiation. This feature permits the bulbs (101) to be monitored and changed before their output diminishes below a minimum level necessary for rapid photoactivation.

Figure 2:
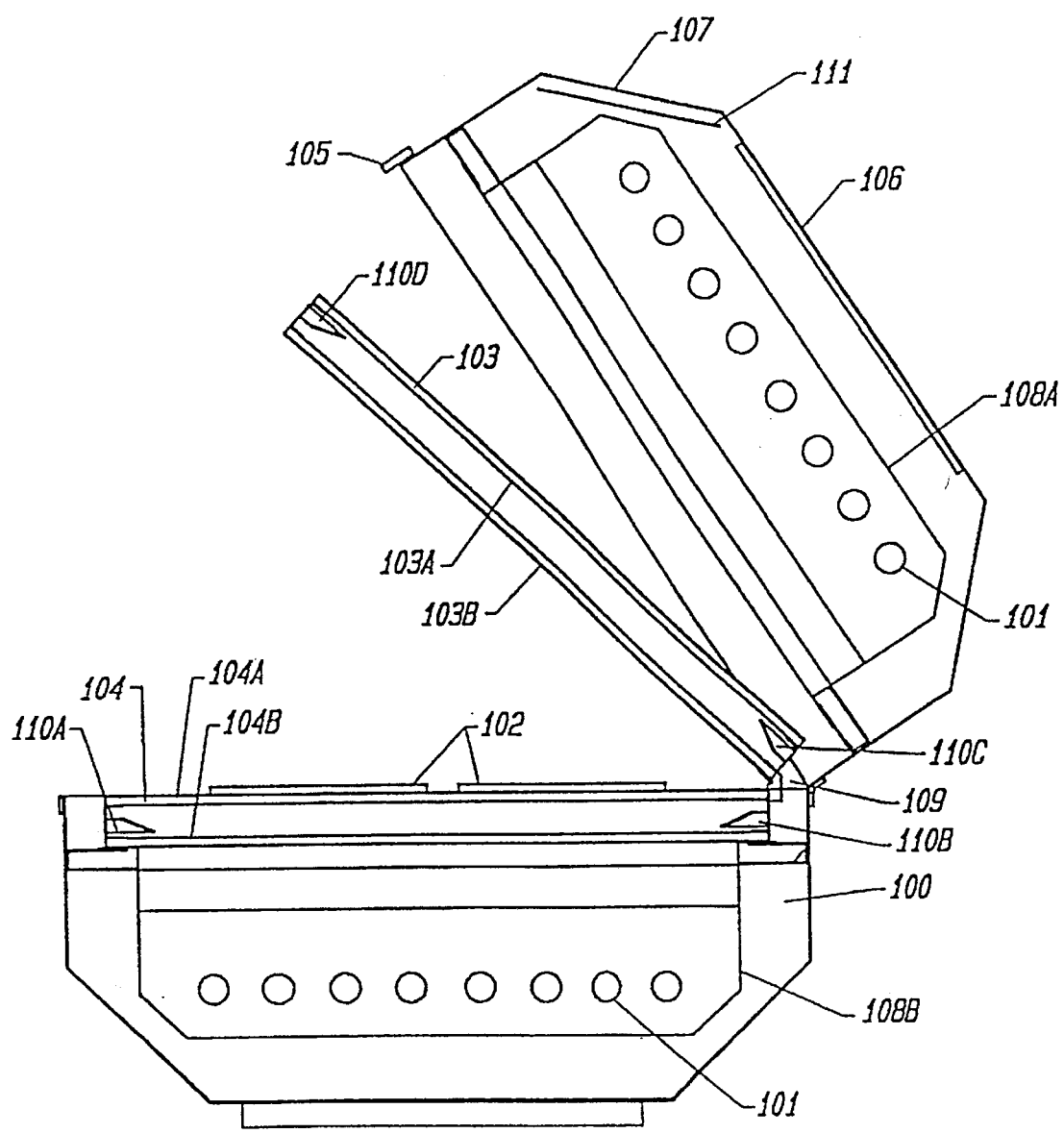
FIG. 2 is a cross-sectional view of the device shown in FIG. 1 along the lines of 2—2.

FIG. 2 is a cross-sectional view of the device shown in FIG. 1 along the lines of 2—2. FIG. 2 shows the arrangement of the bulbs (101) with the housing (100) opened. A reflector (108A, 108B) completely surrounds each array of bulbs (101). Blood product containing means (102) are placed between upper (103) and lower (104) plate assemblies. Each plate assembly is comprised of an upper (103A, 104A) and lower (103B, 104B) plates. The plate assemblies (103, 104) are connected via a hinge (109) which is designed to accommodate the space created by the blood product containing means (102). The upper plate assembly (103) is brought to rest gently on top of the blood product containing means (102) supported by the lower plate (104B) of the lower plate assembly (104).

Detectors (110A, 110B, 110C, 110D) may be conveniently placed between the plates (103A, 103B, 104A, 104B) of the plate assemblies (103, 104). They can be wired to a printed circuit board (111) which in turn is wired to the control board (107).

Figure 3:
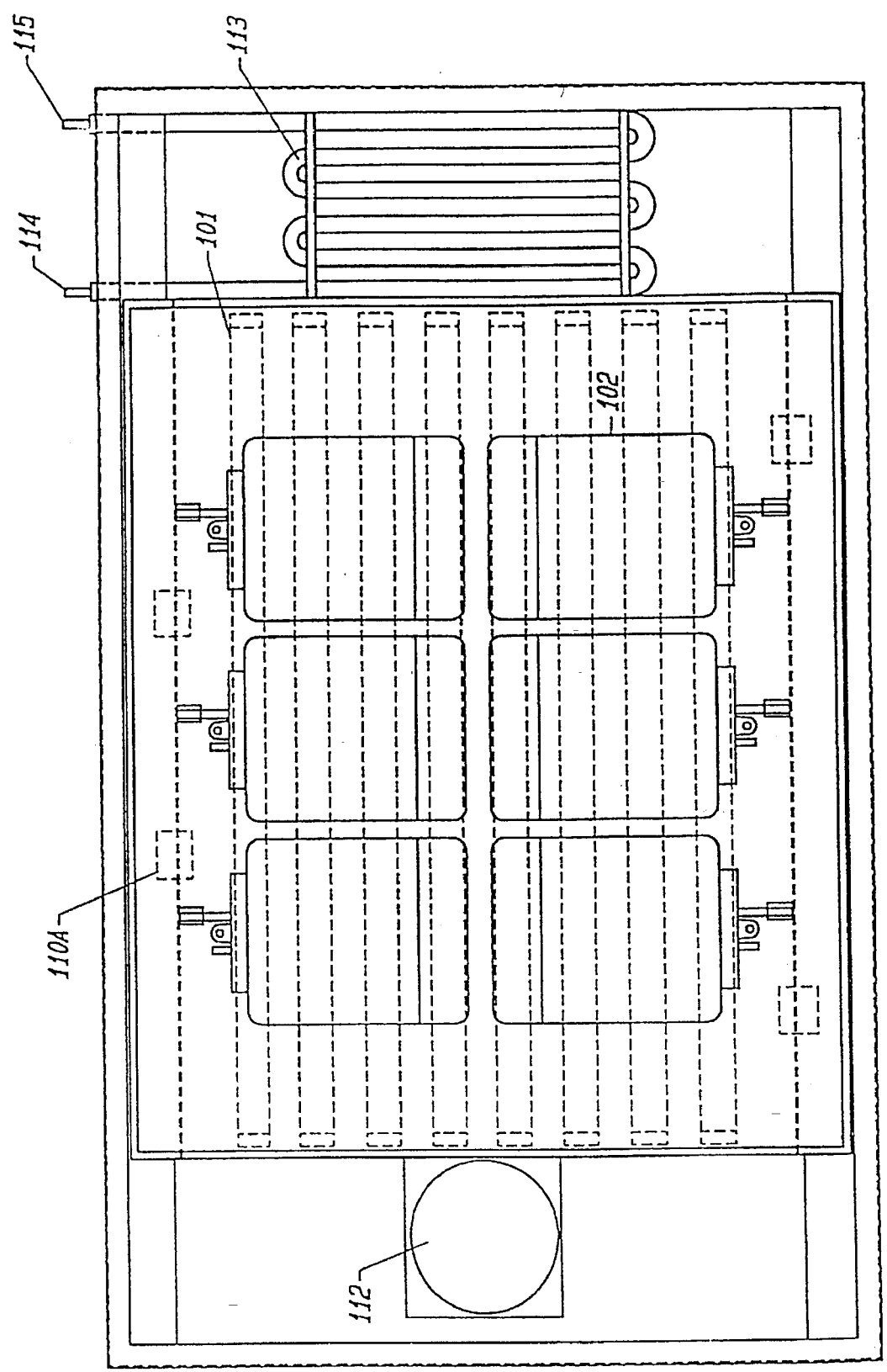
FIG. 3 is a cross-sectional view of the device shown in FIG. 1 along the lines of 3—3.

FIG. 3 is a cross-sectional view of the device shown in FIG. 1 along the lines of 3—3. Six blood product containing means (102) (e.g., Teflon™ platelet unit bags) are placed in a fixed relationship above an array of bulbs (101). The temperature of the blood product can be controlled via a fan (112) alone or, more preferably, by employing a heat exchanger (113) having cooling inlet (114) and outlet (115) ports connected to a cooling source (not shown).

Figure 4:
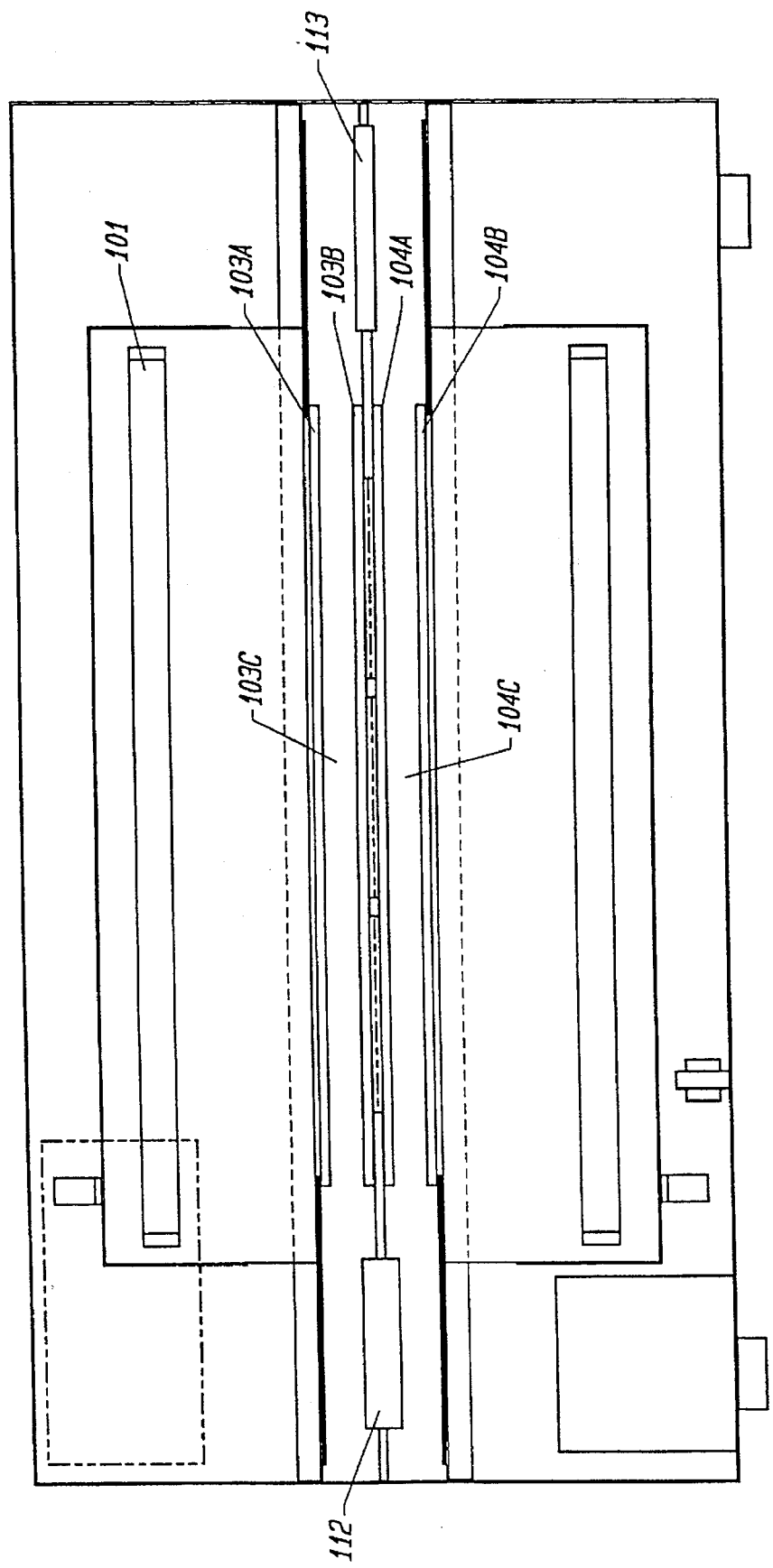
FIG. 4 is a cross-sectional view of the device shown in FIG. 1 along the lines of 4—4.
Figure 5A:
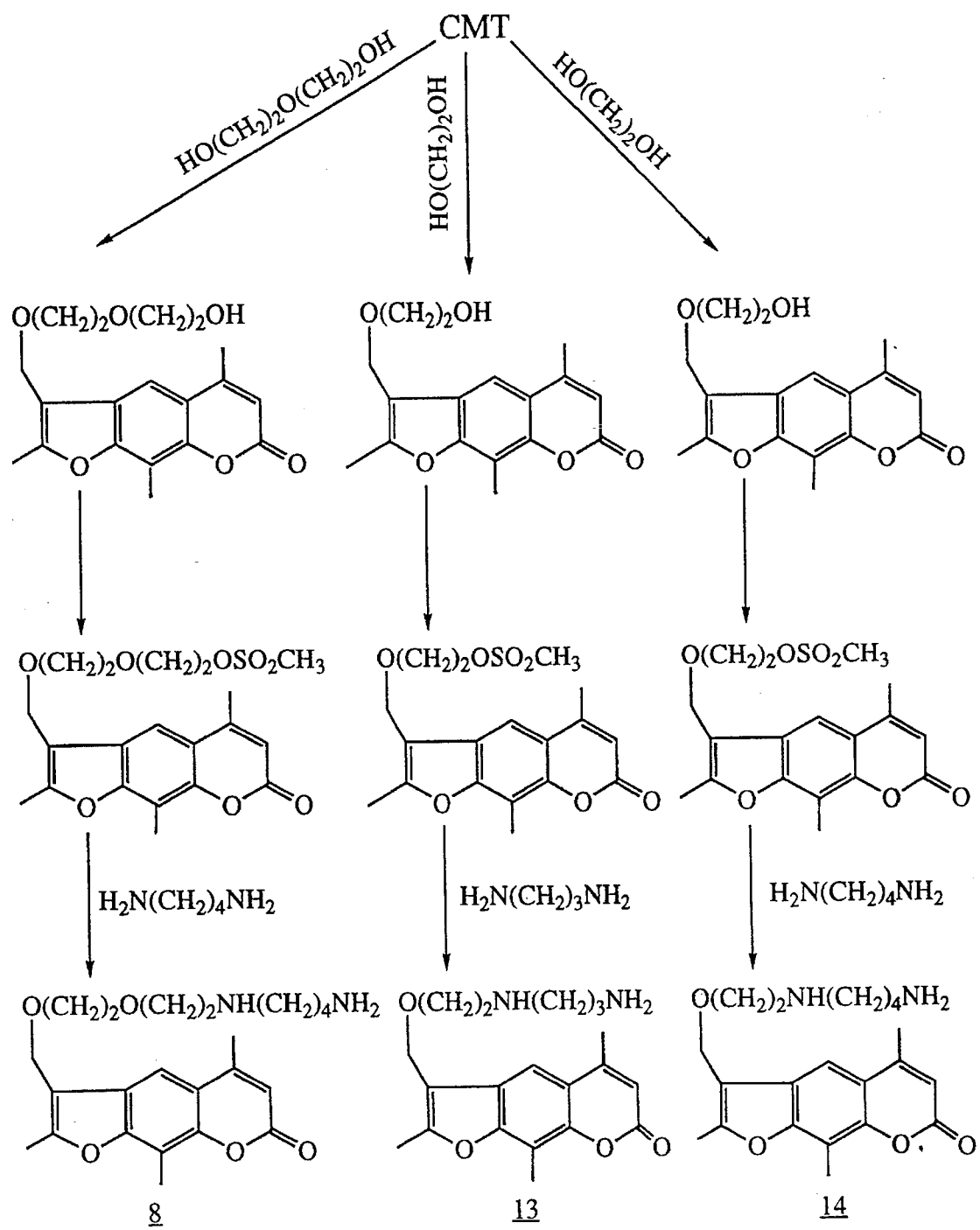
FIG. 5A is a diagram of the synthesis pathways and chemical structures of compounds 8, 13, and 14 of the present invention.
Figure 5B:
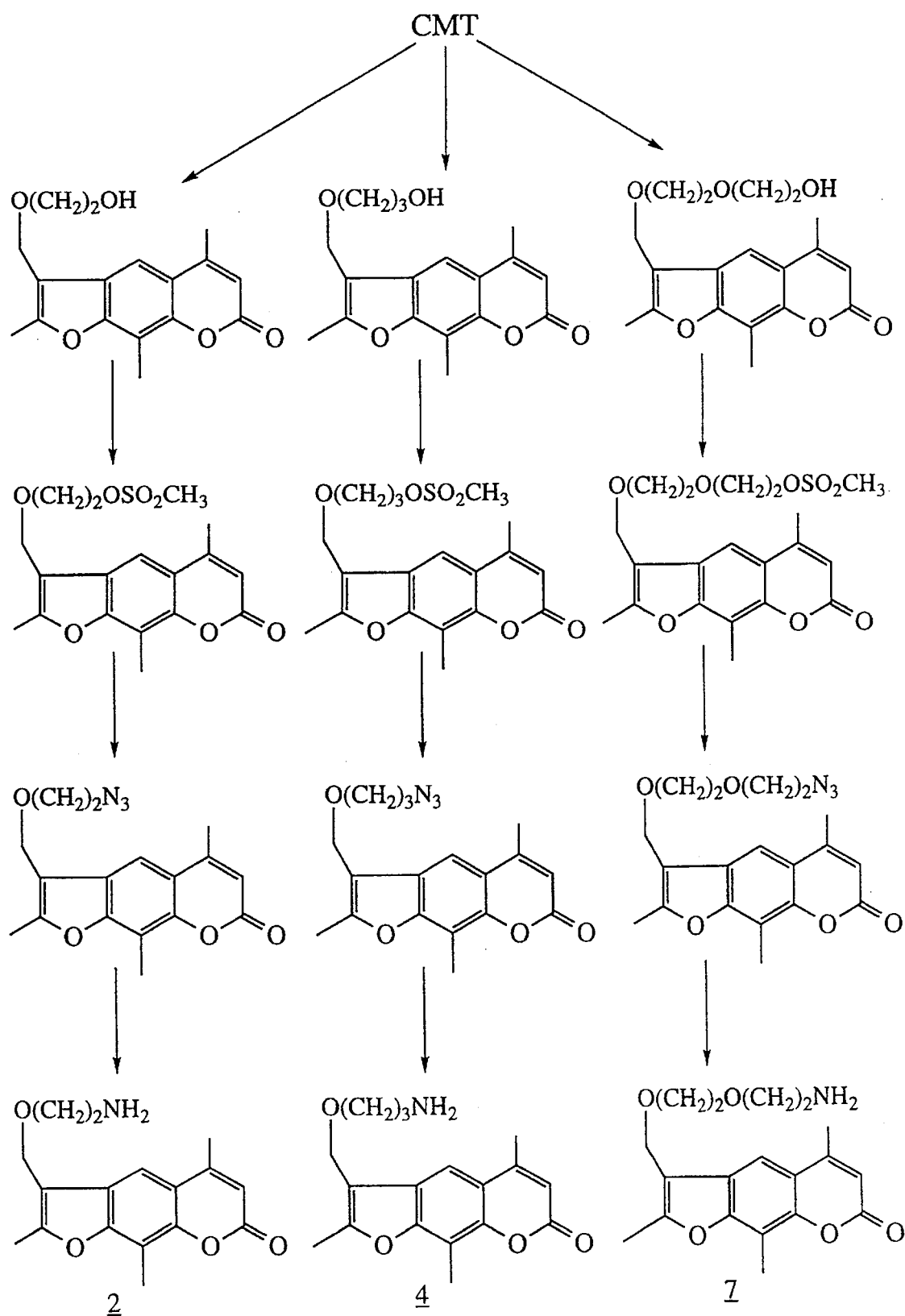
FIG. 5B is a diagram of the synthesis pathways and chemical structures of compounds 2, 4, and 7 of the present invention.
Figure 5C:
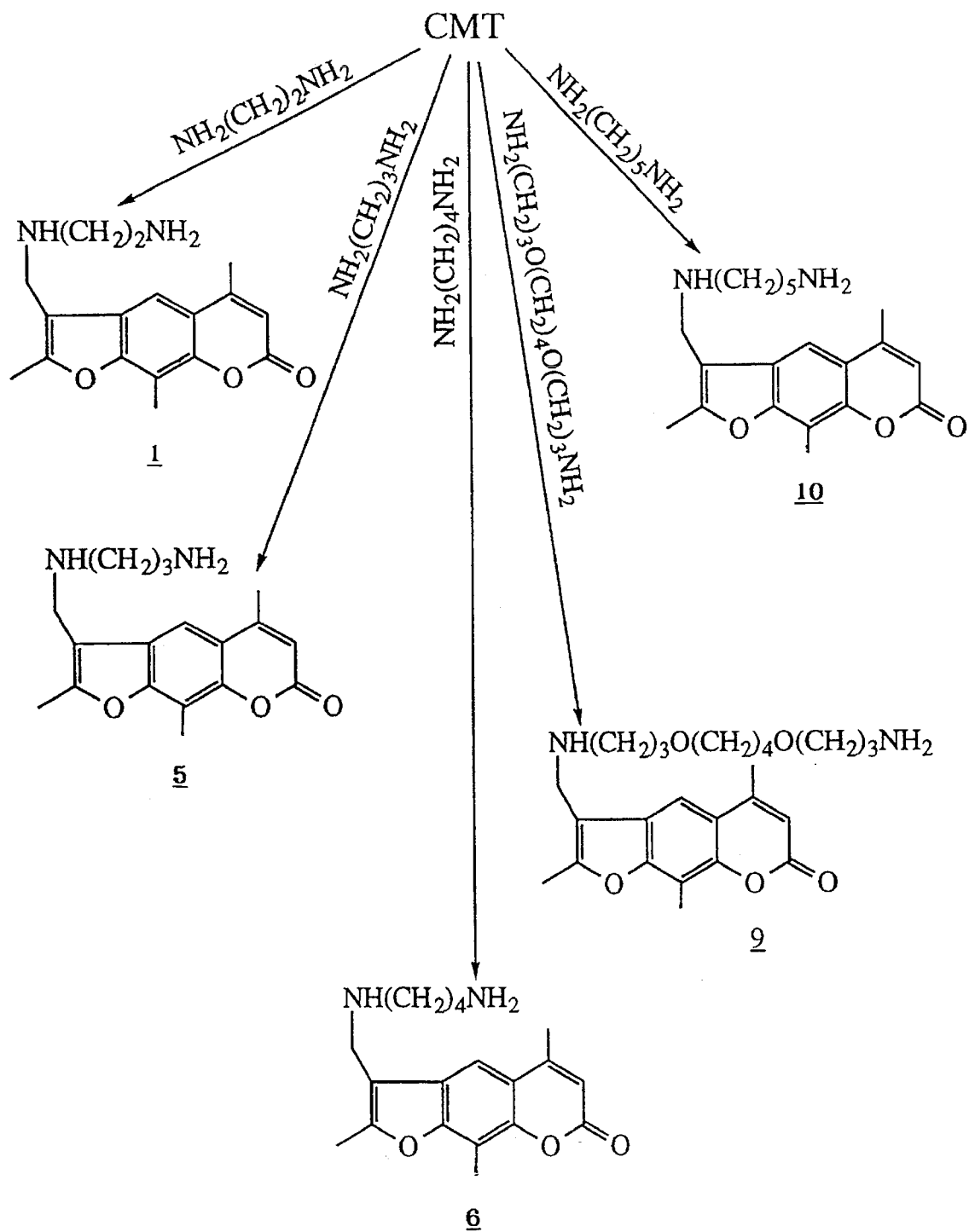
FIG. 5C is a diagram of the synthesis pathways and chemical structures of compounds 1, 5, 6, 9, and 10 of the present invention.
Figure 5D:
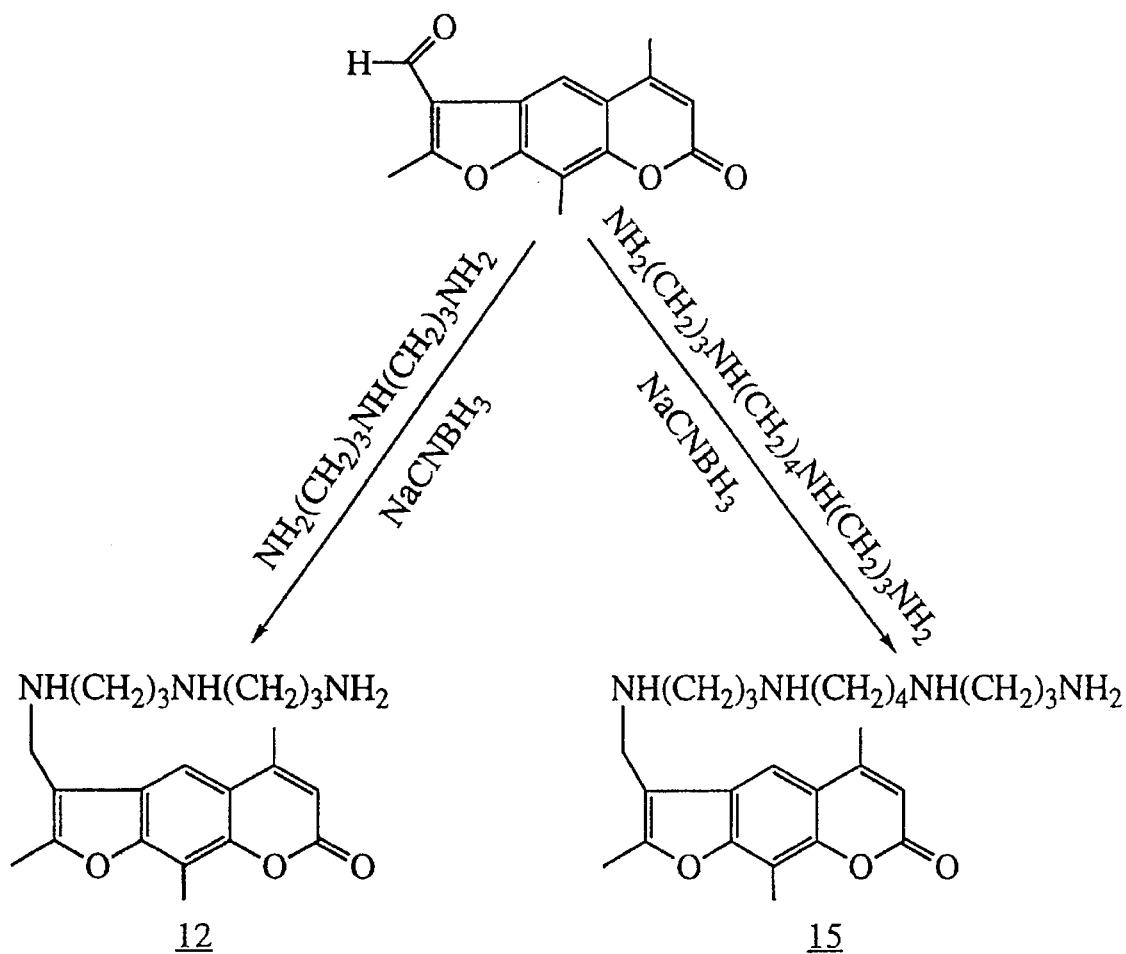
FIG. 5D is a diagram of the synthesis pathways and chemical structures of compounds 12 and 15 of the present invention.
Figure 5E:
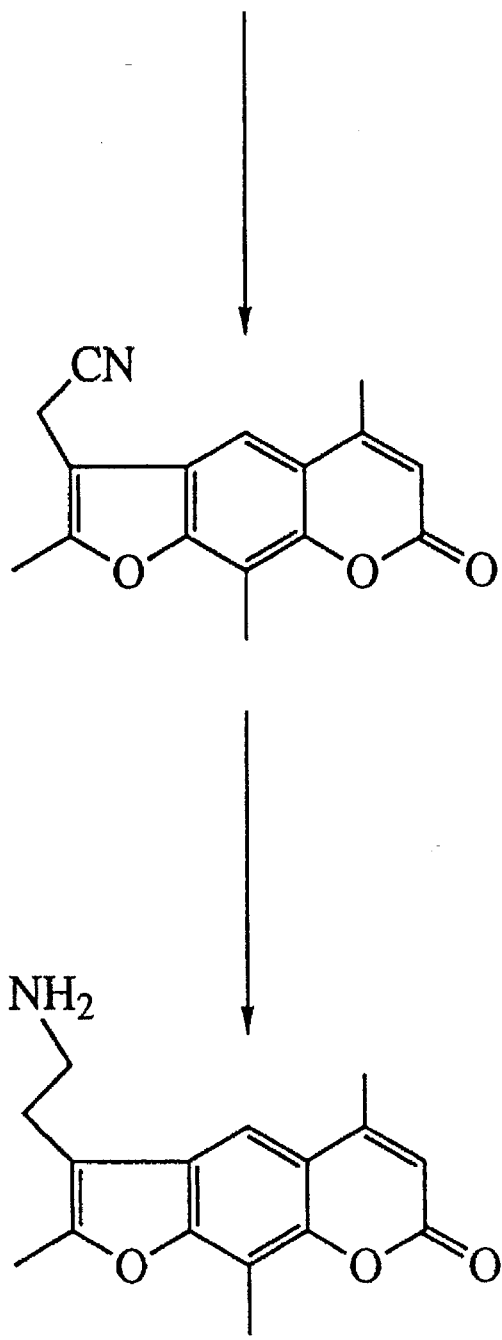
FIG. 5E is a diagram of a synthesis pathways and the chemical structure of compound 3 of the present invention.
Figure 5F:
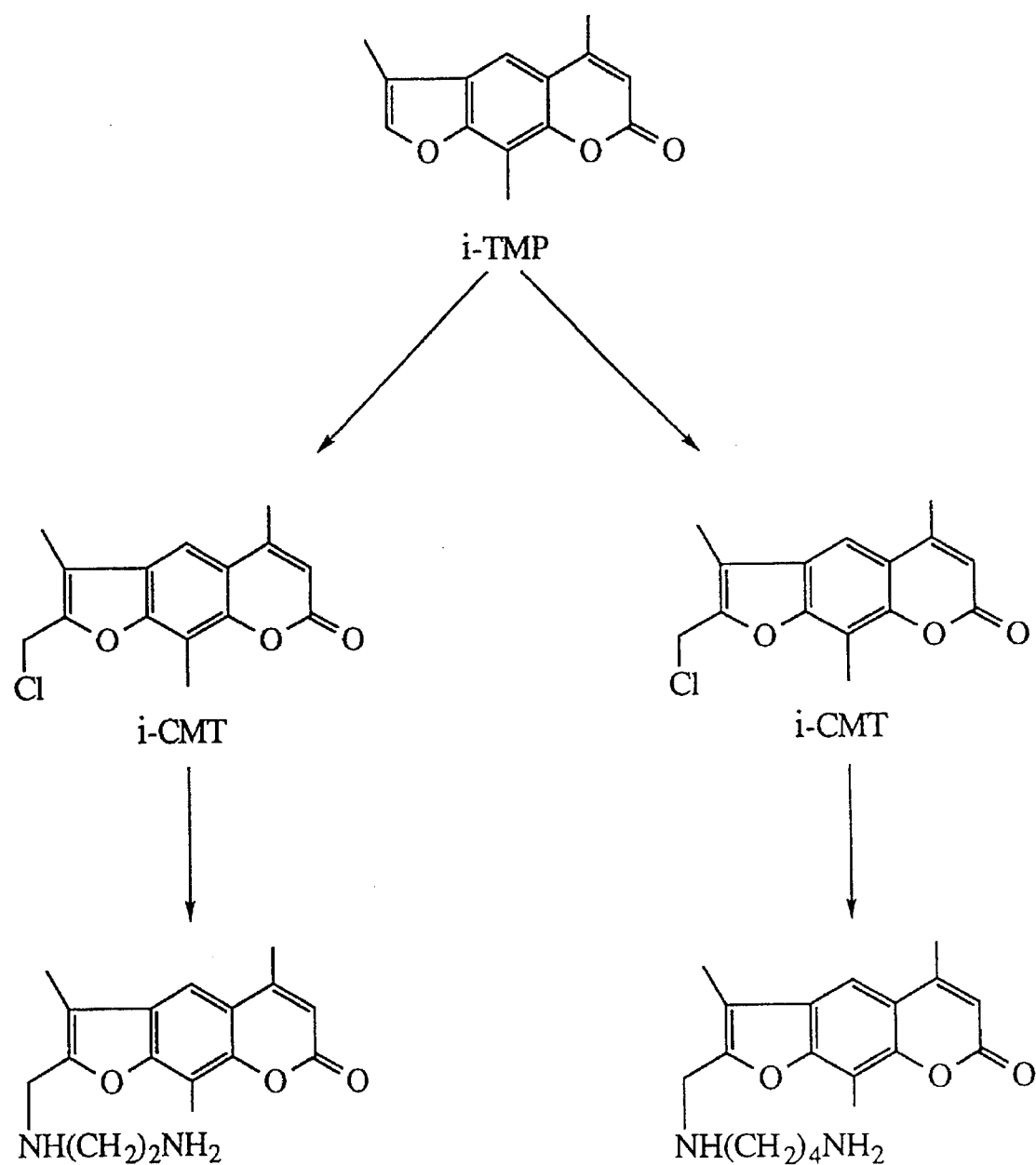
FIG. 5F is a diagram of a synthesis pathways and the chemical structure of compounds 16 and 17 of the present invention.

FIG. 4 is a cross-sectional view of the device shown in FIG. 1 along the lines of 4—4. FIG. 4 more clearly shows the temperature control approach of a preferred embodiment of the device. Upper plate assembly plates (103A, 103B) and lower plate assembly plates (104A, 104B) each create a temperature control chamber (103C, 104C), respectively. The fan (112) can circulate air within and between the chambers (103C, 104C). When the heat exchanger (113) is employed, the circulating air is cooled and passed between the plates (103A, 103B, 104A, 104B).

EXAMPLE 2

Synthesis of 4'-(4-Amino-2-Oxa)Butyl-4,5',8-Trimethylpsoralen Hydrochloride (Compound 2) And Related Compounds (Compound 4)

The preparation of 4'-chloromethyl-4,5',8-trimethylpsoralen from commercially available 4,5',8-trimethylpsoralen has been previously described (U.S. Pat. No. 4,124,598; Isaacs et al., Biochem. 16:1058 (1977)). Reaction of the chloromethyl compound with alcohols (U.S. Pat. No. 4,124,598), pyridine (U.S. Pat. No. 4,169,204), glycol and aminoethanol (U.S. Pat. No. 4,269,852) have all been previously reported. However, compounds in which the 4'-position is substituted with a group, $CH_2$—X—$NH_2$, where X=alkyl or (poly)aza- or oxaalkyl have not been described. The synthesis of 4'-(4-amino-2-oxa)butyl-4,5',8-trimethylpsoralen hydrochloride is achieved in four (4) steps:

STEP 1: 4'-Chloromethyl-4,5',8-trimethylpsoralen (550 mg, 1.99 mmol) and ethylene glycol (6.8 ml, 121.9 mmol) were heated in acetone (6 mL) to 50°–60° C. for 3.5 hrs. After 2 hrs heating, the white suspension had turned to a clear light yellow solution. The acetone and ethylene glycol were removed on the rotoevaporator and water (50 mL) was added to the residue. The resultant suspension was filtered, washed with cold water then dried in the vacuum oven to give 574 mg (96%) of 4'-(4-hydroxy-2-oxa)butyl-4,5',8-trimethylpsoralen; NMR ($CDCl_3$) d: 2.51 (s, 6H); 2.58 (s, 3H); 3.62 (t, J=4.5 Hz, 2H); 3.78 (t, J=4.9 Hz, 2H); 4.70 (s, 2H); 6.26 (d, J=1.1 Hz, 1H); 7.61 (s, 1H).

STEP 2: 4'-(4-hydroxy-2-oxa)butyl-4,5',8-trimethylpsoralen (574 mg, 1.9 mmol) was dissolved in $CH_2Cl_2$ (6 mL) under $N_2$ at ≦10° C. Triethylamine (359 mg, 3.55 mmol) was added. Methanesulfonyl chloride (305 mg, 266 mmol) was dropped in slowly keeping the temperature below 10° C. After addition was completed the mixture was stirred for 15 more minutes and then it was stirred at room temperature for 10 hours. To the reacted suspension $CH_2Cl_2$ (45 mL) was added and the mixture was washed with water (20×3 mL), then dried over anhydrous $Na_2SO_4$. Concentration at $\leq 30°$ C. followed by vacuum drying gave 4'-[(4-methanesulfonyloxy-2-oxa)butyl-4,5',8-trimethylpsoralen as a yellow solid (706 mg, 98%), mp 138°–140° C. NMR d 2.51 (s, 3H); 2.52 (d, 3H); 2.58 (s, 3H); 2.99 (s, 3H); 3.77 (m ,2H); 4.39 (m, 2H); 4.71 (s, 2H); 6.26 (s, 1H); 7.62 (s, 1H).

STEP 3: 4'-[(4-Methanesulfonyloxy-2-oxa)butyl-4,5',8-trimethylpsoralen (706 mg, 1.86 mmol) and sodium azide (241 mg, 3.71 mmol) were refluxed in 95% ethyl alcohol (5 mL) for 8 hours. The reaction solution was cooled and cold water (55 mL) was added. The off-white solid was filtered and washed with cold water. Upon vacuum drying, the azide was obtained as a light yellowish solid (575 mg, 95%), mp 105°–106° C. NMR: d 2.51 (s, 6H); 2.58 (s, 3H); 3.41 (t, J=4.9 Hz, 2H); 3.67 (apparent t, J=4.9 Hz, 2H); 4.70 (s, 2H); 6.26 (s, 1H); 7.66 (s, 1H).

STEP 4: 4'-(4-Azido-2-oxa)butyl-4,5',8-trimethylpsoralen (1.65 g, 5.03 mmol) was dissolved in tetrahydrofuran (10 mL). Triphenylphospine (1.59 g, 6.08 mmol) and six drops of water were added to the foregoing solution. After stirring at room temperature overnight, the light yellow solution was concentrated. The residue was dissolved in $CHCl_3$ (90 mL) and extracted with 0.3N aqueous HCl (30 mL, then 2×5 mL). Combined HCl layers was carefully treated with $K_2CO_3$ until saturated. The base solution was extracted with $CHCl_3$ (3×60 mL). Combined $CHCl_3$ layers were washed with 60 mL of water, 60 mL of brine and dried over anhydrous $Na_2SO_4$. Upon concentration and vacuum drying the amine was obtained as a yellow solid (1.25 g, 82%), mp 139°–141° C.; NMR d 2.48 (s, 6H); 2.55 (s, 3H); 2.89 (t, J=6 Hz, 2H); 3.52 (t, J=6 Hz, 2H); 4.64 (s, 2H); 6.22 (s, 1H); 7.59 (s, 1H).

The amine was dissolved in absolute ethanol (40 mL) and 20 mL of 1N HCl in ethyl ether was added. After sitting at 5° C. overnight, the precipitate was filtered and rinsed with ether to give 1.25 g of Compound 2, mp 236° C. (decomp). Anal. Calculated for $C_{17}H_{20}ClNO_4$: C, 60.45; H, 5.97; N, 4.15. Found: C, 60.27; H, 5.88; N, 4.10.

Similarly prepared was 4'-(5-amino-2-oxa)pentyl-4,5',8-trimethylpsoralen, (Compound 4), m.p. 212°–214° C. (decomposed). NMR of the free base: d 1.73 (pent, J=6.4 Hz, 2H), 2.45 (s, 6H), 2.51 (s, 3H), 2.78 (t, J=6.8 Hz, 2H), 3.54 (t, J=6.2 Hz, 2H), 4.59 (s, 2H), 6.18 (s, 1H), 7.54 (s, 1H).

EXAMPLE 3

Synthesis of 4'-(7-Amino-2,5-Oxa)Heptyl-4,5',8-Trimethylpsoralen Hydrochloride (Compound 7)

The synthesis of 4'-(7-amino-2,5-oxa)heptyl-4,5',8-trimethylpsoralen hydrochloride proceeds in four (4) steps:

STEP 1: 4'-Chloromethyl-4,5',8-trimethylpsoralen (589 mg, 2.13 mmol), diethylene glycol (15.4 g, 145 mmol) and acetone (13 mL) were refluxed for 11.5 hours. The reaction solution was concentrated to remove acetone and part of the diethylene glycol. To the resulting light brown solution was added $CHCl_3$ (40 mL), then washed with water several times. The $CHCl_3$ layer was dried over anhydrous $Na_2SO_4$ and concentrated to give 781 mg of product (~100%). NMR d 2.46 (d, 3H), 2.47 (s, 3H), 2.51 (s, 3H), 3.58–3.67 (m, 8H), 4.67 (s, 2H), 6.18 (s, 1H), 7.57 (s, 1H).

STEP 2: 4'-(7-Hydroxy-2,5-oxa)heptyl-4,5',8-trimethylpsoralen (781 mg, 2.25 mmol) was dissolved in $CH_2Cl_2$ (2.5 mL) under a $N_2$ stream at <10° C. Triethylamine (363 mg, 3.59 mmol) was added. Methanesulfonyl chloride (362 mg, 3.16 mmol) was slowly dropped in to keep the temperature below 10° C. After addition was completed, the mixture was kept below 10° C. for 15 more minutes. The mixture was stirred at room temperature overnight then $CH_2Cl_2$ (50 mL) was added. The solution was washed with water (3×60 mL), dried over anhydrous $Na_2SO_4$ and concentrated at $\leq 30°$ C. Upon vacuum drying, a light brown syrup was obtained; 437 mg (76%). NMR d 2.50 (s, 3H), 2.51 (s, 3H), 2.58 (s, 3H), 3.01 (s, 3H), 3.66 (m, 4H), 3.77 (t, J=4.6 Hz, 2H), 4.37 (t, J=6 Hz, 2H), 4.69 (s, 2H), 6.25 (s, 1H), 7.61 (s, 1H)

STEP 3: 4'-(7-Methanesulfonyloxy-2,5-oxa)heptyl-4,5',8-trimethylpsoralen (288 mg, 0.678 mmol) and sodium azide (88.2 mg, 1.36 mmol) were refluxed in 3 mL of 95% ethyl alcohol for 8 hours. The reaction solution was let cool and cold water (50 mL) was added. The water layer was poured away. The crude material was purified by chromatography on (Silica gel with chloroform eluent) a Chromatotron (Harrison Research, Inc., Palo Alto, Calif.) and vacuum dried to give a light yellow syrup, (123 mg, 49%). NMR d 2.50 (s, 6H), 2.57 (s, 3H), 3.39 (t, J=5.2 Hz, 2H), 3.68 (m, 6H), 4.70 (s, 2H), 6.24 (s, 1H), 7.62 (s, 1H)

STEP 4: 4'-(7-Azido-2,5-oxa)heptyl-4,5',8-trimethylpsoralen (122 mg, 0.33 mmol), triphenylphosphine (129 mg, 0.49 mmol) and several drops of water were dissolved in tetrahydrofuran (2 mL). The light yellow clear solution was stirred at room temperature over a weekend; no starting material was detected by TLC. The reaction solution was concentrated and the residue was dissolved in $CHCl_3$ (20 mL). The solution was extracted with 0.15N aqueous HCl solution (10 mL then 2×5 mL) and the HCl layers was taken to pH 13 by addition of 20% aqueous NaOH solution. The basic solution was extracted with $CHCl_3$ (3×15 mL). The combined $CHCl_3$ layers were washed with water, dried over anhydrous $Na_2SO_4$, concentrated, and vacuum dried to give 63.9 mg of product (56%). TLC showed only one spot. NMR d 2.50 (s, 3H); 2.50 (s, 3H); 2.57 (s, 3H); 2.86 (t, J=5.3 Hz, 2H); 3.50 (t, J=5.3 Hz, 2H); 3.63 (s, 4H); 4.70 (s, 2H); 6.24 (s, 1H); 7.62 (s, 1H). m.p. 170°–173° C.

The solid was dissolved in absolute ethanol, then 1M HCl in ethyl ether was added, the suspension was filtered and the product rinsed with ether and dried.

EXAMPLE 4

Synthesis of 4'-(12-Amino-8-Aza-2,5-Dioxa) dodecyl-4,5',8-Trimethylpsoralen Dihydrochloride (Compound 8)

The synthesis of 4'-(12-amino-8-aza-2,5-dioxa)dodecyl-4,5',8-trimethylpsoralen dihydrochloride proceeds in one (1) step from the product of Example 3, step 2: A solution of 4'-(7-methanesulfonyloxy-2,5-oxa)heptyl-4,5',8-trimethylpsoralen (108 mg, 0.253 mmol) in 8 mL of acetonitrile was slowly added to a solution of 1, 4-diaminobutane (132 mg, 1.49 mmol) in 2.8 mL of acetonitrile. After refluxing for 8 hours, no starting material remained by TLC. The reaction mixture was cooled to room temperature and $CHCl_3$ (25 mL) and 1N aqueous NaOH (25 mL) solution were added. The layers were separated and $CHCl_3$ (2×10 mL) was used to wash the aqueous layer. Aqueous HCl (0.3N, 3×10 mL) was used to extract the product from the combined organics layers. The HCl layers was treated with 20% aqueous NaOH solution until pH 13. The combined basic layers were then extracted with $CHCl_3$ (3×20 mL). The $CHCl_3$ layer was washed with saturated NaCl aqueous solution (10 mL) then dried over anhydrous $Na_2SO_4$. After concentration and vacuum drying, 63 mg of product was obtained (60%). NMR d 1.45 (m, 2H), 2.49 (s, 6H), 2.55 (s, 3H), 2.58 (t, 2H), 2.66 (t, J=5.6 Hz, 2H), 2.76 (m, 4H), 3.55–3.61 (m, 6H), 4.68 (s, 2H), 6.22 (s, 1H), 7.61 (s, 1H).

EXAMPLE 5

Synthesis of 4'-(2-Aminoethyl)-4,5',8-Trimethylpsoralen Hydrochloride (Compound 3)

The synthesis of 4'-(2-aminoethyl)-4,5',8-trimethylpsoralen proceeds in one (1) step: sodium trifluoroacetoxyborohydride was made by adding trifluoroacetic acid (296 mg, 2.60 mmol) in 2 mL of THF to a stirred suspension of sodium borohydride (175 mg, 4.63 mmol) in 2 mL of THF over a period of 10 minutes at room temperature. The resultant suspension was added to a suspension of 4'-cyanomethyl-4,5',8-trimethylpsoralen (Kaufman et al., J. Heterocyclic Chem. 19:1051 (1982)) (188 mg, 0.703 mmol) in 2 mL of THF. The mixture was stirred overnight at room temperature. Several drops of water were added to the reacted light yellow clear solution to decompose the excess reagent under 10° C. The resulting mixture was concentrated and 1N aqueous NaOH solution (30 mL) was added. Chloroform (30 mL then 10 mL, 5 mL)) was used to extract the resultant amine. Combined $CHCl_3$ layers were washed with saturated NaCl solution. The amine was then extracted into aqueous 0.3N HCl (10, 5, 5 mL) and the acid layers were taken to pH 13 with 20% aqueous NaOH. $CHCl_3$ (3×10 mL) was used to extract the amine from the combined base layers then washed with water (2 mL) and dried over anhydrous $Na_2SO_4$. Upon concentration and vacuum drying the amine was obtained as a solid, >95% pure by NMR. NMR d 2.45 (s, 3H); 2.47 (s, 3H); 2.53 (s, 3H); 2.78 (t, J=6.6 Hz, 2H); 3.00 (t, J=6.5 Hz, 2H); 6.20 (s, 1H); 7.44 (s, 1H). The solid was dissolved in absolute ethanol. A solution of hydrogen chloride in diethyl ether (1N, 1 mL) was added. The suspension was filtered to obtain compound 3, a light purple solid (32.7 mg, yield 15%), m.p. >237° C. (decomp.)

EXAMPLE 6

4'-(6-Aminohexyl-2-Aza)-4,5',8-Trimethylpsoralen Dihydrochloride (Compound 6)

The synthesis of 4'-(6-aminohexyl-2-aza)-4,5',8-trimethylpsoralen dihydrochloride proceeds in one (1) step, as follows: a solution of 4'-choromethyl-4,5',8-trimethylpsoralen (188 mg, 0.68 mmol) in 30 mL of acetonitrile was added to a solution of 1,4-diaminobutane (120 mg, 1.4 mmol) in 7 mL of acetonitrile. After stirring overnight the solvent was removed under reduced pressure. Chloroform (10 mL) and 1N NaOH (10 mL) were added to the residue and the mixture was shaken and separated. The aqueous solution was extracted with a further 2×10 mL of $CHCl_3$ and the combined extracts were rinsed with water. The product was then extracted from the $CHCl_3$ solution with 0.3N aqueous HCl and the acidic layer was then taken to pH 12 with concentrated NaOH solution. The base suspension was extracted with $CHCl_3$ which was then rinsed with water, dried over $Na_2SO_4$ and concentrated under reduced pressure to give the amine as the free base; NMR (CDCl3); d 1.33 (m, 3H), 1.52 (m, 4H), 2.47 (s, 3H), 2.49 (d, J=1.1 Hz, 3H), 2.54 (s, 3H), 2.68 (q, J=6.5 Hz, 4H), 3.86 (s, 2H), 6.21 (apparent d, J=1.1 Hz, 1H), 7.60 (s, 1H).

The free base, dissolved in about 6 mL of absolute EtOH was treated with a solution of HCl in ether (1.0M, 3 mL). The resultant HCl salt was filtered, rinsed with absolute EtOH and dried under vacuum to yield 150 mg of compound 6, (55%), m.p. 290° C. (decomposed). Analysis calculated for $C_{19}H_{26}C_{12}N_2O_3 \cdot H_2O$: C, 54.42; H, 6.73; N, 6.68. Found: C, 54.08; H, 6.45; N, 6.65.

Similarly prepared were:

a) 4'-(4-amino-2-aza)butyl-4,5',8-trimethylpsoralen dihydrochloride (Compound 1), mp 320°–322° C. (decomp).

b) 4'-(5-amino-2-aza)pentyl-4,5',8-trimethylpsoralen dihydrochloride (Compound 5), mp 288° C. (decomp). NMR of free base: d 1.33 (br s, 3H), 1.66 (pent, J=6.8 Hz, 2H), 2.47 (s, 3H), 2.50 (d, J=1 Hz, 3H), 2.55 (s, 3H), 2.6–2.85 (m, 4H), 3.89 (s, 2H), 6.22 (apparent d, J=1 Hz, 1H), 7.62 (s, 1H).

c) 4'-(7-amino-2-aza)heptyl-4,5',8-trimethylpsoralen dihydrochloride (Compound 10), mp 300° C. (decomp). NMR of free base: d 1.22 (br s,), 1.3–1.6 (m) total 9H, 2.44 (s), 2.50 (s), total 9H, 2.63 (m, 4H), 6.17 (s, 1H), 7.56 (s, 1H).

EXAMPLE 7

5'-(6-Amino-2-Aza)Hexyl-4,4',8-Trimethylpsoralen Dihydrochloride (Compound 17)

The synthesis of 5'-(6-amino-2-aza)hexyl-4,4',8-trimethylpsoralen dihydrochloride proceeds in one (1) step, as follows: a suspension of 5'-chloromethyl-4,4',8-trimethylpsoralen (190 mg, 0.68 mmol) in 30 mL of acetonitrile was added to a solution of 1,4-diaminobutane (120 mg, 1.4 mmol) in 7 mL of acetonitrile. After stirring at room temperature overnight, the solvent was removed under reduced pressure. Chloroform (10 mL) and 1N NaOH (10 mL) were added to the residue and the mixture was shaken and separated. The aqueous layer was extracted with a further 2×10 mL of $CHCl_3$ and the combined extracts were rinsed with water. The product was then extracted from the $CHCl_3$ solution with 0.3N aqueous HCl and the acidic layer was then taken to approximately pH 12 with concentrated NaOH solution. The base suspension was extracted with $CHCl_3$ which was then rinsed with water, dried over $Na_2SO_4$ and concentrated under reduced pressure.

The residue was purified by column chromatography on silica gel with $CHCl_3$: EtOH: $Et_3N$ (9:1:0.25). The fractions containing the product were combined and stripped of the solvent to give the free mine. NMR (CDCl$_3$): d 1.35 (m, 3H); 1.49 (m, 4H); 2.22 (s, 3H); 2.46 (d, J=1.1 Hz, 3H); 2.51 (S, 3H); 2.65 (m, 4H); 3.88 (s, 2H); 6.17 (apparent d, 1Hz); 7.40 (s, 1H).

The free base, dissolved in absolute EtOH (~6 mL) was treated with a solution of HCl in ether (1.0M, ~3 mL). The resultant HCl salt was filtered, rinsed with absolute EtOH and dried under vacuum to yield 100 mg (36.3%) of product, m.p. 288° C. (decomposed).

Similarly prepared was 5'-(4-amino-2-aza)butyl-4,4',8-trimethylpsoralen dihydrochloride (Compound 16). NMR of free base: d 1.83 (br s, 3H), 2.27 (s, 3H), 2.51 (s, 3H), 2.58 (s, 3H), 2.74 (m, 2H), 2.87 (m, 2H), 3.95 (s, 2H), 6.24 (s, 1H), 7.46 (s, 1H).

EXAMPLE 8

4'-(14-Amino-2,6,11-Triaza)Tetradecyl-4,5',8-Trimethylpsoralen Tetrahydrochloride (Compound 15)

The synthesis of 4'-(14-amino-2,6,11-triaza)tetradecyl-4,5',8-trimethylpsoralen tetrahydrochloride proceeds in one (1) step, as follows. To a solution of 0.5 g (2.5 mmol) of spermine (Aldrich, Milwaukee, Wis.) in 10 ml of methanol was added a 5N methanolic solution of HCl (concentrated HCl diluted with MeOH to 5N) to adjust to pH 5–6, followed by 0.128 g (0.5 mmol) of 4,5',8-trimethylpsoralen-4'carboxaldehyde, 20 mg (0.3 mmol) of NaBH$_3$CN and 3 mL of MeOH. The reaction mixture was stirred at room temperature overnight. A solution of 5N methanolic HCl was added until pH<2 and methanol was removed under reduced pressure. The residue was taken up in about 100 mL of water and rinsed with three 25 mL portions of CHCl$_3$. The aqueous solution was brought to pH>10 with concentrated NaOH and extracted with three 25 mL portions of CHCl$_3$. These final extracts were combined and washed with water, dried (Na$_2$SO$_4$) and evaporated to give the free base of the amine, ≧95% pure by NMR. NMR (CDCl$_3$): d 1.31 (m, 5H), 1.45 (pent, J=3.41 Hz, 4H), 1.65 (m, 4H), 2.46 (s, 3H), 2.49 (d, J=1.14 Hz, 3H), 2.66 (m, 15H), 3.85 (s, 2H), 6.21 (s, 1H)m 7.60 (s, 1H).

The free amine was dissolved in absolute ethanol and HCl (anhydrous, 1N in ethyl ether) was added. The hydrochloride salt was filtered and washed with absolute ethanol and dried under vacuum at room temperature giving 80.2 mg of product as a light yellow solid.

EXAMPLE 9

The assay used to predict pathogen inactivation efficiency and to determine nucleic acid binding of the photoreactive binding compounds of the present invention was that in which a bacteriophage, R17, in solution with the desired substrate was irradiated. The ability of the phage to subsequently infect bacteria and inhibit their growth was measured. The bacteriophage was selected for its relatively accessible nucleic acid such that the culture growth inhibition would accurately reflect nucleic acid damage by the test compounds. The bacteriophage assay for nucleic acid binding to test compounds offers a safe and inexpensive procedure to identify compounds likely to display efficient pathogen inactivation. The phages have also been shown to accurately reflect HIV-1 sensitivity to similar compounds.

The R17 was grown up in Hfr 3000 bacteria, approximate titer 5×10$^{11}$. (R17 and Hfr 3000 were obtained from American Tissue Culture Collection (ATCC), Washington, D.C.) The R17 phage stock was added to a solution of 15% fetal bovine serum in DMEM to a final phage concentration of 10$^9$/mL. An aliquot (0.5 mL) was transferred to a 1.5 mL snap-top polyethylene tube. An aliquot (0.004–0.040 mL) of the test compound stock solution prepared in water, ethanol or dimethylsulfoxide at 0.80–8.0 mM was added to the tube. Compounds were tested at concentrations between 4 µM and 320 µM. (AMT is commercially available from HRI, Inc., Concord, Calif.; 8-MOP is commercially available from Sigma, St. Louis, Mo.). The tubes were placed in a light device as described in EXAMPLE 1 and irradiated for between 1 and 10 minutes. Sterile 13 mL dilution tubes were prepared; each test compound required one tube with 0.4 mL of LB broth and five tubes containing 0.5 mL of LB broth. To make the dilutions, a 0.100 mL aliquot of the irradiated solution of phage and test compound was added to the first dilution tube of 0.4 mL of media then 0.020 mL of this solution was added to the second tube of 0.5 mL medium (1:25). The second solution was then diluted serially (1:25) into the remaining tubes. To each diluted sample was added 0.050 mL of Hfr 3000 bacteria cultured overnight and 3 mL of molten LB top agar and the mixed materials were poured onto LB broth plates. After the top agar hardened, the plates were incubated at 37° C. overnight. The plaque forming units were then counted the following morning and the titer of the phage remaining after phototreatment was calculated based on the dilution factors.

The following controls were run: the "phage only" in which phage was not treated with test compound and not irradiated (listed as "starting titer" in the tables below); the "UV only" in which the phage was irradiated in the absence of test compound; and the "dark" control in which the phage/test compound solution was not irradiated before it was diluted and plated.

TABLE 3, below, shows three different experiments which tested Compound 1 according to the R17 protocol just described. A comparison of values for the control samples in runs 1–3 (values in bold) shows that neither the "UV only" nor the "dark" controls result in significant bacterial kill (at most, 0.3 logs killed in the "UV only" control and 0.1 logs killed in the "dark" control).

The "UV only" control was repeated in many similar experiments with other compounds of the present invention and consistently showed no significant kill. (Data not shown). Thus, the "UV only" control is not shown in the tables and figures that follow, although it was performed in every experiment in this example. As for the "dark" control, after many trials with various compounds of the present invention, it became apparent that regardless of the type of substitution on the 4' position of the psoralen, no experimentally significant bacterial inactivation was observed in the dark. (Data not shown). For example, in Table 3, experiment 1 shows 0.1 logs kill with compound 1 in the dark. In contrast, when Compound 1 is irradiated for just 1 minute, the resulting drop in titer is >6.7 logs. Therefor, "dark" controls were not run for the later tested compounds and where run, are not shown in the tables and figures that follow.

Figure 6:
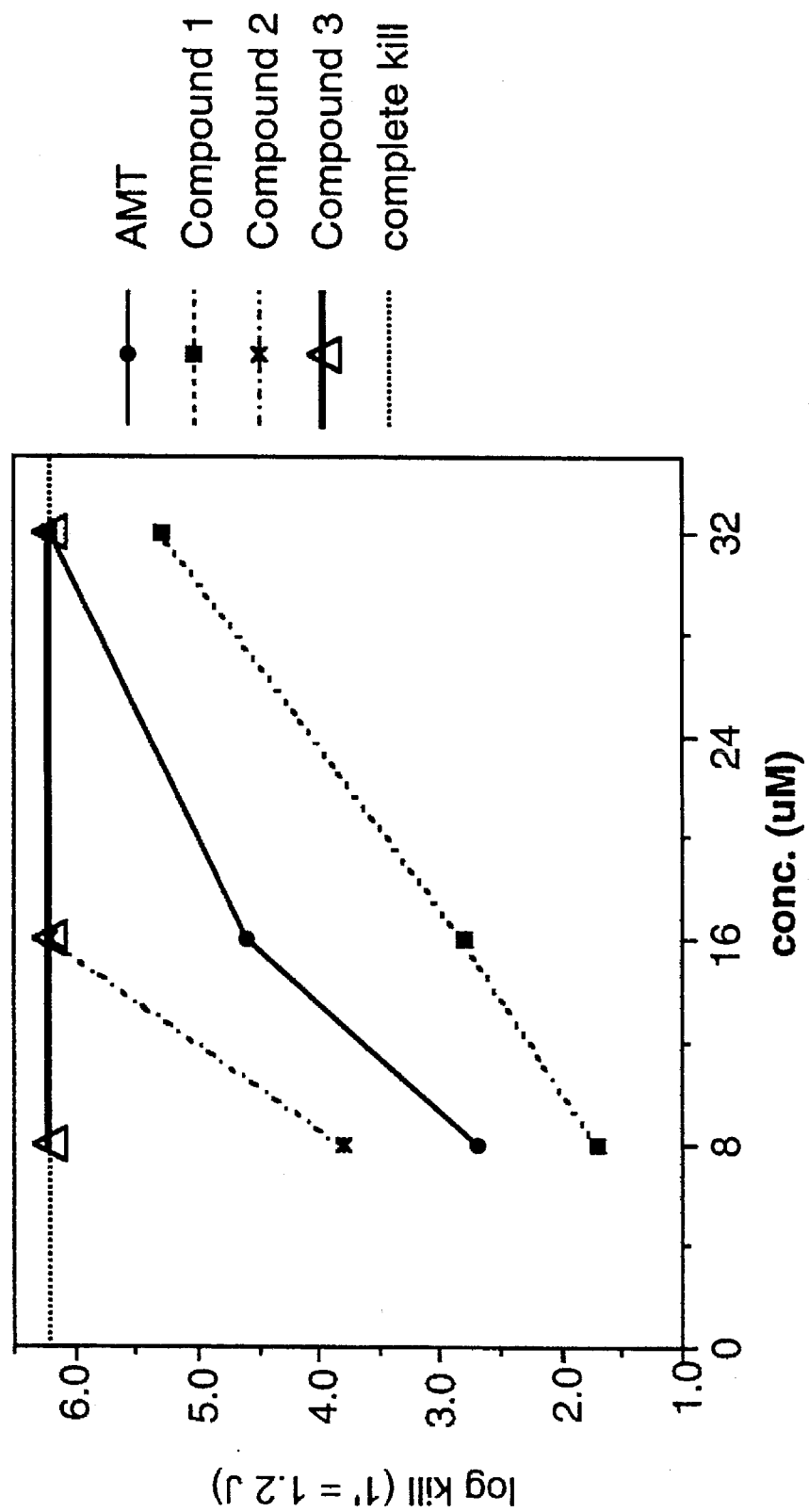
FIG. 6 shows the impact of concentration on the log kill of R17 when Compounds 1–3 of the present invention are photoactivated.
Figure 7:
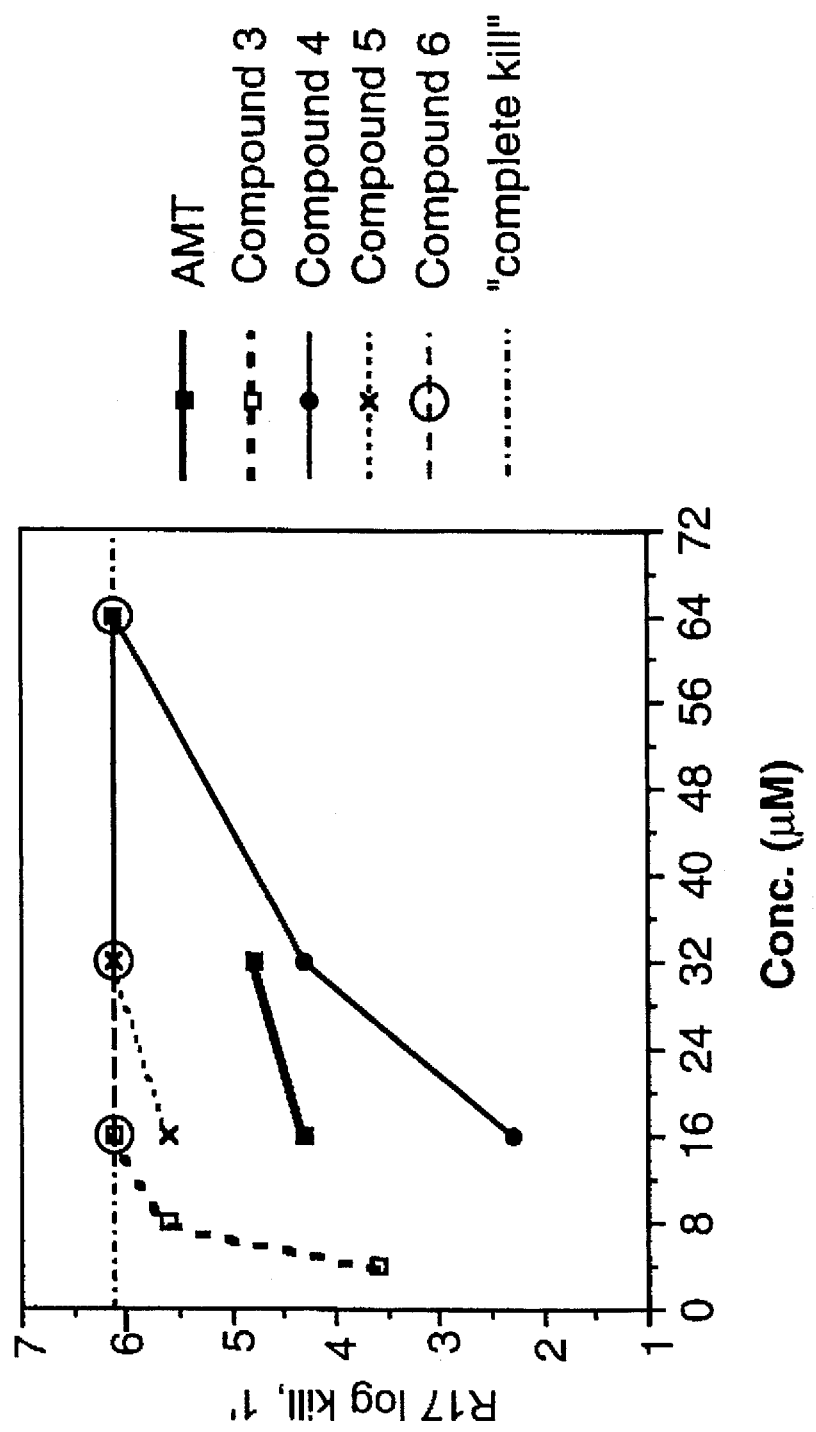
FIG. 7 shows the impact of concentration on the log kill of R17 when Compounds 3–6 of the present invention are photoactivated.
Figure 8:
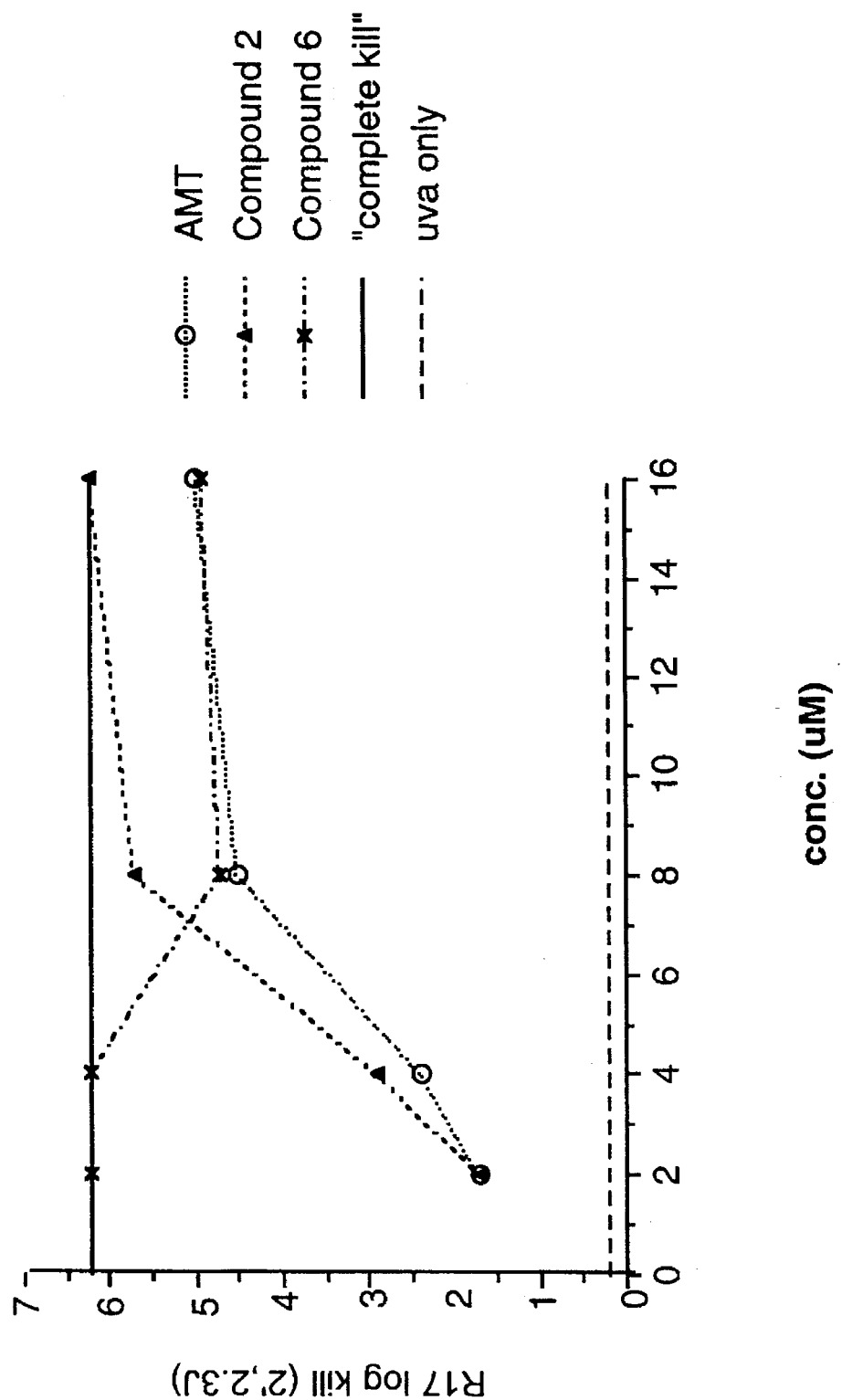
FIG. 8 shows the impact of concentration on the log kill of R17 when Compounds 2 and 6 of the present invention are photoactivated.
Figure 9:
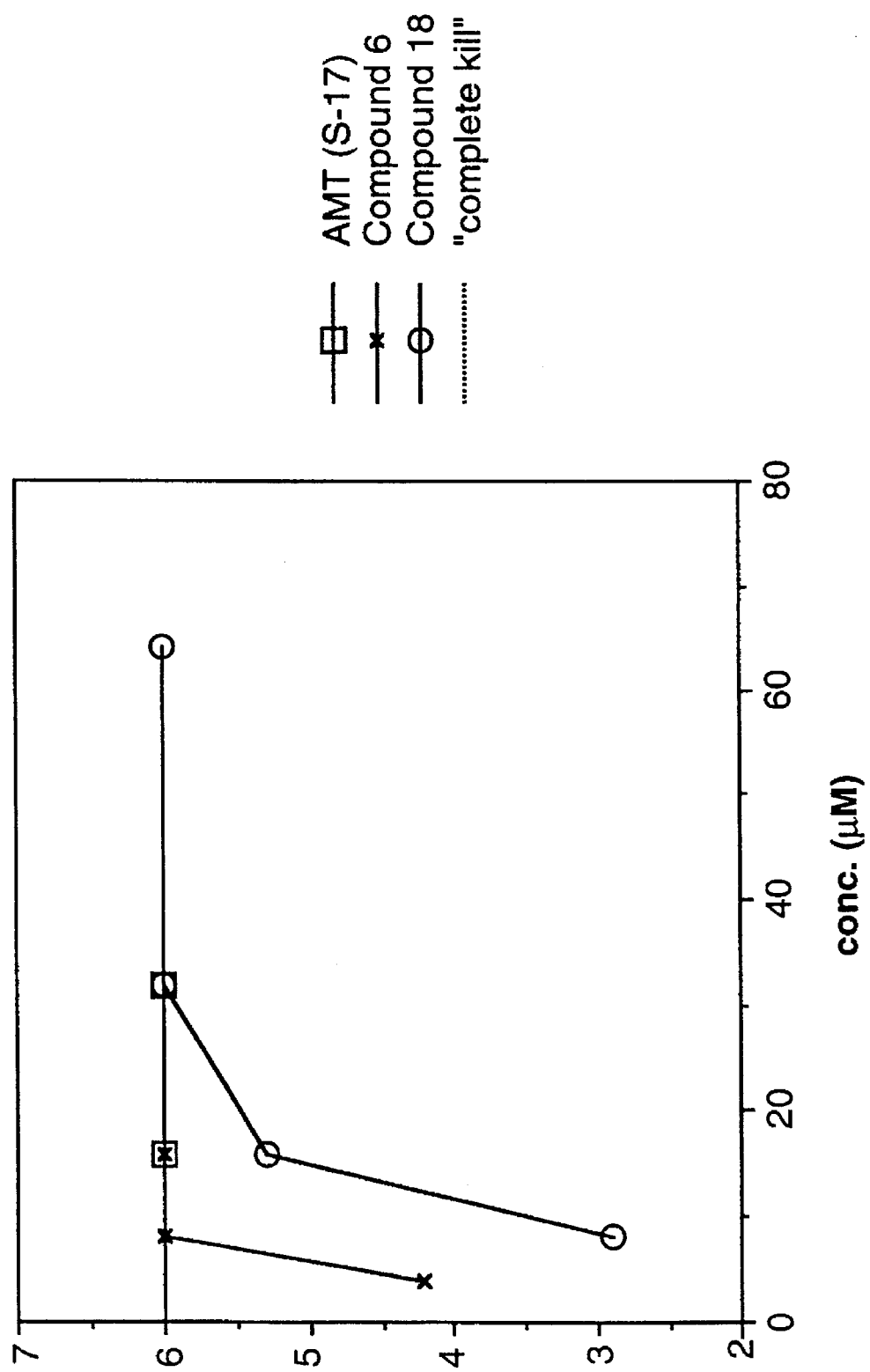
FIG. 9 shows the impact of concentration on the log kill of R17 when Compounds 6 and 18 of the present invention are photoactivated.
Figure 10:
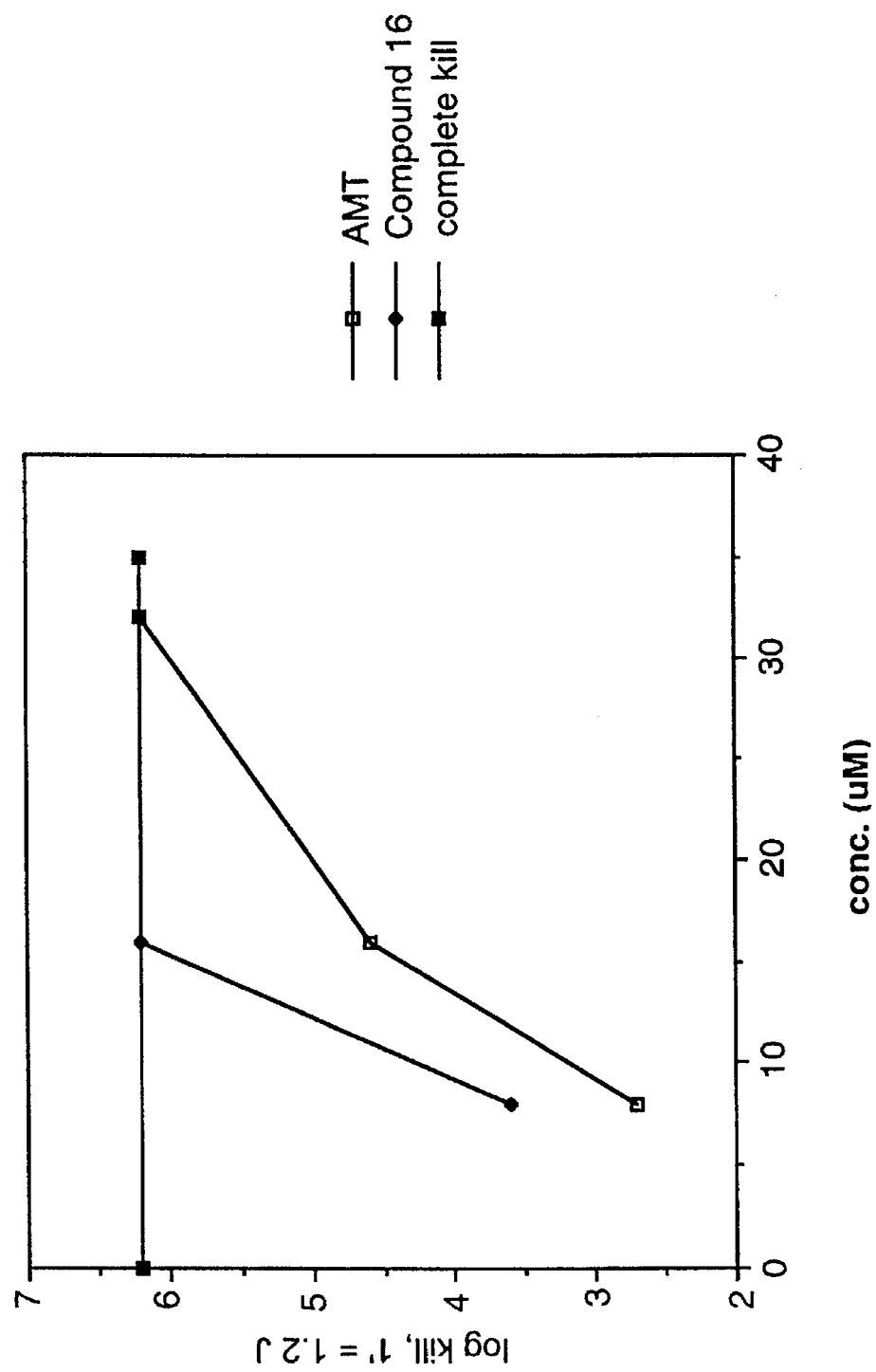
FIG. 10 shows the impact of concentration on the log kill of R17 when Compound 16 of the present invention is photoactivated.
Figure 11:
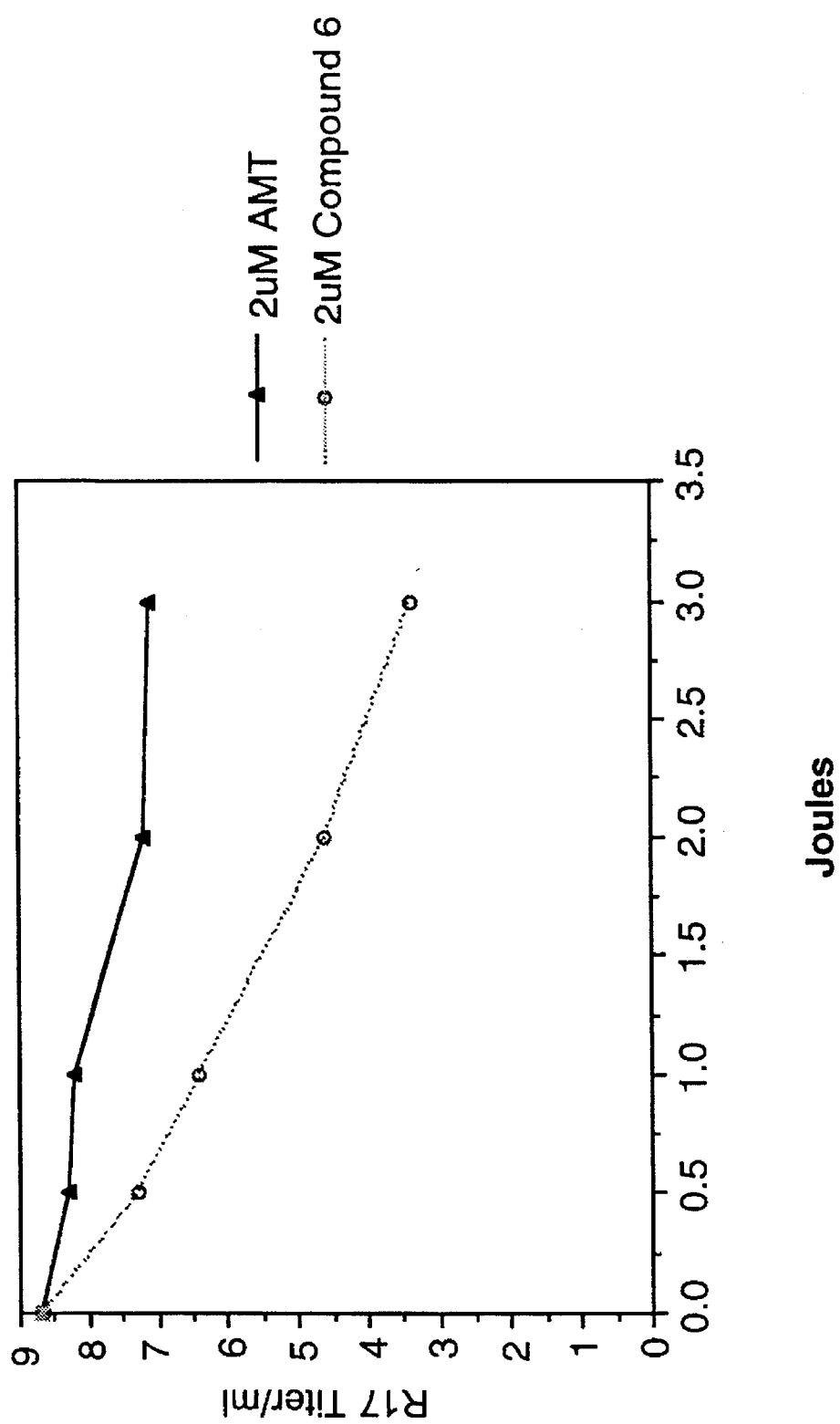
FIG. 11 shows the impact of varying Joules of irradiation on the log titer of R17 for Compound 6 of the present invention.
Figure 12:
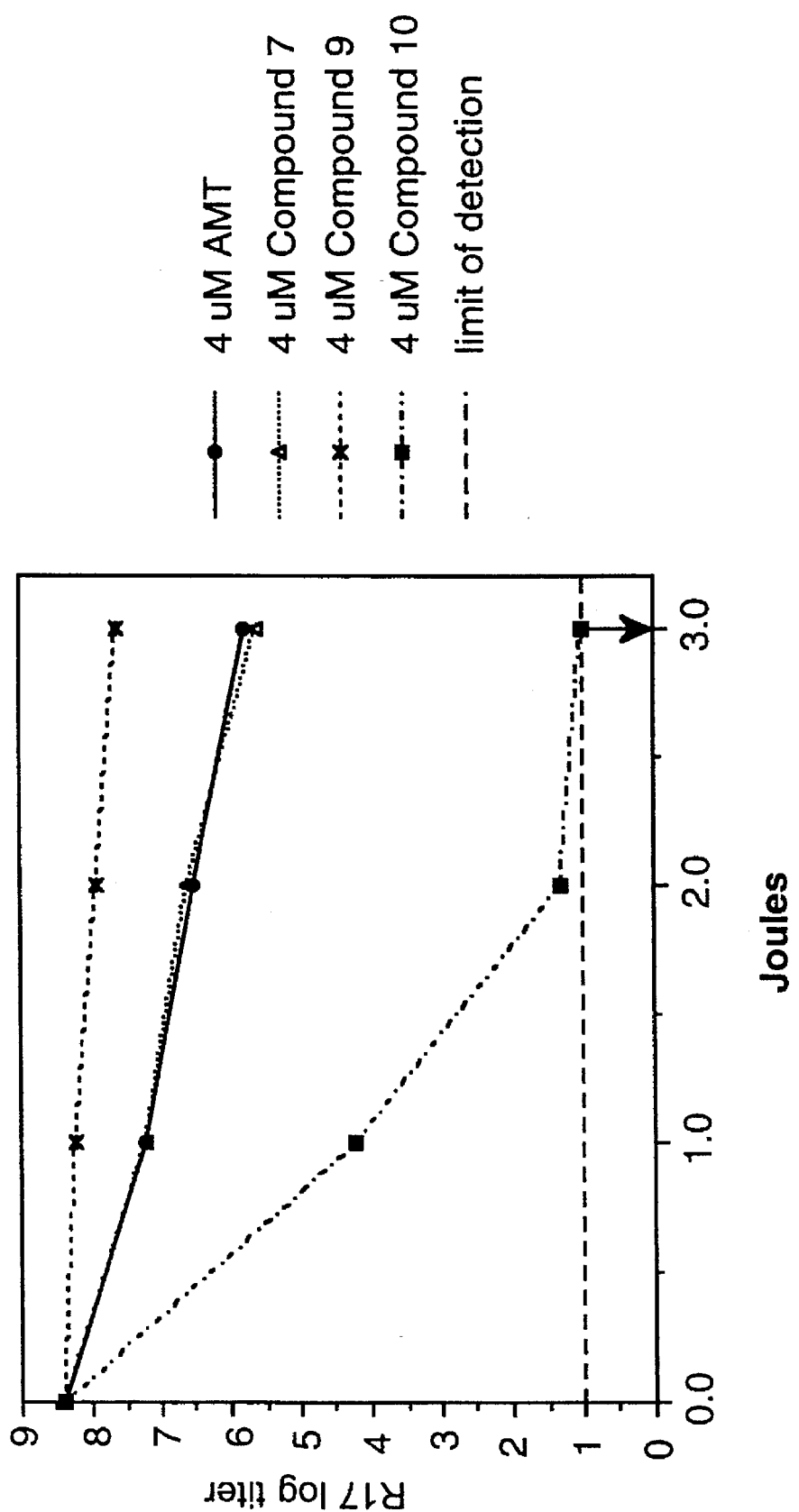
FIG. 12 shows the impact of varying Joules of irradiation on the log titer of R17 for Compounds 7, 9 and 10 of the present invention.
Figure 13:
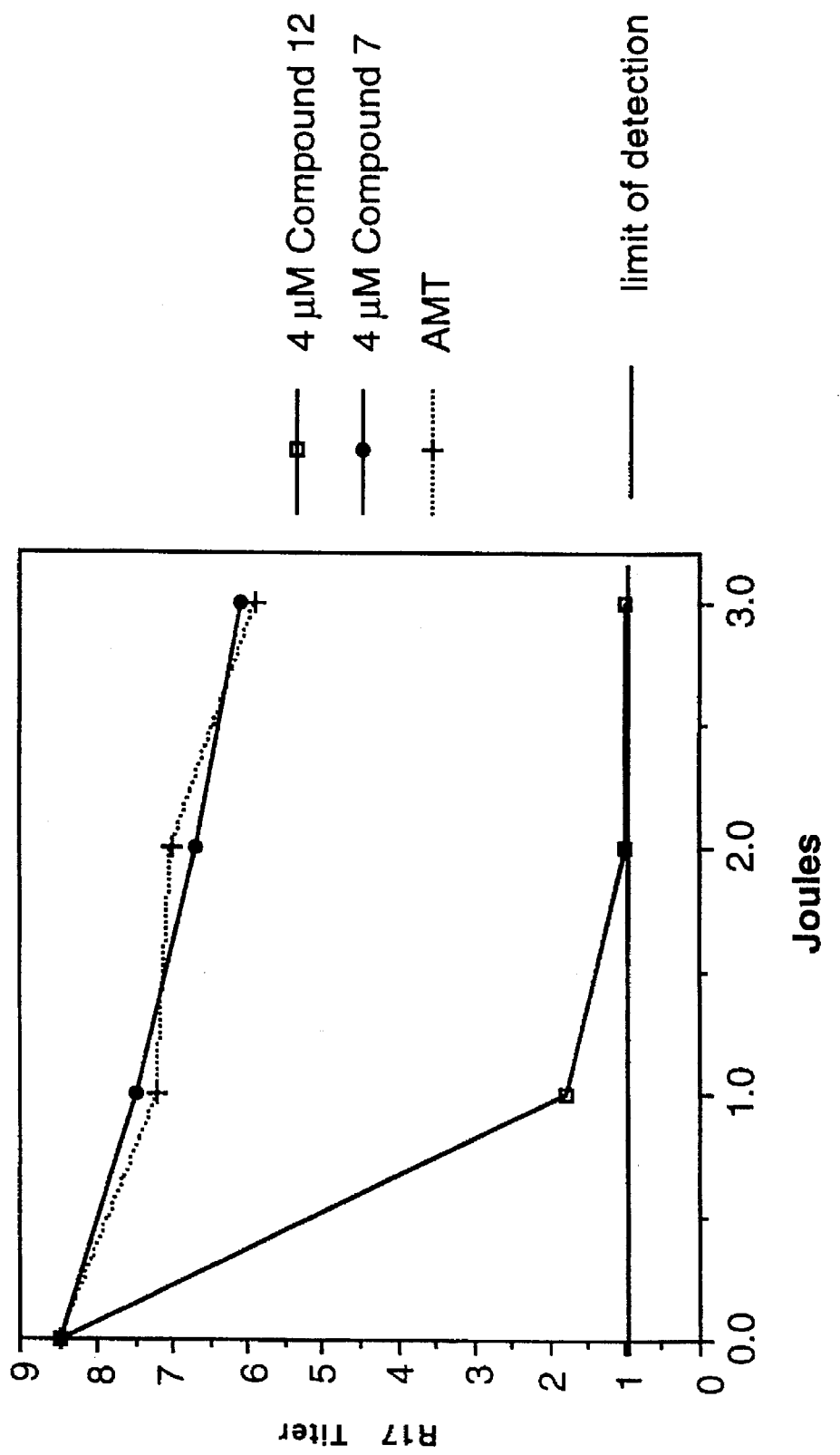
FIG. 13 shows the impact of varying Joules of irradiation on the log titer of R17 for Compounds 7 and 12 of the present invention.
Figure 14:
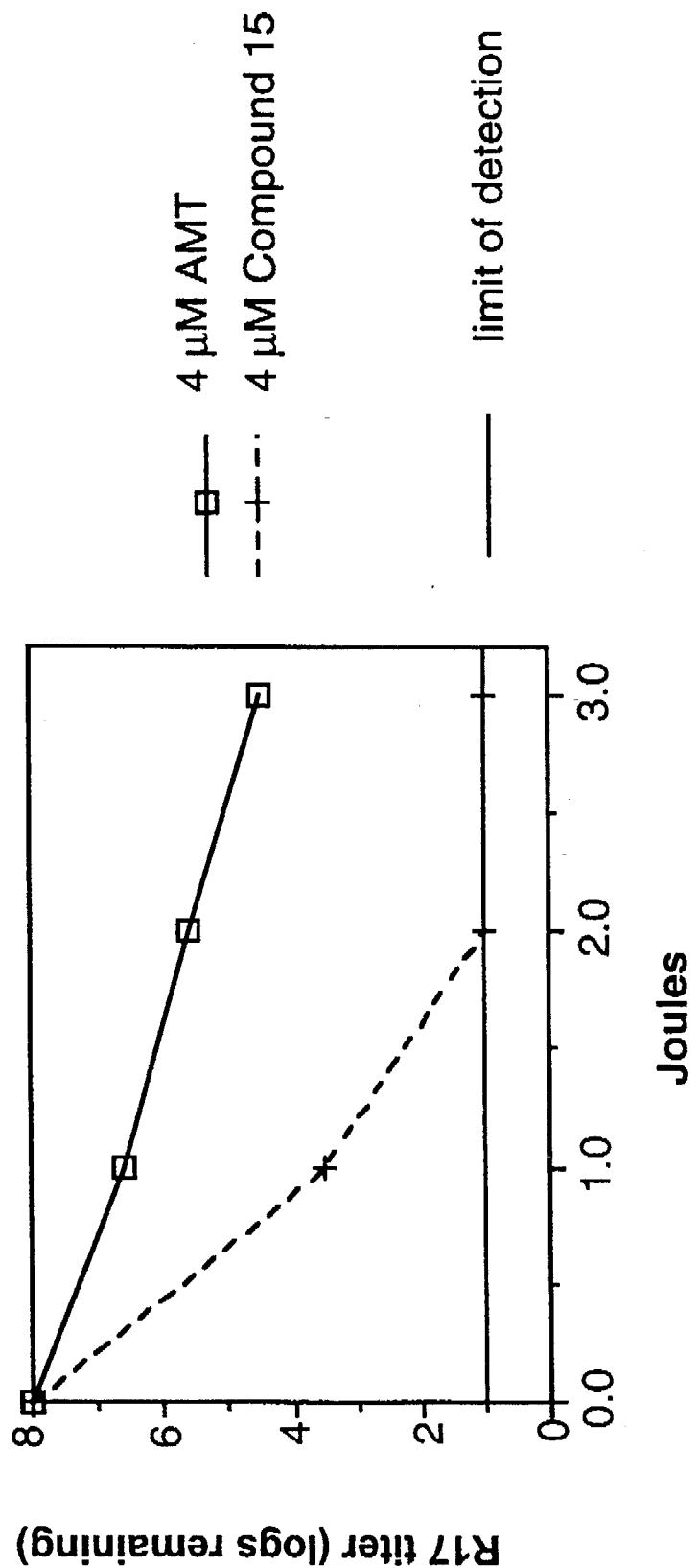
FIG. 14 shows the impact of varying Joules of irradiation on the log titer of R17 for Compound 15 of the present invention.
Figure 15:
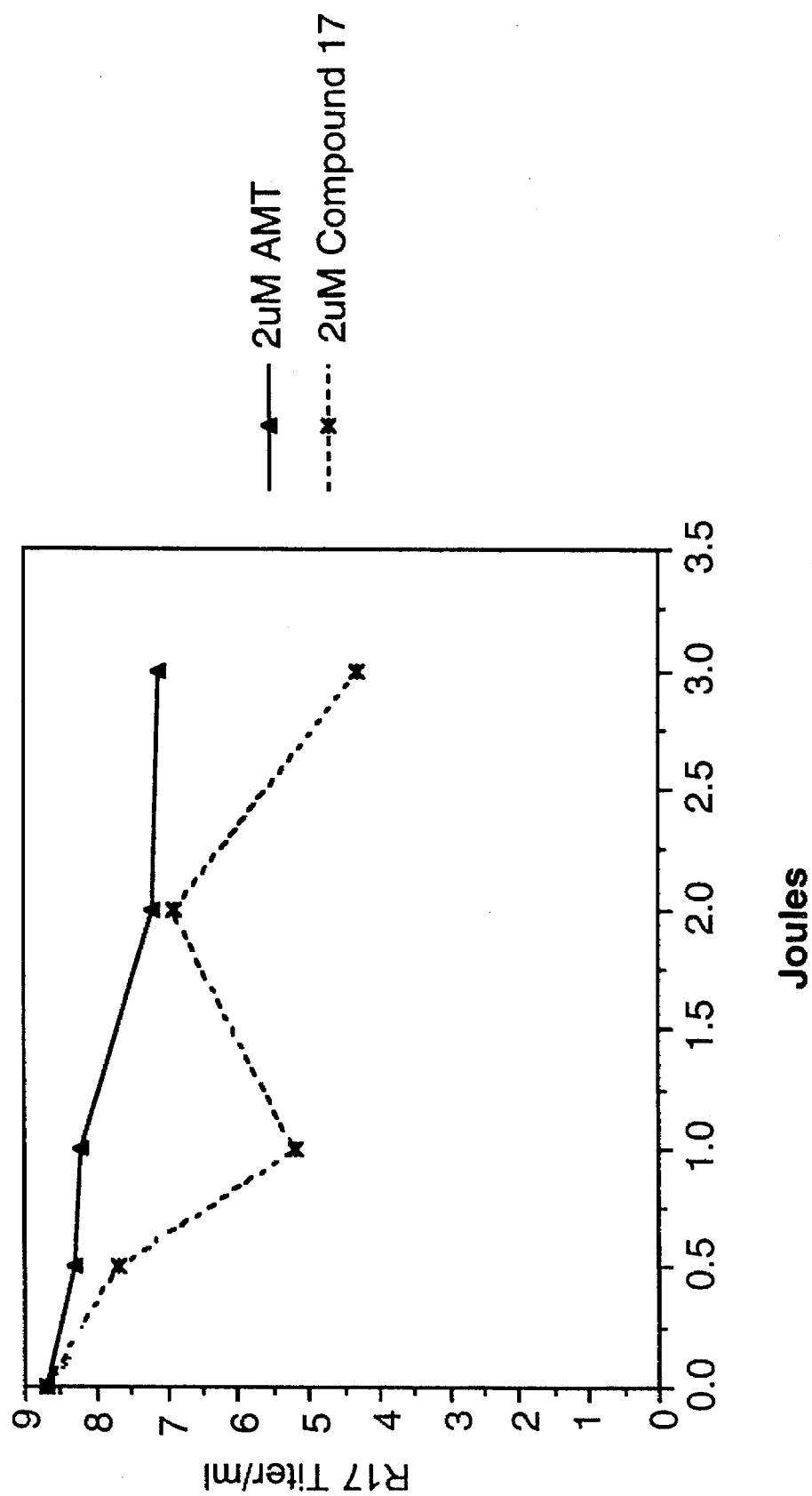
FIG. 15 shows the impact of varying Joules of irradiation on the log titer of R17 for Compound 17 of the present invention.
Figure 16:
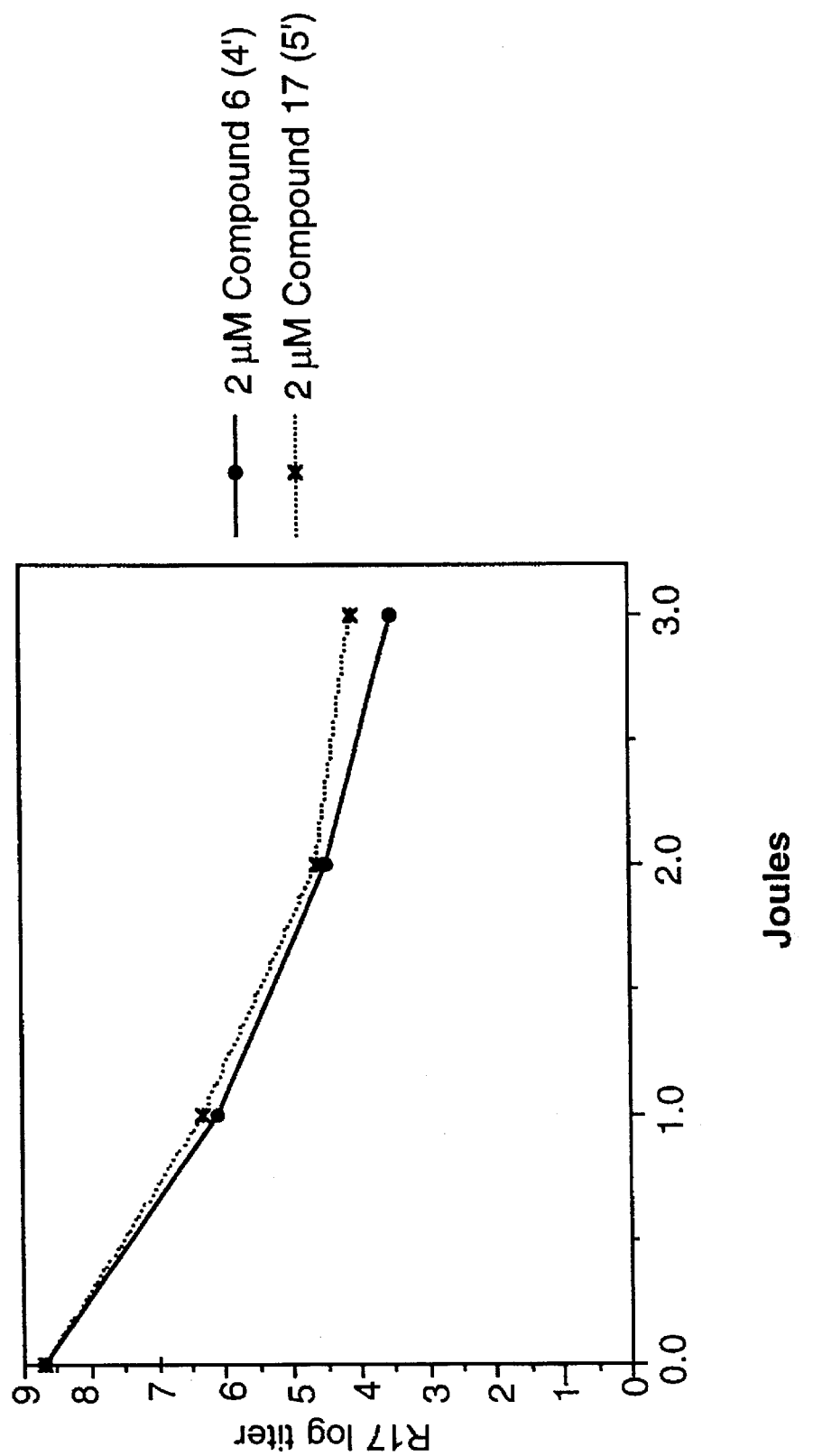
FIG. 16 shows the impact of varying Joules of irradiation on the log titer of R17 for Compounds 6 and 17 of the present invention.
Figure 17:
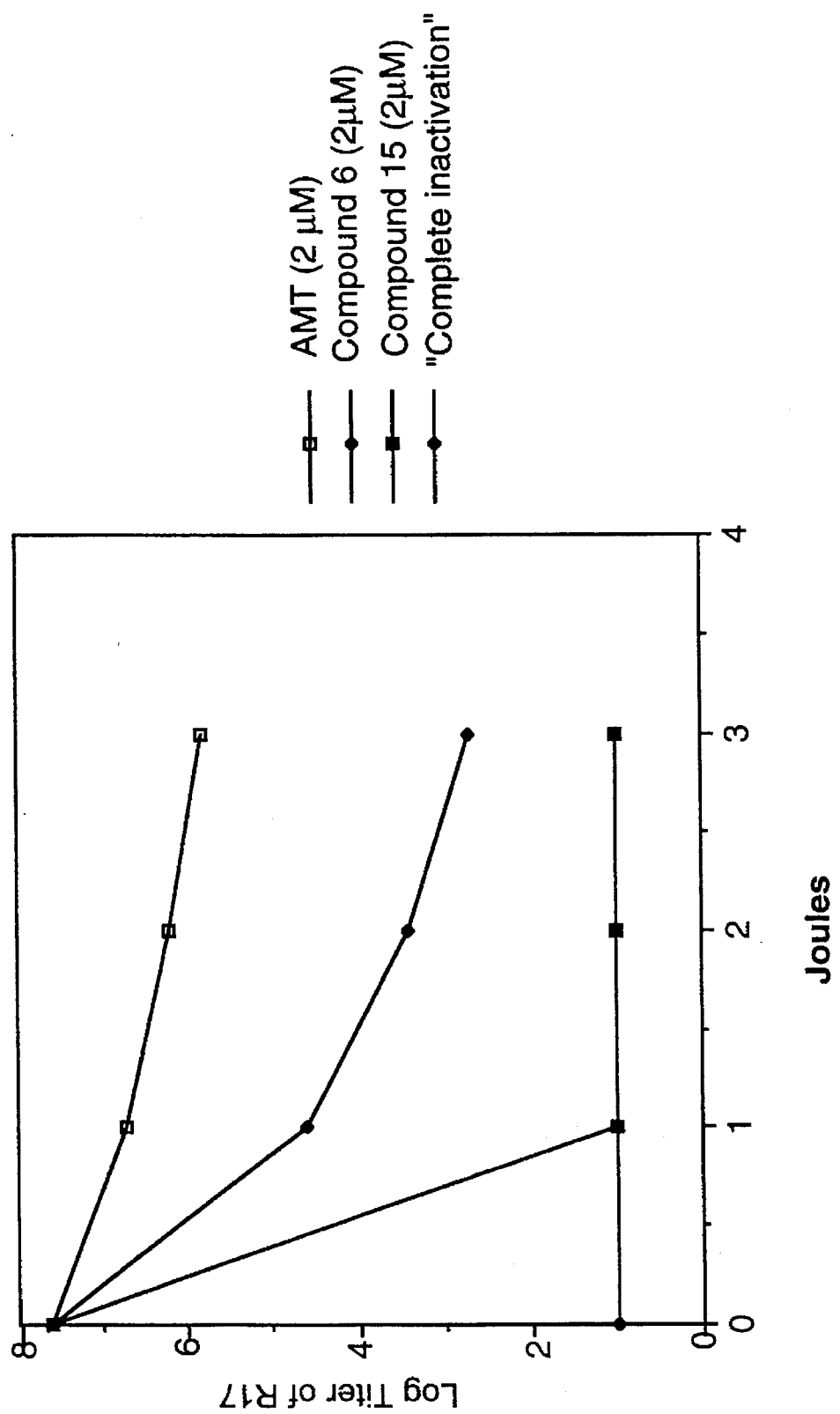
FIG. 17 shows the impact of varying Joules of irradiation on the log titer of R17 for Compounds 6 and 15 of the present invention.

Tables 4–7, below, and FIGS. 6–8 show the results of the R17 assay for several of the 4'-primaryamino-substituted psoralen compounds of the present invention. The data in Tables 5 and 6 appears in FIGS. 6 and 7, respectively. 5'-Primaryamino-substituted psoralen compounds of the present invention, which have substitutions on the 5' position similar to the 4'-primaryamino-substituted psoralen compounds, were also tested at varying concentration, as described above in this example, and are shown to exhibit comparable inactivation efficiency. The results for these compounds are shown in FIGS. 9 and 10, below.

TABLE 3

| EXPERIMENT # | TREATMENT | LOG TITER | LOGS KILLED |
| --- | --- | --- | --- |
| 1 | phage only | 7.7 | — |
|  | uva only (10') | 7.4 | 0.3 |
|  | compound only (32 µM) | 7.6 | 0.1 |
|  | 32 µM cmpd 1' uva | <1 | >6.7 |
|  | 32 µM cmpd 10' uva | <1 | >6.7 |
| 2 | phage only | 7.8 | — |
|  | uva only (10') | 7.6 | 0.2 |
|  | compound only (3.2 µM) | 7.7 | 0.1 |
|  | 3.2 µM cmpd 1' uva | 6.9 | 0.9 |
|  | 3.2 µM cmpd 10' uva | 6.1 | 1.7 |
| 3 | phage only | 7.3 | — |
|  | uva only (1') | 7.3 | 0 |
|  | compound only | 7.3 | 0 |

TABLE 3-continued

| EXPERIMENT # | TREATMENT | LOG TITER | LOGS KILLED |
|---|---|---|---|
| | (16 μM) | | |
| | 4 μM cmpd 1' uva | 6.3 | 1.0 |
| | 8 μM cmpd 1' uva | 5.6 | 1.7 |
| | 16 μM cmpd 1' uva | 3.9 | 3.4 |

TABLE 4

Starting Titer of R17: Approx. 7.5 Logs
1 Minute Irradiation

| Cmpd. | Structure | R17 log kill (32 μM) |
|---|---|---|
| AMT | [structure: furocoumarin with CH2NH2] | >6.7 |
| 8-MOP | [structure: 8-methoxypsoralen] | 0 |

TABLE 4-continued

Starting Titer of R17: Approx. 7.5 Logs
1 Minute Irradiation

| Cmpd. | Structure | R17 log kill (32 μM) |
|---|---|---|
| 1 | [structure: furocoumarin with CH2NHCH2CH2NH2] | >6.6 |

TABLE 5

Starting Titer Approx.: 7.2 logs R17
1 Minute Irradiation

| Compound | Structure | R17 8 uM | Log 16 uM | Kill 32 uM |
|---|---|---|---|---|
| AMT | [structure with CH2NH2] | 2.7 | 4.6 | >6.2 |
| 1 | [structure with NHCH2CH2NH2] | 1.7 | 2.8 | 5.3 |
| 2 | [structure with OCH2CH2NH2] | 3.8 | >6.2 | >6.2 |

TABLE 5-continued

Starting Titer Approx.: 7.2 logs R17
1 Minute Irradiation

| Compound | Structure | R17 8 uM | Log 16 uM | Kill 32 uM |
|---|---|---|---|---|
| 3 | (structure with NH₂ group) | >6.2 | >6.2 | >6.2 |

TABLE 6

Starting Titer Approx.: 7.1 Logs
1 Minute Irradiation = 1.2 J/cm²

| Cmpd. | Structure | R17 8 uM | log 16 uM | kill 32 uM | 64 uM |
|---|---|---|---|---|---|
| AMT | (structure with CH₂NH₂) | — | 4.5 | 4.8 | — |
| 3 | (structure with CH₂CH₂NH₂) | 5.6 | >6.1 | — | — |
| 4 | (structure with OCH₂CH₂CH₂NH₂) | — | 2.3 | 4.3 | >6.1 |
| 5 | (structure with CH₂NHCH₂CH₂CH₂NH₂) | — | 5.6 | >6.1 | >6.1 |

TABLE 6-continued

Starting Titer Approx.: 7.1 Logs
1 Minute Irradiation = 1.2 J/cm$^2$

| Cmpd. | Structure | R17 8 uM | log 16 uM | kill 32 uM | 64 uM |
|---|---|---|---|---|---|
| 6 | (structure: NH-CH$_2$-CH$_2$-CH$_2$-CH$_2$-NH$_2$ substituted psoralen) | — | >6.1 | >6.1 | >6.1 |

TABLE 7

Starting Titer Approx.: 7.1 logs R17
1 Minute Irradiation

| Cmpd. | Structure | R17 8 uM | log 16 uM | kill 32 uM | 64 uM |
|---|---|---|---|---|---|
| AMT | (structure: CH$_2$NH$_2$ substituted psoralen) | — | >6 | >6 | — |
| 6 | (structure: NH-CH$_2$-CH$_2$-CH$_2$-CH$_2$-NH$_2$ substituted psoralen) | >6 | >6 | — | — |
| 7 | (structure: O-CH$_2$-CH$_2$-O-CH$_2$-CH$_2$-NH$_2$ substituted psoralen) | — | >6 | >6 | >6 |

The compounds of the present invention having substitutions on the 4' position of the psoralen ring proved to be active in killing R17, as shown in the tables above. In Table 4, it is apparent that compound 1 of the present invention exhibits much higher R17 inactivation efficiency than does 8-MOP. As shown in Table 5 and FIG. 6, Compound 1 is one of the less active compounds of the present invention. Both Compounds 2 and 3 show higher log inactivation than Compound 1 at each concentration point. These results support that the compounds of the present invention are generally much more active than 8-MOP.

The compounds of the present invention also have similar or better R17 inactivation efficiency than AMT. In Tables 5 and 6, and FIGS. 6–10, all compounds of the present invention achieve R17 log inactivation at levels comparable to AMT. Compounds 2 and 3 (Table 5, FIG. 6), Compounds 5 and 6 (Table 6, FIG. 7), and Compound 16 (FIG. 10) exhibit significantly higher inactivation efficiency than does AMT.

Compounds of the present invention were also tested at a constant concentration for varying doses of UV light. Three sets of 1.5 mL tubes were prepared containing 0.6 mL aliquots of R17 in DMEM (prepared as described above). The compound tested was added at the desired concentration and the samples were vortexed. The samples were then irradiated at intervals of 1.0 J/cm$^2$, until 3.0 J/cm$^2$ was reached. Between each 1.0 J/cm$^2$ interval, 100 μL was removed from each sample and placed in the first corresponding dilution tube, then five sequential dilutions were performed for each compound tested, at all 3 irradiation doses, as described above in this example.

Then 50 μL of Hfr 3000 bacteria was added to each tube, 3 mL of top agar was added and the tube contents were vortexed. The contents of each tube was poured into its own LB plate and the plates were incubated overnight at 37° C. Plaques were counted by visual inspection the following morning.

The results of the assay for several 4' and 5'-primaryamino-substituted psoralen compounds are shown in FIGS. 11–17. This data further supports that the compounds of the present invention are comparable to AMT in their ability to inactivate R17. Further, Compounds 6 (FIG. 11), 10 (FIG. 12), 12 (FIG. 13), 15 (FIG. 14 and 17), and Compound 17 (FIG. 15), all were more efficient at inactivating R17 than was AMT.

EXAMPLE 10

Pathogen inactivation efficiency of several compounds of the present invention was evaluated by examining the ability of the compounds to inactivate cell-free virus (HIV). Inactivation of cell-free HIV was performed as follows.

As in the R17 assay, small aliquots of the compounds listed in TABLES 8 and 9, below, at the concentrations listed in the table, were added to stock HIV-1 to a total of 0.5 mL. The stock HIV ($10^5$–$10^7$ plaque forming units/mL) was in DMEM/15% FBS. The 0.5 mL test aliquots were placed in 24 well polystyrene tissue culture plates and irradiated with 320–400 nm (20 mW/cm$^2$) for 1 min on a device similar to the device of Example 1. The photoactivation device used here was previously tested and found to result in light exposure comparable to the Device of Example 1. (Data not shown). Controls included HIV-1 stock only, HIV-1 plus UVA only, and HIV-1 plus the highest concentration of each psoralen tested, with no UVA. Post irradiation, all samples were stores frozen at –70° C. until assayed for infectivity by a microtiter plaque assay. Aliquots for measurement of residual HIV infectivity in the samples treated with a compound of the present invention were withdrawn and cultured.

Residual HIV infectivity was assayed using an MT-2 infectivity assay. (Previously described in Hanson, C. V., Crawford-Miksza, L. and Sheppard, H. W., J. Clin. Micro 28:2030 (1990)). The assay medium was 85% DMEM (with a high glucose concentration) containing 100 μg of streptomycin, 100 U of penicillin, 50 μg of gentamicin, and 1 μg of amphotericin B per mL, 15% FBS and 2 μg of Polybrene (Sigma Chemical Co., St. Louis, Mo.) per mL. Test and control samples from the inactivation procedure were diluted in 50% assay medium and 50% normal human pooled plasma. The samples were serially diluted directly in 96-well plates (Corning Glass Works, Corning, N.Y.). The plates were mixed on an oscillatory shaker for 30 seconds and incubated at 37° C. in a 5% $CO_2$ atmosphere for 1 to 18 hours. MT-2 cells (0.025 mL) [clone alpha-4, available (catalog number 237) from the National Institutes of Health AIDS Research and Reference Reagent Program, Rockville, Md.] were added to each well to give a concentration of 80,000 cells per well. After an additional 1 hour of incubation at 37° C. in 5% $CO_2$, 0.075 mL of assay medium containing 1.6% SeaPlaque agarose (FMC Bioproducts, Rockland, Me.) and prewarmed to 38.5° C. was added to each well. The plates were kept at 37° C. for a few minutes until several plates had accumulated and then centrifuged in plate carriers at 600×g for 20 minutes in a centrifuge precooled to 10° C. In the centrifuge, cell monolayers formed prior to gelling of the agarose layer. The plates were incubated for 5 days at 37° C. in 5% $CO_2$ and stained by the addition of 0.05 mL of 50 μg/mL propidium iodide (Sigma Chemical Co.) in phosphate-buffered saline (pH 7.4) to each well. After 24 to 48 hours, the red fluorescence-stained microplaques were visualized by placing the plates on an 8,000 μW/cm$^2$ 304 nm UV light box (Fotodyne, Inc., New Berlin, Wis.). The plaques were counted at a magnification of ×20 to ×25 through a stereomicroscope. The results are shown in TABLES 8 and 9, below. "n" represents the number of runs for which the data point is an average.

The results support that the compounds of the present invention are effective in inactivating HIV. In fact, the data for concentrations of 64 μM of compound or higher suggests that compounds 2 and 3 are significantly more active than AMT, which was previously thought to be one of the most active anti-viral psoralens. At lower concentrations, Compound 6 is able to kill a higher log of HIV (3.1 logs at 32 μM) than is AMT (2.5 logs at 32 μM). The other compounds listed in TABLE 8 display inactivation efficiency in the same range as AMT.

TABLE 8

1 Minute Irradiation
HIV Starting Titer: Approximately 5 Logs

| COMPOUND | HIV Log Kill | | | |
|---|---|---|---|---|
| | 16 μM | 32 μM | 64 μM | 128 μM |
| AMT | 1.4 | 1.9–>3.6 | 3.9–>3.6 | >4.1 |
| 1 | — | — | 2.1 | >2.8 |
| 2 | 1.4 | 3.8 | >4.5 | >4.5 |
| 3 | — | 2.7 | >3.8 | >3.8 |
| 4 | — | 2.2 | >3.6 | >3.6 |
| 5 | 0.9 | 1.3 | >2.6 | — |
| 6 | 2.0 | 3.1 | >3.8 | — |
| 7 | 0.8 | 2.1 | 3.5 | — |
| 8 | 1.1 | 1.9 | 3.7 | >3.7 |

TABLE 9

HIV Starting Titer: Approximately 5.4 Logs
1 Minute Irradiation

| COMPOUND | HIV Log Kill | | |
|---|---|---|---|
| | 16 μM | 32 μM | 64 μM |
| 6 | 2.1 | 3.2 | >2.8 |
| 9 | 0.8 | 1.4 | 2.7 |
| 10 | 2.0 | >3.5 | >3.5 |
| 12 | 0.4 | 0.8 | 1.3 |
| 17 | 1.2 | 2.9 | 3.4 |
| 18 | 1.0 | 1.0 | 3.1 |

EXAMPLE 11

This example describes the protocol for inactivation of another virus, Duck Hepatitis B Virus (DHBV), using compounds of the present invention.

DHBV in duck yolk was added to platelet concentrate (PC) to a final concentration of 2×10$^7$ particles per mL and mixed by gentle rocking for ≧15 min. Psoralens S-70, S-59 and AMT were added to 3 mL aliquots of PC in a Teflon™ mini-bag at concentrations of 35, 70, and 100 mM. Samples, including controls without added psoralen, were irradiated with 5 J/CM$^2$ UVA, with mixing at 1 J/cm$^2$ increments. After irradiation, leukocytes and platelets were separated from virus by centrifugation. The supernatant containing DHBV was digested overnight with 50 μg/mL proteinase K in a buffer containing 0.5% sodium dodecyl sulphate, 20 mM Tris buffer, pH 8.0, and 5 mM EDTA at 55° C. Samples were extracted with phenol-chloroform and chloroform, followed by ethanol precipitation. Purified DNA was then used in PCR amplification reactions with a starting input of $10^6$ DHBV genomes from each sample. PCR amplicons were generated using primers pairs DCD03/DCD05 (127 bp), DCD03/DCD06 (327 bp) and DCD03/DCD07 (1072 bp). PCR was performed in a standard PCR buffer containing 0.2 mM each deoxyribonucleoside 5'-triphosphates (dATP, dGTP, dCTP, and dTTP), 0.5 mM each primer, and 0.5 units Taq polymerase per 100 ml reaction. 30 cycles of amplification were performed with the following thermal profile: 95° C. 30 sec, 60° C. 30 sec, 72° C. 1 min. The amplification was followed by a 7 min incubation at 72° C. to yield full length products. [lambda-$^{32}$P] dCTP was added at an amount of 10 mCi per 100 ml in order to detect and quantify the resulting products. Products were separated by electrophoresis on denaturing polyacrylamide slab gels and counted. The absence of signal in a given reaction was taken to indicate effective inactivation of DHBV.

The results showed that the smaller amplicons displayed increasing inactivation as a function of psoralen concentration for all psoralens tested. At the same concentrations, S-59 and S-70 inhibited PCR of the smaller amplicons better than did AMT. For the 1072 bp amplicon, complete inhibition of PCR was observed at all concentrations of S-59 and S-70, whereas the sample without psoralen gave a strong signal. AMT inhibited PCR amplification of the 1072 bp amplicon at the 70 and 100 mM levels, but a signal could be detected when AMT was used at 35 mM final concentration.

EXAMPLE 12

In Example 10, the compounds of the present invention were tested for their ability to inactivate virus in DMEM/15% FBS. In this example, the compounds are tested in both 100% plasma and predominantly synthetic media, to show that the methods of the present invention are not restricted to any particular type of medium.

For the samples in synthetic media: standard human platelet concentrates were centrifuged to separate plasma. Eighty-five percent of the plasma was then expressed off and replaced with a synthetic medium (referred to as "Sterilyte™ 3.0") containing 20 mM Na acetate, 2 mM glucose, 4 mM KCl, 100 mM NaCl, 10 mM Na$_3$ Citrate, 20 mM NaH$_2$PO$_4$/Na$_2$HPO$_4$, and 2 mM MgCl$_2$. H9 cells infected with HIV were added to either the 85% Sterilyte™ 3.0 platelet concentrates or standard human platelet concentrates (2.5×10$^7$ cells per concentrate), final concentration 5×10$^5$ cells/mL. The platelet concentrates were placed in Teflon™ modified FL20 or Teflon™ Minibags (American Fluoroseal Co., Silver Springs, Md.), treated with one of the compounds shown in FIGS. 18 and 19, at the concentrations shown, and then irradiated with 320–400 nm (20 mW/cm2) for 5 J/cm$^2$ (for plasma samples) or 2 J/cm$^2$ (for 85% Sterilyte™ 3.0 samples) on a device similar to the Device of Example 1. The photoactivation device used here was previously tested and found to result in light exposure comparable to the Device of Example 1. (Data not shown). Aliquots for measurement of residual HIV infectivity in the samples treated with a compound of the present invention were withdrawn and cultured.

Figure 18:
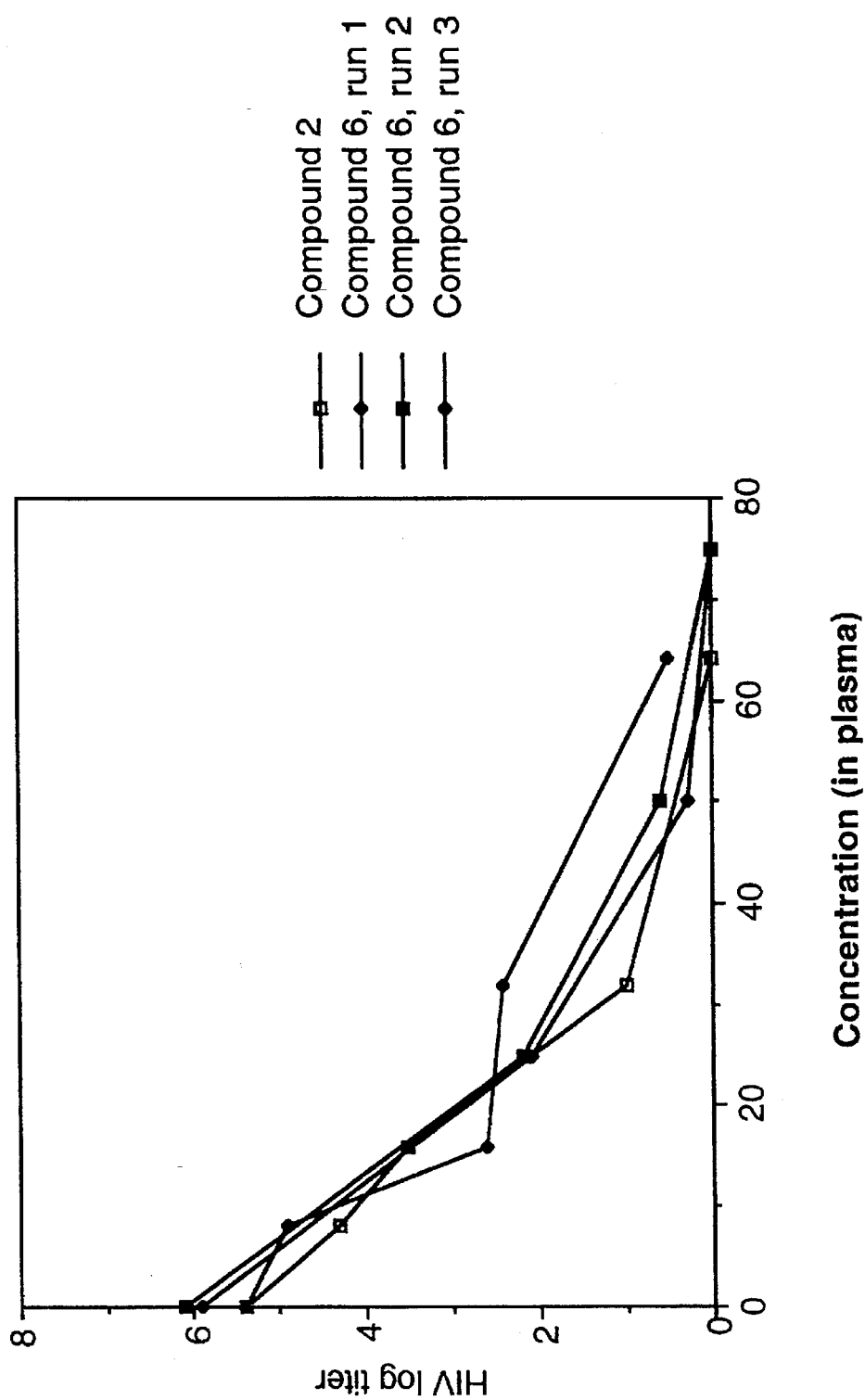
FIG. 18 shows the effect of varying the concentration of Compounds 2 and 6 of the present invention, in plasma.
Figure 19:
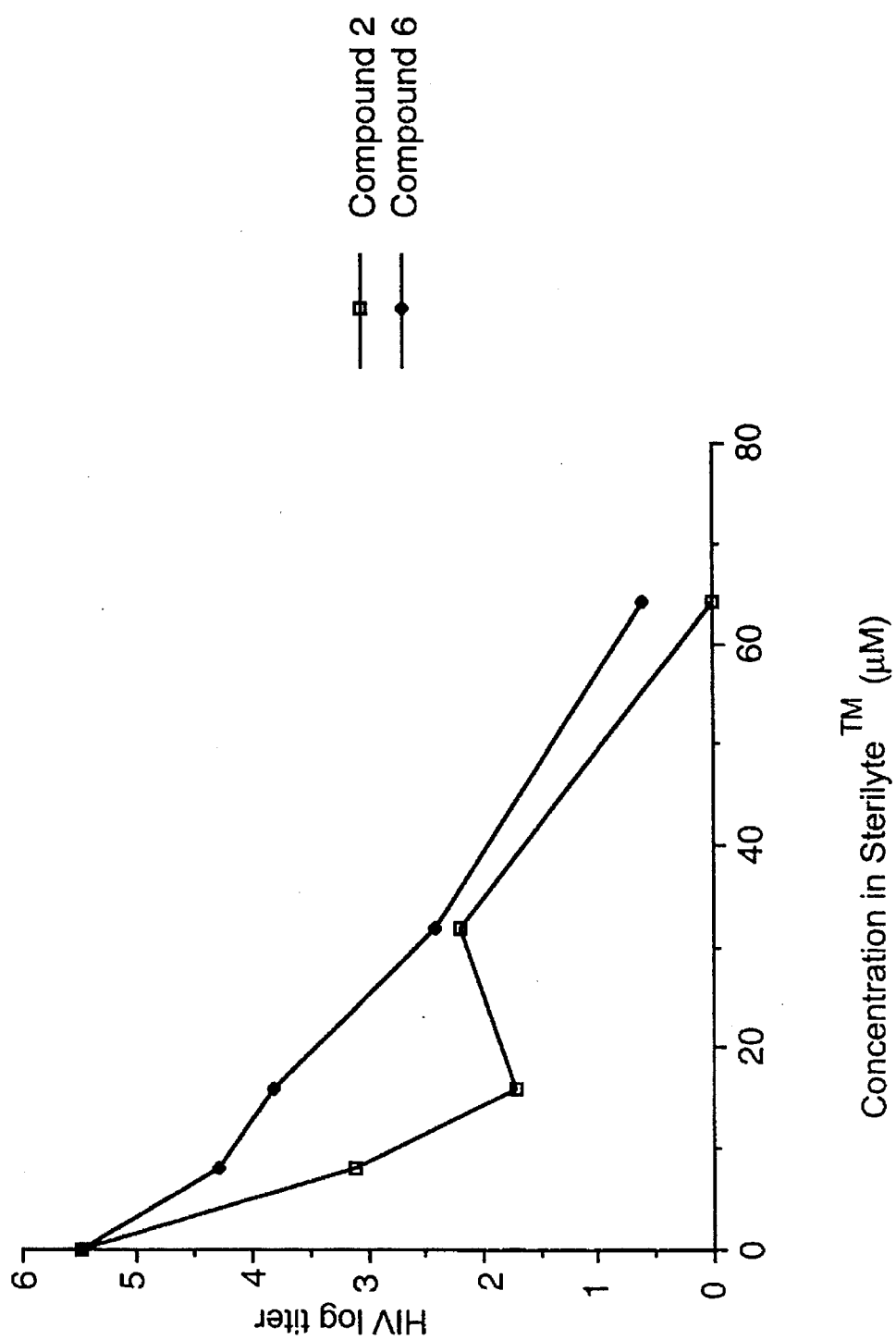
FIG. 19 shows the effect of varying the concentration of Compounds 2 and 6 of the present invention, in synthetic medium.

For samples run in plasma: H9 cells infected with HIV were added to standard human platelet concentrates (2.5×10$^7$ cells per concentrate), final concentration 5×10$^5$ cells/mL. Aliquots of HIV contaminated platelet concentrate (5 mL) were placed in water jacketed Pyrex chambers. The chambers had previously been coated on the inside with silicon. The platelet concentrates were treated with one of the compounds listed in TABLES 8 and 9, below, at the concentrations listed in the table, and then irradiated with 320–400 nm (20 mW/cm2) for 1 minute on a device similar to the Device of Example 1. The photoactivation device used here was previously tested and found to result in light exposure comparable to the Device of Example 1. (Data not shown). Aliquots for measurement of residual HIV infectivity in the samples treated with a compound of the present invention were withdrawn and cultured. Residual HIV infectivity was assayed for both the plasma and the 85% Sterilyte™ samples using an MT-2 infectivity assay. (Detailed in Example 10, above, and previously described in Hanson, C. V., et al., J. Clin. Micro 28:2030 (1990)). The results are shown in FIGS. 18 and 19.

The results support that the compounds of the present invention are effective in inactivating HIV in both plasma and synthetic medium. Comparing FIGS. 18 and 19, the inactivation curves appear to be the same, both achieving approximately 5 logs of inactivation at 64 µM concentrations of compound. However, the inactivation in synthetic media was performed with only 2 J/cm$^2$ irradiation, 3 J/cm$^2$ less than that required to achieve the same inactivation in plasma. Thus, it appears from the data that synthetic media facilitates the inactivation methods of the present invention.

EXAMPLE 13

In this example bacterial inactivation by the photoreactive nucleic acid binding compounds of the present invention was measured as a function of the ability of the bacteria to subsequently replicate. A gram negative bacteria was chosen as representative of the more difficult bacterial strains to inactivate.

The bacteria, a strain of Pseudomonus, was innoculated into LB with a sterile loop and grown overnight in a shaker at 37° C. Based on the approximation that one OD at 610 nm is equivalent to 5×10$^8$ colony forming units (cfu)/mL, a 1:10 dilution of the culture was measured on a spectrophotometer, (manufactured by Shimatsu). The bacterial culture was added to a solution of 15% fetal bovine serum in DMEM to a final bacteria concentration of approximately 10$^6$/mL. An aliquot (0.8 mL) was transferred to a 1.5 mL snap-top polyethylene tube. An aliquot (0.004–0.040 mL) of the test compound stock solution prepared in water, ethanol or dimethylsulfoxide at 0.80–8.0 mM was added to the tube. Compounds were tested at a concentration of 16 µM. The tubes were placed in a light device as described in EXAMPLE 1 and irradiated with 1.3 J/cm$^2$, 1.2 J/cm$^2$, and finally 2.5 J/cm$^2$, for a total of 5 J/cm$^2$. 150 µL were removed for testing after each pulse period. Sterile 13 mL dilution tubes were prepared; each test compound required one tube with 0.4 mL of LB broth and four tubes containing 0.5 mL of LB broth. To make the dilutions, a 0.050 mL aliquot of the irradiated solution of phage and test compound was added to the first dilution tube of 0.5 mL of media then 0.050 mL of this solution was added to the second tube of 0.5 mL medium (1:10). The second solution was then diluted serially (1:10) into the remaining tubes. 100 µL of the original sample and each dilution are plated separately onto LB agar plates and incubated at 37° C. overnight. The colony forming units were then counted the following morning and the liter of the phage remaining after phototreatment was calculated based on the dilution factors.

The following controls were run: the "bacteria only" in which bacteria was not treated with test compound and not irradiated (listed as "starting titer" in the tables below); the "UV only" in which the bacteria was irradiated in the absence of test compound. Dark controls were not performed here for reasons set forth in Example 9 above.

The results were as follows. The starting titer of bacteria was 6.5 logs. After 5 J/cm$^2$ irradiation, the log kill for the various compounds tested were as follows: 8-MOP—1.9 logs, AMT—5.2 logs, Compound 2—>5.5, Compound 6—>5.5. From these results, it is clear that the compounds of the present invention are more efficient than both AMT and 8-MOP at inactivating a gram negative bacteria.

EXAMPLE 14

In the above examples, psoralens of the present invention have been demonstrated to be effective for inactivating pathogens, such as bacteria (pseudomonus), bacteriophage (R17) and viruses (HIV and DHBV). Without intending to be limited to any method by which the compounds of the present invention inactivate pathogens, it is believed that inactivation results from light induced binding of the psoralens to the nucleic acid of the pathogens. As discussed above, AMT is known both for its pathogen inactivation efficiency and its accompanying mutagenic action in the dark at low concentrations. In contrast, the less active psoralens, such as 8-MOP, that have been examined previously, show significantly less mutagenicity. This example establishes that photobinding and mutagenicity are not linked phenomenon in the compounds of the present invention. The psoralens of the present invention have exceptional pathogen inactivation efficiency while displaying only minimal mutagenicity.

In this example the compounds of the present invention are tested for their dark mutagenicity using an Ames assay. The procedures used for the Salmonella mutagenicity test as described in detail by Maron and Ames were followed exactly. Maron, D. M. and B. N. Ames, Mutation Research 113:173 (1983). A brief description for each procedure is given here. The tester strains TA97a, TA98, TA100, TA102, TA1537 and TA1538 were obtained from Dr. Ames. TA97a, TA98, TA1537 and TA1538 are frameshift tester strains. TA100 and TA102 are base-substitution tester strains. Upon receipt each strain was cultured under a variety of conditions to confirm the genotypes specific to the strains.

The standard Salmonella tester strains used in this study require histidine for growth since each tester strain contains a different type of mutation in the histidine operon. In addition to the histidine mutation, these tester strains contain other mutations, described below, that greatly increase their ability to detect mutagen.

Histidine Dependence: The requirement for histidine was tested by streaking each strain first on a minimal glucose plate supplemented only with biotin and then on a minimal glucose plate supplemented with biotin and histidine. All strains grew the lack of growth of the strains in the absence of histidine.

rfa Mutation: A mutation which causes partial loss of the lipopolysaccharide barrier that coats the surface of the bacteria thus increasing permeability to large molecules was confirmed by exposing a streaked nutrient agar plate coated with the tester strain to crystal violet. First 100 µL of each culture was added to 2 mL of molten minimal top agar and poured onto a nutrient agar plate. Then a sterile filter paper disc saturated with crystal violet was placed at the center of each plate. After 16 hours of incubation at 37° C. the plates were scored and a clear zone of no bacterial growth was found around the disc, confirming the rfa mutation.

uvrB Mutation: Three strains used in this study contain a deficient UV repair system (TA97a, TA98, TA100, TA1537 and TA1538). This trait was tested for by streaking the strains on a nutrient agar plate, covering half of the plate, and irradiating the exposed side of the plate with germicidal lamps. After incubation growth was only seen on the side of the plate shielded from UV irradiation.

R-factor: The tester strains (TA97a, TA98, TA100, and TA102) contain the pKM101 plasmid that increases their sensitivity to mutagens. The plasmid also confers resistance to ampicillin to the bacteria. This was confirmed by growing the strains in the presence of ampicillin.

pAQ1: Strain TA102 also contains the pAQ1 plasmid that further enhances its sensitivity to mutagens. This plasmid also codes for tetracycline resistance. To test for the presence of this plasmid TA102 was streaked on a minimal glucose plate containing histidine, biotin, and tetracycline. The plate was incubated for 16 hours at 37° C. The strain showed normal growth indicating the presence of the pAQ1 plasmid.

The same cultures used for the genotype testing were again cultured and aliquots were frozen under controlled conditions. The cultures were again tested for genotype to confirm the fidelity of the genotype upon manipulation in preparing the frozen permanents.

The first tests done with the strains were to determine the range of spontaneous reversion for each of the strains. With each mutagenicity experiment the spontaneous reversion of the tester strains to histidine independence was measured and expressed as the number of spontaneous revertants per plate. This served as the background controls. A positive mutagenesis control was included for each tester strain by using a diagnostic mutagen suitable for that strain (2-aminofluorene at 5 mg/plate for TA98 and sodium azide at 1.5 mg/plate for TA100).

For all experiments, the pre-incubation procedure was used. In this procedure one vial of each tester strain was thawed and 20 µL of this culture was added to 6 mL of Oxoid Nutrient Broth #2. This solution was allowed to shake for 10 hours at 37° C. In the pre-incubation procedure, 0.1 mL of this overnight culture was added to each of the required number of sterile test tubes. To half of the tubes 0.5 mL of a 10% S-9 solution containing Aroclor 1254 induced rat liver extract (Molecular Toxicology Inc., Annapolis, Md.), and MgCl$_2$, KCl, glucose-6-phosphate, NADP, and sodium phosphate buffer (Sigma, St. Louis, Mo.) were added. To the other half of the tubes 0.5 mL of 0.2M sodium phosphate buffer, pH 7.4, was used in place of the S-9 mixture (the -S9 samples). Finally 0.1 mL of the test solution containing either 0, 0.1, 0.5, 1, 5, 10, 50, 100, 250, or 500 µg/mL of the test compound was added. The 0.7 mL mixture was vortexed and then pre-incubated while shaking for 20 minutes at 37° C. After shaking, 2 mL of molten top agar supplemented with histidine and biotin were added to the 0.7 mL mixture and immediately poured onto a minimal glucose agar plate (volume of base agar was 20 mL). The top agar was allowed 30 minutes to solidify and then the plates were inverted and incubated for 44 hours at 37° C. After incubation the number of revertant colonies on each plate were counted. The results appear in TABLES 10 (A)–16 (B), below. ("n" represents the number of replicates performed for each data point.)

TABLE 10(A)

AMT

| STRAIN Dose µg/plate | TA97a −S9 | TA97a +S9 | TA98 −S9 | TA98 +S9 | TA100 −S9 | TA100 +S9 |
|---|---|---|---|---|---|---|
| 0 | 109 n = 23 | 158 n = 39 | 20 n = 38 | 25 n = 53 | 126 n = 41 | 123 n = 56 |
| 0.1 | 14 n = 3 | −23 n = 6 | 3 n = 3 | 1 n = 6 | −10 n = 3 | −16 n = 6 |
| 0.5 | 9 n = 3 | 32 n = 6 | 5 n = 3 | 3 n = 6 | 13 n = 3 | −12 n = 6 |
| 1 | 54 n = 3 | 32 n = 6 | 5 n = 3 | 21 n = 6 | 17 n = 3 | −19 n = 6 |
| 5 | 73 n = 3 | 149 n = 6 | 16 n = 6 | 232 n = 9 | 59 n = 9 | −6 n = 12 |
| 10 | | | 20 n = 9 | 403 n = 9 | 105 n = 15 | 17 n = 15 |
| 50 | | | 69 n = 9 | 620 n = 9 | 73 n = 9 | 52 n = 9 |
| 100 | | | 114 n = 9 | 745 n = 9 | 75 n = 9 | 85 n = 9 |
| 250 | | | 112 n = 6 | 933 n = 6 | 24 n = 6 | 89 n = 6 |
| Positive Control | | 5 µg/plate 2-Amino fluorene 808 n = 21 | | 5 µg/plate 2-Amino-fluorene 1154 n = 35 | 1.5 µg/plt sodium azide 965 n = 38 | |

TABLE 11(A)

8-MOP

| STRAIN Dose µg/plate | TA102 −S9 | TA102 +S9 | TA1537 −S9 | TA1537 +S9 |
|---|---|---|---|---|
| 0 | 346 n = 26 | 404 n = 41 | 9 n = 30 | 9 n = 45 |
| 1 | −55 n = 14 | −46 n = 17 | | |
| 10 | −57 n = 14 | −27 n = 17 | | |
| 30 | | | 5 n = 3 | 1 n = 6 |
| 60 | | | 3 n = 3 | 1 n = 6 |
| 90 | | | −1 n = 3 | −4 n = 6 |
| 100 | 217 n = 14 | 290 n = 17 | | |
| 500 | 781 n = 11 | 1179 n = 11 | | |
| Positive Control | 100 µ/plt hydrogen peroxide 660 n = 23 | | 10 µg/plt 9-Amino-Aridine 284 n = 6 | 10 µg/plt 2-Amino-fluorene 73 n = 24 |

TABLE 10(B)

AMT

| STRAIN Dose µg/plate | TA102 −S9 | TA102 +S9 | TA1537 −S9 | TA1537 +S9 | TA1538 −S9 | TA1538 +S9 |
|---|---|---|---|---|---|---|
| 0 | 346 n = 26 | 404 n = 41 | 9 n = 30 | 9 n = 45 | 15 n = 30 | 19 n = 42 |
| 0.1 | 27 n = 3 | −20 n = 6 | 0 n = 3 | 2 n = 6 | 3 n = 3 | 3 n = 6 |
| 0.5 | 47 n = 3 | 5 n = 6 | 3 n = 9 | 2 n = 12 | 4 n = 9 | 13 n = 12 |
| 1 | 88 n = 3 | −17 n = 6 | 5 n = 9 | 3 n = 12 | 4 n = 9 | 37 n = 12 |
| 5 | 266 n = 3 | 51 n = 6 | 44 n = 9 | 22 n = 12 | 13 n = 18 | 177 n = 21 |
| 10 | | | 52 n = 9 | 30 n = 9 | 14 n = 9 | 255 n = 9 |
| 50 | | | 2688 n = 9 | 94 n = 9 | | |
| 100 | | | 2058 n = 9 | 686 n = 9 | | |
| 250 | | | 434 n = 9 | 3738 n = 12 | | |
| Positive Control | 100 µg/pl hydrogen peroxide 660 n = 23 | | 10 µg/plt 9-Amino acridine 284 n = 6 | 10 µg/plt 2-Amino-fluorene 73 n = 24 | 5 µg/plate 2-Amino-fluorene 1064 n = 30 | |

TABLE 11(B)

8-MOP

| STRAIN Dose µg/plate | TA102 −S9 | TA102 +S9 | TA1537 −S9 | TA1537 +S9 |
|---|---|---|---|---|
| 0 | 346 n = 26 | 404 n = 41 | 9 n = 30 | 9 n = 45 |
| 1 | −55 n = 14 | −46 n = 17 | | |
| 10 | −57 n = 14 | −27 n = 17 | | |
| 30 | | | 5 n = 3 | 1 n = 6 |
| 60 | | | 3 n = 3 | 1 n = 6 |
| 90 | | | −1 n = 3 | −4 n = 6 |
| 100 | 217 n = 14 | 290 n = 17 | | |
| 500 | 781 n = 11 | 1179 n = 11 | | |
| Positive Control | 100 µg/plt hydrogen peroxide 660 n = 23 | | 10 µg/plt 9-Amino-Acridine 284 n = 6 | 10 µg/plt 2-Amino-fluorene 73 n = 24 |

TABLE 12

Compound 1

| STRAIN Dose µg/plate | TA100 −S9 | TA100 +S9 | TA1538 −S9 | TA1538 +S9 |
|---|---|---|---|---|
| 0 | 126 n = 41 | 123 n = 56 | 15 n = 30 | 19 n = 42 |
| 5 | 292 n = 3 | −24 n = 3 | 10 n = 3 | 21 n = 3 |
| 10 | 337 n = 3 | −22 n = 3 | 12 n = 3 | 22 n = 3 |
| Positive Control | 1.5 µg/plate Sodium Azide 965 n = 38 | | | 5 µg/plate 2-Amino-fluorene 1064 n = 30 |

TABLE 13(A)

Compound 2

| STRAIN Dose µg/plate | TA1537 −S9 | TA1537 +S9 | TA1538 −S9 | TA1538 +S9 |
|---|---|---|---|---|
| 0 | 9 n = 30 | 9 n = 45 | 15 n = 30 | 19 n = 42 |
| 5 | | | −8 n = 3 | 2 n = 3 |
| 10 | 36 n = 3 | 5 n = 3 | −13 n = 3 | 4 n = 3 |
| 50 | 282 n = 3 | 40 n = 3 | | |
| 100 | 258 n = 3 | 88 n = 3 | | |
| 250 | 176 n = 3 | 744 n = 3 | | |
| 500 | 114 n = 3 | 395 n = 3 | | |
| Positive | 10 µg/plt | 10 µg/plt | | 5 µg/plate |

TABLE 13(A)-continued

Compound 2

| STRAIN Dose µg/plate | TA1537 −S9 | TA1537 +S9 | TA1538 −S9 | TA1538 +S9 |
|---|---|---|---|---|
| Control | 9-Amino-acridine 284 n = 6 | 2-Amino-fluorene 73 n = 24 | | 2-Amino-fluorene 1064 n = 30 |

TABLE 13(B)

Compound 2

| STRAIN Dose µg/plate | TA1537 −S9 | TA1537 +S9 | TA1538 −S9 | TA1538 +S9 |
|---|---|---|---|---|
| 0 | 9 n = 30 | 9 n = 45 | 15 n = 30 | 19 n = 42 |
| 5 | | | −8 n = 3 | 2 n = 3 |
| 10 | 36 n = 3 | 5 n = 3 | −13 n = 3 | 4 n = 3 |
| 50 | 282 n = 3 | 40 n = 3 | | |
| 100 | 258 n = 3 | 88 n = 3 | | |
| 250 | 176 n = 3 | 744 n = 3 | | |
| 500 | 114 n = 3 | 395 n = 3 | | |
| Positive Control | 10 µ/plt 9-Amino-acridine 284 n = 6 | 10 µg/plt 2-Amino-fluorene 73 n = 24 | | 5 µg/plate 2-Amino-fluorene 1064 n = 30 |

TABLE 14

Compound 3

| STRAIN Dose µg/plate | TA100 −S9 | TA100 +S9 | TA1538 −S9 | TA1538 +S9 |
|---|---|---|---|---|
| 0 | 126 n = 41 | 123 n = 56 | 15 n = 30 | 19 n = 42 |
| 5 | 47 n = 3 | −19 n = 3 | 0 n = 3 | 1 n = 3 |
| 10 | 47 n = 3 | 8 n = 3 | −6 n = 3 | 9 n = 3 |
| Positive Control | 1.5 µg/plt Sodium Azide 965 n = 38 | | | 5 µg/plt 2-Amino-fluorene 1064 n = 30 |

TABLE 15

Compound 4

| STRAIN Dose µg/plate | TA100 −S9 | TA100 +S9 | TA1538 −S9 | TA1538 +S9 |
|---|---|---|---|---|
| 0 | 126 n = 41 | 123 n = 56 | 15 n = 30 | 19 n = 42 |
| 5 | −41 n = 3 | −10 n = 3 | −2 n = 3 | 7 n = 3 |
| 10 | 3 | −3 | −2 | −2 |

TABLE 15-continued

Compound 4

| STRAIN Dose µg/plate | TA100 −S9 | TA100 +S9 | TA1538 −S9 | TA1538 +S9 |
|---|---|---|---|---|
| Positive Control | n = 3 1.5 µg/plate Sodium Azide 965 n = 38 | n = 3 | n = 3 | n = 3 5 µg/plate 2-Amino-fluorene 1064 n = 30 |

TABLE 16(A)

Compound 6

| STRAIN Dose µg/plate | TA98 −S9 | TA98 +S9 | TA100 −S9 | TA100 +S9 |
|---|---|---|---|---|
| 0 | 20 n = 38 | 25 n = 53 | 126 n = 41 | 123 n = 56 |
| 5 | | | −32 n = 3 | 12 n = 3 |
| 10 | 12 n = 3 | −5 n = 3 | 3 n = 9 | −5 n = 9 |
| 50 | 12 n = 3 | 2 n = 3 | 2 n = 6 | 24 n = 6 |
| 100 | 22 n = 6 | 20 n = 6 | −18 n = 6 | −2 n = 6 |
| 250 | 12 n = 3 | 40 n = 3 | | −38 n = 3 |
| 500 | 9 n = 3 | 52 n = 3 | | |
| Positive Control | | 5 µg/plate 2-Amino-fluorene 1154 n = 35 | 1.5 µg/plate Sodium Azide 965 n = 38 | |

TABLE 16(B)

Compound 6

| STRAIN Dose µg/plate | TA1537 −S9 | TA1537 +S9 | TA1538 −S9 | TA1538 +S9 |
|---|---|---|---|---|
| 0 | 9 n = 30 | 9 n = 45 | 15 n = 30 | 19 n = 42 |
| 5 | | | −5 n = 3 | 0 n = 3 |
| 10 | 141 n = 6 | −1 n = 6 | −2 n = 3 | 8 n = 3 |
| 50 | 2010 n = 6 | 17 n = 6 | | |
| 100 | 795 n = 6 | 35 n = 6 | | |
| 250 | 228 n = 6 | 99 n = 6 | | |
| 500 | 43 n = 3 | 369 n = 3 | | |
| Positive COntrol | 10 µg/plate 9-Amino-acridine 284 n = 6 | 10 µg/plate 2-Amino-fluorene 73 n = 24 | | 5 µg/plate 2-Amino-fluorene 1064 n = 30 |

Maron and Ames (1983) describe the conflicting views with regard to the statistical treatment of data generated from the test. In light of this, this example adopts the simple model of mutagenicity being characterized by a two-fold or greater increase in the number of revertants above background (in bold in the tables), as well as dose dependent mutagenic response to drug.

With regard to 8-MOP, the only mutagenic response detected was a weak base-substitution mutagen in TA102 at 500 µg/plate (TABLE 14 (B)).

In sharp contrast, AMT (TABLE 13 (A) and 13 (B)) showed frameshift mutagenicity at between 5 and 10 µg/plate in TA97a and TA98, at 5 µg/plate in TA1537 and at 1 µg/plate in TA1538. AMT showed no significant base-substitution mutations.

Looking at Compound 1, the only mutagenic response detected was a weak frameshift mutagen in TA1538 at 5 µg/plate in the presence of S9. Compound 1 also displayed mutation in the TA100 strain, but only in the absence of S9. Compound 2 also showed weak frameshift mutagenicity in the presence of S9 in TA98 and TA1537. Compounds 3 and 4 showed no mutagenicity. Compound 6 had no base substitution mutagenicity, but showed a frameshift response in TA98 in the presence of S9 at concentrations of 250 µg/plate and above. It also showed a response at 50 µg/plate in TA1537 in the presence of S9. Both responses are significantly below that of AMT, which displayed mutagenicity at much lower concentrations (5 µg/plate).

From this data it is clear that the compounds of the present invention are less mutagenic than AMT, as defined by the Ames test. At the same time, these compounds show much higher inactivation efficiency than 8-MOP, as shown in Examples 9 and 13. These two factors support that the compounds of the present invention combine the best features of both AMT and 8-MOP, high inactivation efficiency and low mutagenicity.

EXAMPLE 15

Figure 20A:
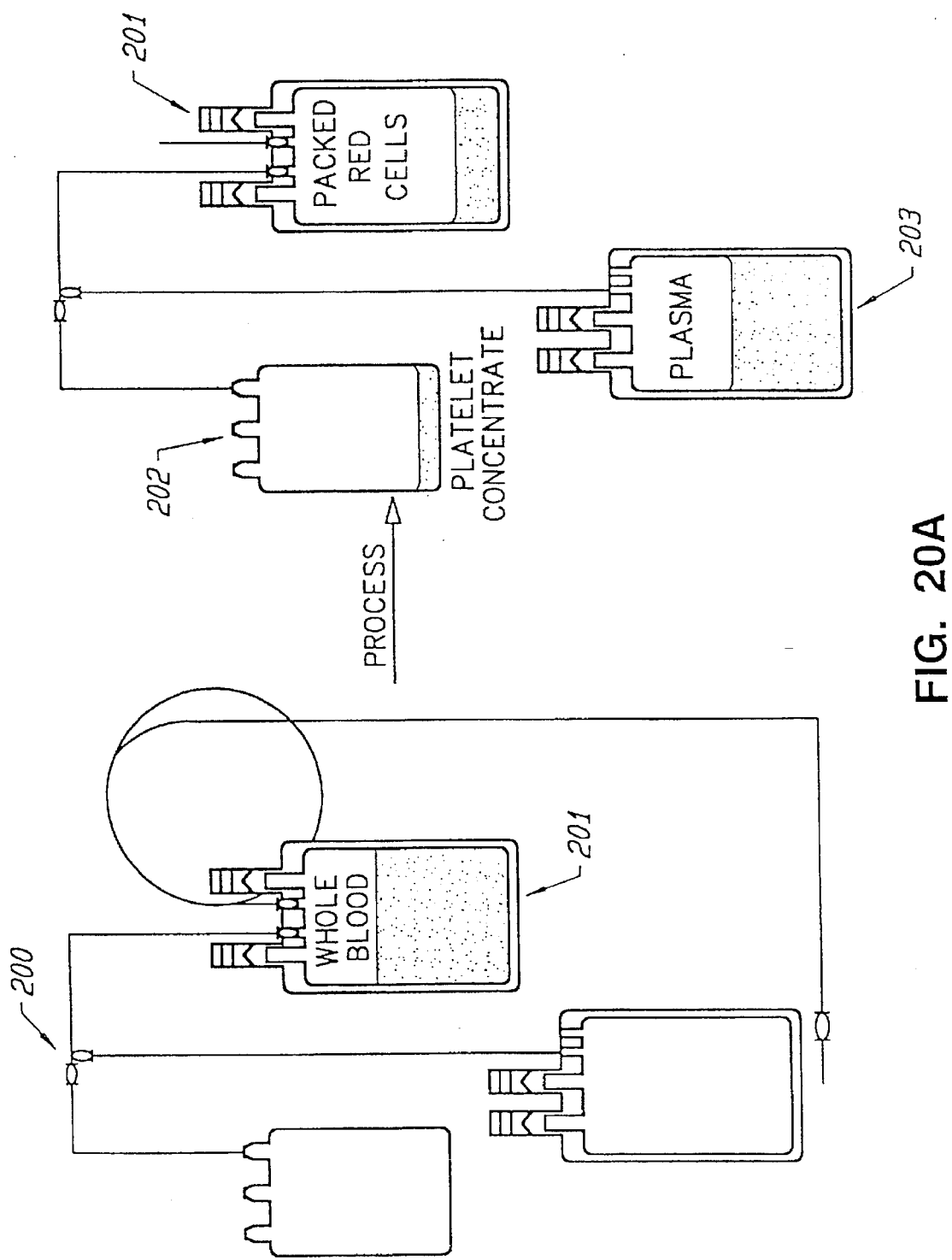
FIG. 20A schematically shows the standard blood product separation approach used presently in blood banks.

In Example 12, the compounds of the present invention exhibited the ability to inactivate pathogens in synthetic media. This example describes methods by which synthetic media and compounds of the present invention may be introduced and used for inactivating pathogens in blood. FIG. 20A schematically shows the standard blood product separation approach used presently in blood banks. Three bags are integrated by flexible tubing to create a blood transfer set (200) (e.g., commercially available from Baxter, Deerfield, Ill.). After blood is drawn into the first bag (201), the entire set is processed by centrifugation (e.g., Sorvall™ swing bucket centrifuge, Dupont), resulting in packed red cells and platelet rich plasma in the first bag (201). The plasma is expressed off of the first bag (201) (e.g., using a Fenwall™ device for plasma expression), through the tubing and into the second bag (202). The first bag (201) is then detached and the two bag set is centrifuged to create platelet concentrate and platelet-poor plasma; the latter is expressed off of the second bag (202) into the third bag (203).

Figure 20B:
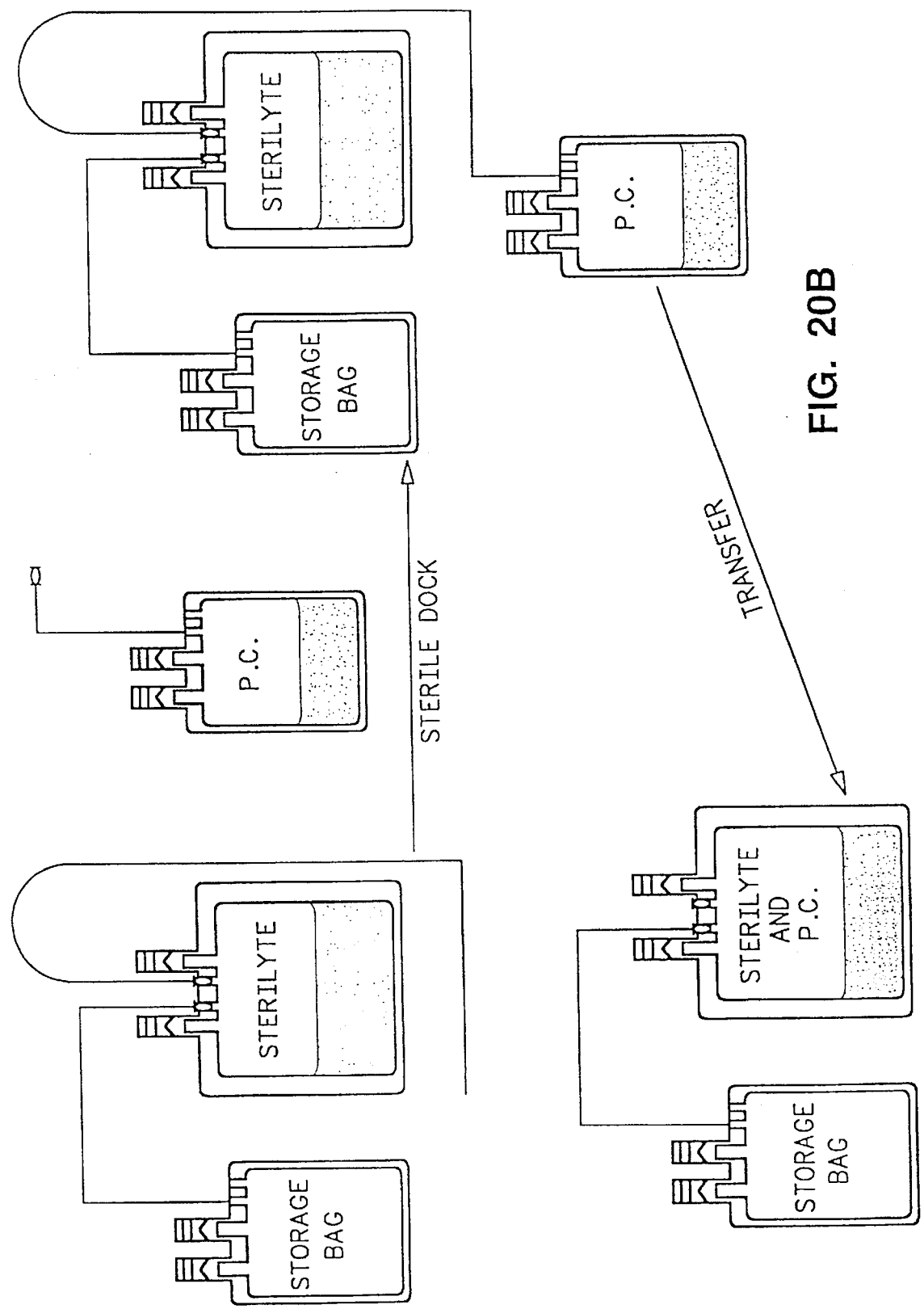
FIG. 20B schematically shows an embodiment of the present invention whereby synthetic media is introduced to platelet concentrate prepared as in FIG. 20A.

FIG. 20B schematically shows an embodiment of the present invention by which synthetic media and photoactivation compound are introduced to platelet concentrate prepared as in FIG. 20A. A two bag set (300) is sterile docked with the platelet concentrate bag (202) (indicated as "P.C."). Sterile docking is well-known to the art. See e.g., U.S. Pat. No. 4,412,835 to D. W. C. Spencer, hereby incorporated by reference. See also U.S. Pat. Nos. 4,157,723 and 4,265,280, hereby incorporated by reference. Sterile docking devices are commercially available (e.g., Terumo, Japan).

One of the bags (301) of the two bag set (300) contains a synthetic media formulation of the present invention (indicated as "STERILYTE"). In the second step shown in FIG. 20B, the platelet concentrate is mixed with the synthetic media by transferring the platelet concentrate to the synthetic media bag (301). The photoactivation compound can be in the bag containing synthetic media (301), added at the point of manufacture. Alternatively, the compound can be mixed with the blood at the point of collection, if the compound is added to the blood collection bag (FIG. 20A, 201) at the point of manufacture. The compound may be either in dry form or in a solution compatible with the maintainance of blood.

Figure 20C:
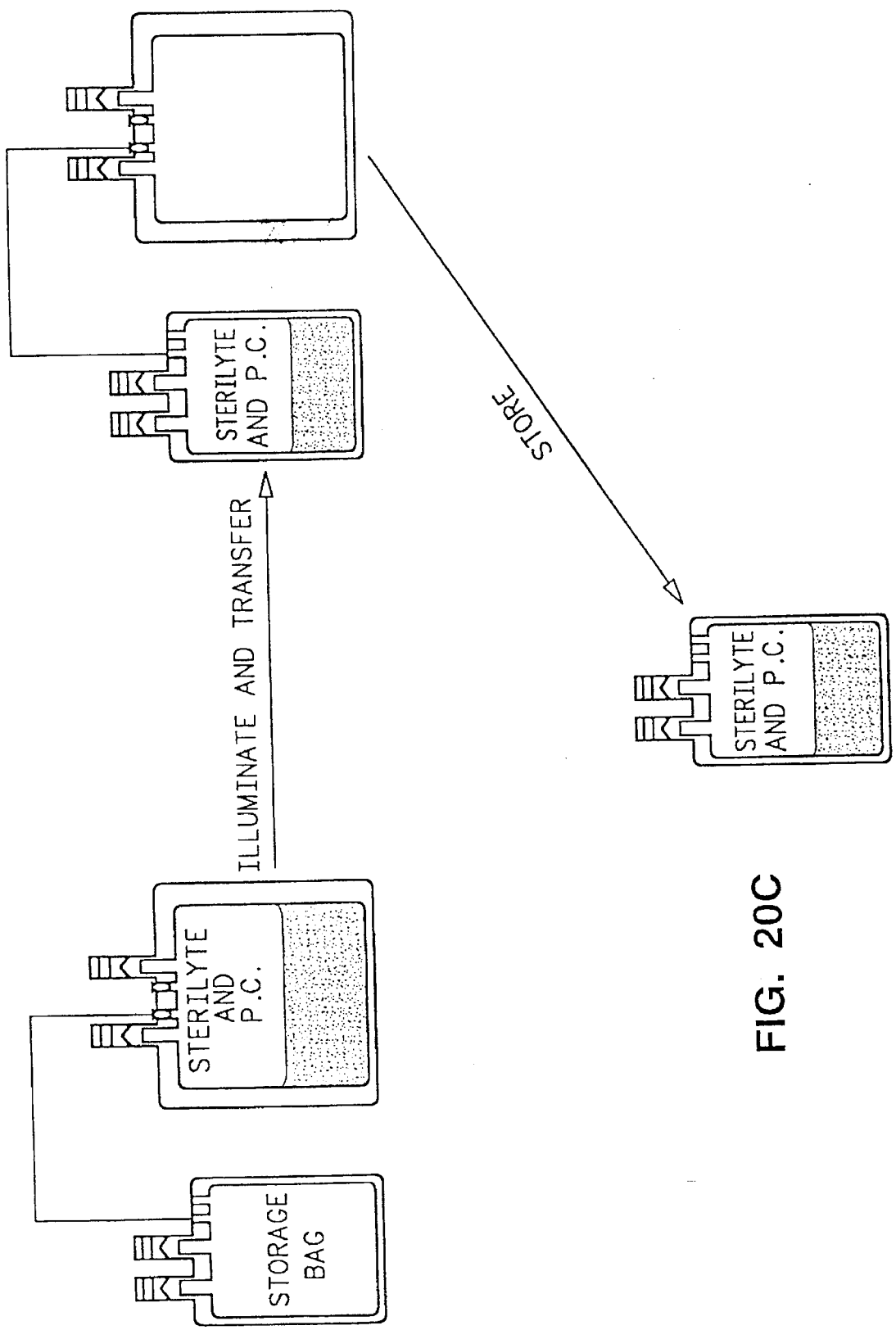
FIG. 20C schematically shows one embodiment of the decontamination approach of the present invention applied specifically to platelet concentrate diluted with synthetic media as in FIG. 20B.

FIG. 20C schematically shows one embodiment of the decontamination approach of the present invention applied specifically to platelet concentrate diluted with synthetic media as in FIG. 20B. In this embodiment, platelets have been transferred to a synthetic media bag (301). The photoactivation compound either has already been introduced in the blood collection bag (201) or is present in the synthetic media bag (301) to which the platelets are now transferred. This bag (301), which has UV light transmission properties and other characteristics suited for the present invention, is then placed in a device (such as that described in Example 1, above) and illuminated.

Following phototreatment, the decontaminated platelets are transferred from the synthetic media bag (301) into the storage bag (302) of the two bag set (300). The storage bag can be a commercially available storage bag (e.g., CLX bag from Cutter).

It is to be understood that the invention is not to be limited to the exact details of operation or exact compounds, composition, methods, or procedures shown and described, as modifications and equivalents will be apparent to one skilled in the art.

We claim:

1. A psoralen compound, consisting of:

a) a substituent $R_1$ on the 5' carbon atom, selected from the group consisting of:

$-(CH_2)_u-NH_2$, $-(CH_2)_w-R_2-(CH_2)_z-NH_2$, $-(CH_2)_w-R_2-(CH_2)_x-R_3-(CH_2)_z-NH_2$, and $-(CH_2)_w-R_2-(CH_2)_x-R_3-(CH_2)_y-R_4-(CH_2)_z-NH_2$;

wherein $R_2$, $R_3$, and $R_4$ are independently selected from the group consisting of O and NH, and in which u is a whole number from 3 to 10, w is a whole number from 1 to 5, x is a whole number from 2 to 5, y is a whole number from 2 to 5, and z is a whole number from 2 to 6; and, b) substituents $R_5$, $R_6$, and $R_7$ on the 4, 4', and 8 carbon atoms respectively, independently selected from the group consisting of H and $(CH_2)_v CH_3$, where v is a whole number from 0 to 5, and where when $R_1$ is $(CH_2)_u-NH_2$, $R_7$ is $(CH_2)_v-CH_3$; or a salt thereof.

2. A compound of claim 1, wherein said substituent $R_1$ is $-CH_2-NH-(CH_2)_4-NH_2$, and wherein said substituents $R_5$, $R_6$, and $R_7$ are all $CH_3$.

* * * * *